US010052478B2

(12) United States Patent
Greenberg et al.

(10) Patent No.: US 10,052,478 B2
(45) Date of Patent: Aug. 21, 2018

(54) IMPLANTABLE DEVICE FOR THE BRAIN

(71) Applicant: Second Sight Medical Products, Inc., Sylmar, CA (US)

(72) Inventors: Robert J Greenberg, Los Angeles, CA (US); Brian V Mech, Santa Clara, CA (US); Kelly H McClure, Simi Valley, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

(21) Appl. No.: 15/457,482

(22) Filed: Mar. 13, 2017

(65) Prior Publication Data

US 2017/0296808 A1   Oct. 19, 2017

Related U.S. Application Data

(62) Division of application No. 12/180,436, filed on Jul. 25, 2008, now Pat. No. 9,592,377.

(60) Provisional application No. 60/952,530, filed on Jul. 27, 2007.

(51) Int. Cl.
*A61N 1/05* (2006.01)
*A61N 1/378* (2006.01)
*A61N 1/372* (2006.01)
*A61N 1/375* (2006.01)
*A61N 1/36* (2006.01)
(Continued)

(52) U.S. Cl.
CPC ......... *A61N 1/0531* (2013.01); *A61N 1/0534* (2013.01); *A61N 1/0539* (2013.01); *A61N 1/36082* (2013.01); *A61N 1/3758* (2013.01); *A61N 1/3787* (2013.01); *A61N 1/37229* (2013.01); *H05K 1/028* (2013.01); *H05K 1/111* (2013.01)

(58) Field of Classification Search
CPC ...... A61N 1/0551; A61N 1/05; A61N 1/0531; A61N 1/0534; A61N 1/0568; A61N 1/375; A61N 1/0529; A61N 1/0526; A61N 1/0476; A61N 1/3605; A61N 1/0539; A61B 2562/125; A61B 2562/0209; A61B 2562/046; A61B 2017/00867; A61B 2018/00083; A61B 2018/0016; A61L 2400/18; C08L 2201/12; A61H 39/002

See application file for complete search history.

(56) References Cited

U.S. PATENT DOCUMENTS

| 4,903,702 A | 2/1990 | Putz |
| 5,109,844 A | 5/1992 | de Juan, Jr. et al. |
| 5,215,088 A | 6/1993 | Nomnann et al. |

(Continued)

FOREIGN PATENT DOCUMENTS

WO   WO 2005/061045 A   7/2005

*Primary Examiner* — Deborah Malamud
(74) *Attorney, Agent, or Firm* — Scott Dunbar

(57) ABSTRACT

The present invention consists of an implantable device with at least one package that houses electronics that receives input data or signals, and optionally, power, from an external system through at least one coil attached to the at least one package, processes the input data and delivers electrical pulses to neural tissue through at least one array of multiple electrodes that is/are attached to the at least one package. The invention, or components thereof, is/are intended to be installed in the head, or on or in the cranium, or on the dura, or on or in the brain.

14 Claims, 43 Drawing Sheets

(51) Int. Cl.
*H05K 1/02* (2006.01)
*H05K 1/11* (2006.01)

(56) References Cited

U.S. PATENT DOCUMENTS

| | | |
|---|---|---|
| 5,792,186 A | 8/1998 | Rise |
| 5,843,148 A | 12/1998 | Gijsbers et al. |
| 5,935,155 A | 8/1999 | Humayun et al. |
| 5,948,007 A | 9/1999 | Starkebaum et al. |
| 6,016,449 A | 1/2000 | Fischell et al. |
| 6,024,702 A | 2/2000 | Iversen |
| 6,400,989 B1 | 6/2002 | Eckmiller |
| 6,427,086 B1 | 7/2002 | Fischell et al. |
| 6,458,157 B1 | 10/2002 | Suaning |
| 6,529,774 B1 | 3/2003 | Greene |
| 6,564,079 B1 * | 5/2003 | Cory ............... A61B 5/04001 600/393 |
| 6,647,296 B2 | 11/2003 | Fischell et al. |
| 6,976,998 B2 * | 12/2005 | Rizzo ................. A61F 2/14 607/54 |
| 7,006,872 B2 | 2/2006 | Gielen et al. |
| 7,212,864 B2 | 5/2007 | Wahlstrand et al. |
| 7,212,867 B2 | 5/2007 | Van Venrooij et al. |
| 7,242,982 B2 | 7/2007 | Singhal et al. |
| 7,257,446 B2 | 8/2007 | Greenberg et al. |
| 7,392,089 B2 | 6/2008 | Wahlstrand et al. |
| 2002/0038134 A1 * | 3/2002 | Greenberg ........... A61N 1/0543 607/1 |
| 2004/0176815 A1 | 9/2004 | Janzig et al. |
| 2004/0176831 A1 | 9/2004 | Gliner et al. |
| 2006/0009814 A1 | 1/2006 | Schulman |
| 2006/0247734 A1 | 11/2006 | Greenberg et al. |

\* cited by examiner

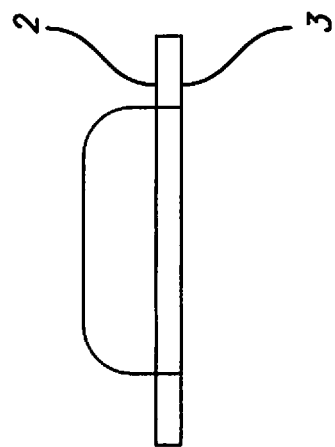
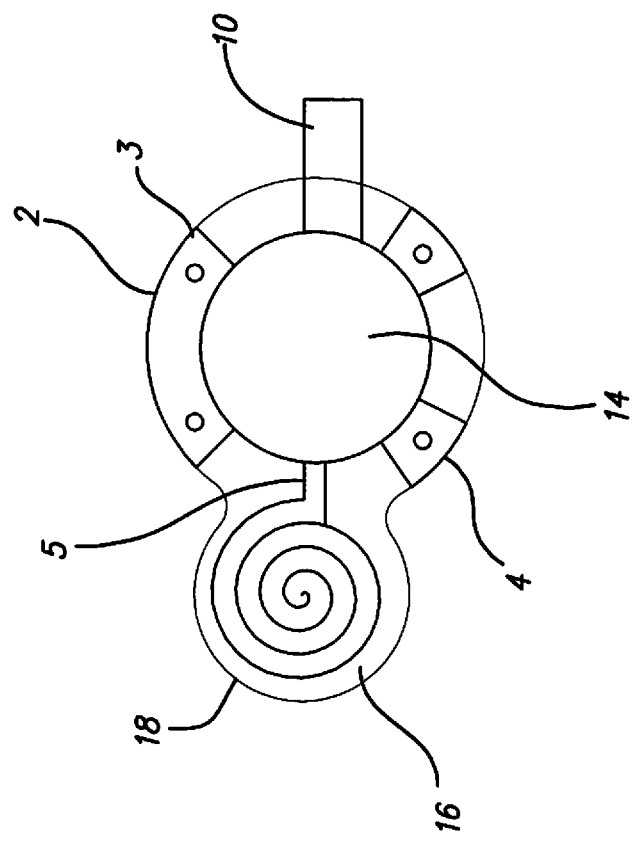
FIG. 1B
FIG. 1A

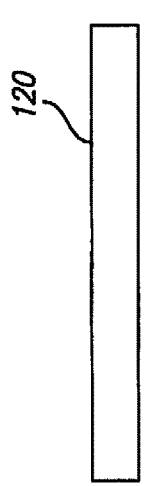
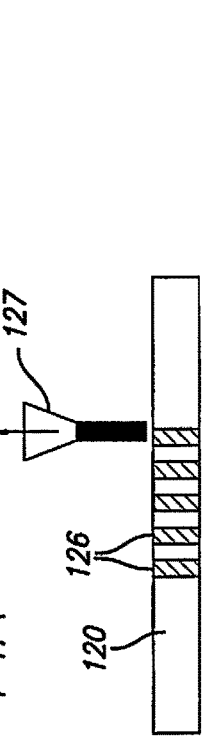
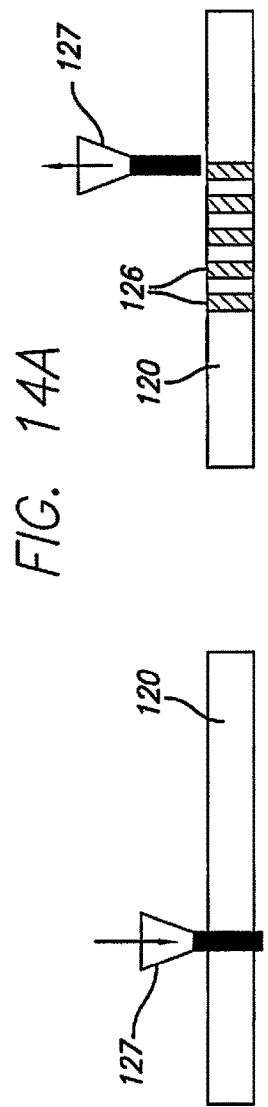
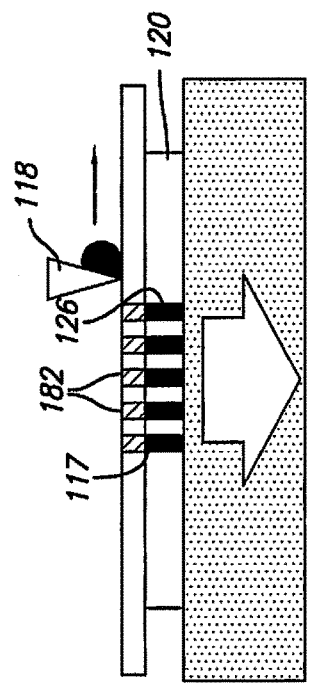
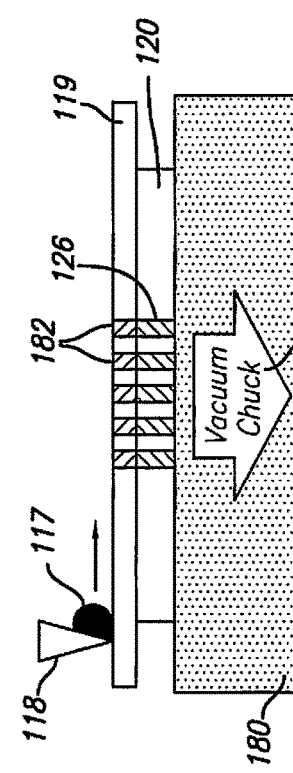
FIG. 14A
FIG. 14B
FIG. 14C
FIG. 14D
FIG. 14E

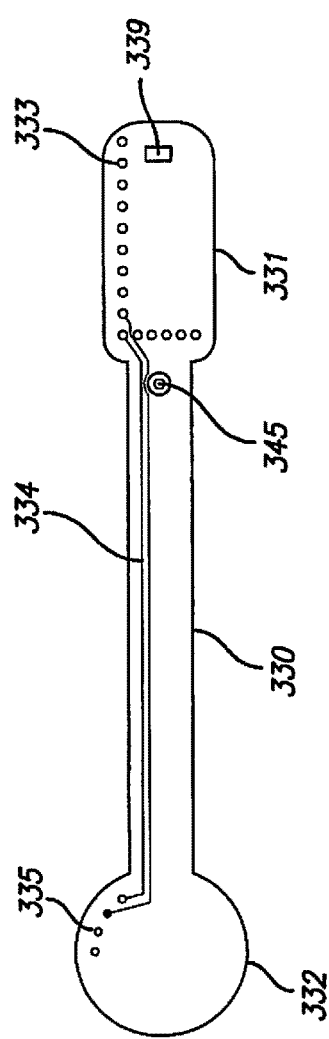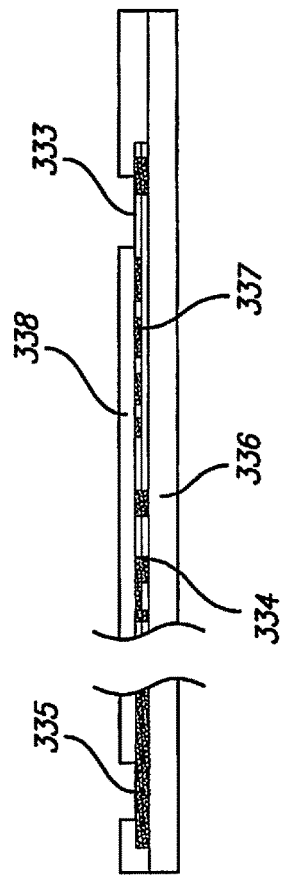
FIG. 17A
FIG. 17B

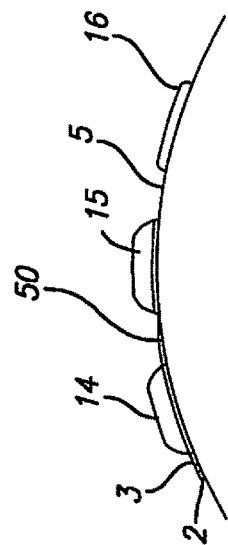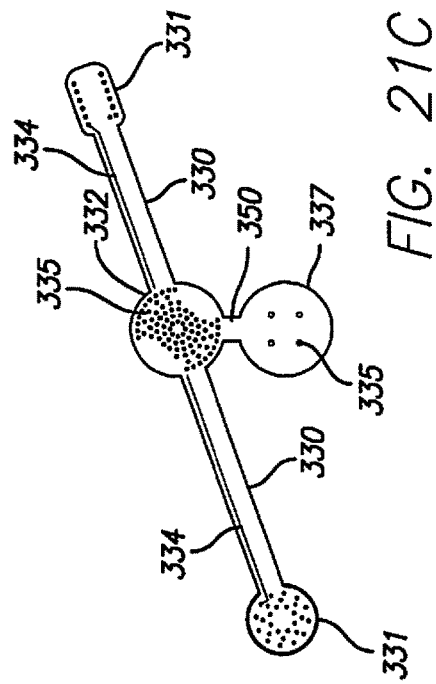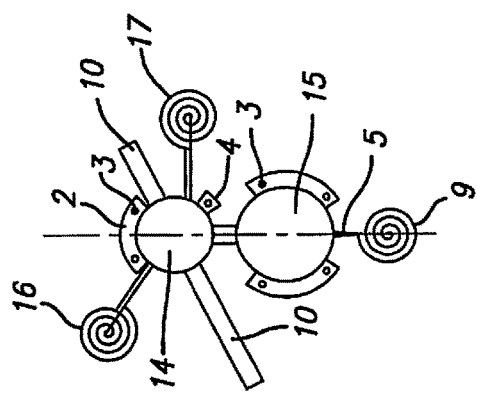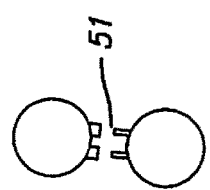
FIG. 21B
FIG. 21C
FIG. 21A
FIG. 21D

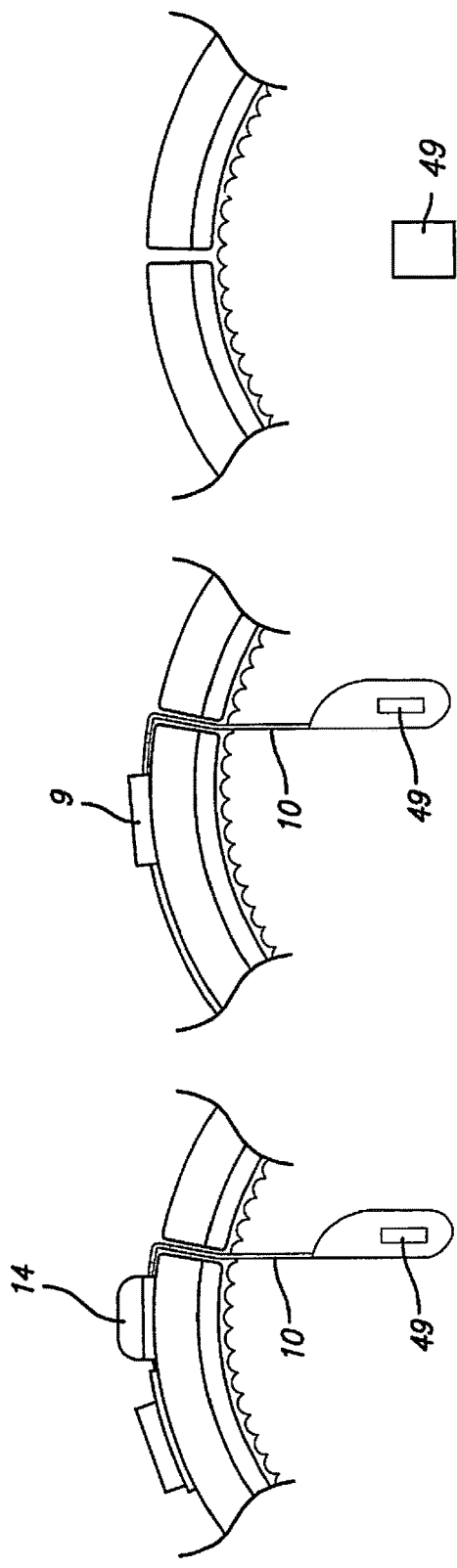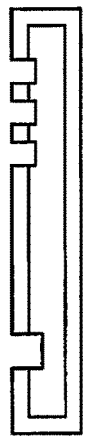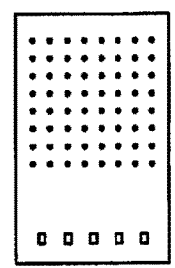
FIG. 22A  FIG. 22B  FIG. 22C
FIG. 22D  FIG. 22E  FIG. 22F

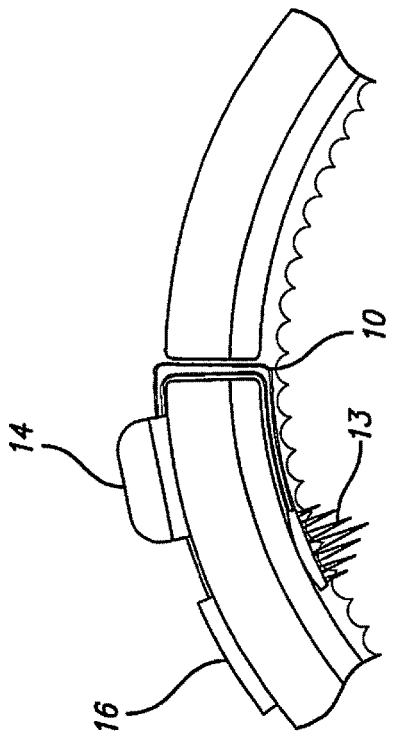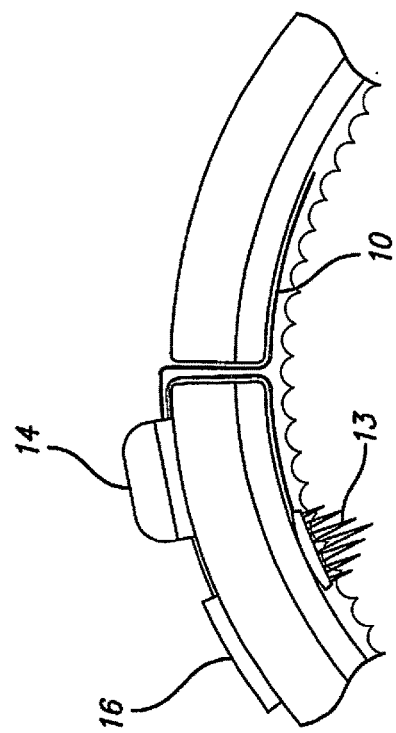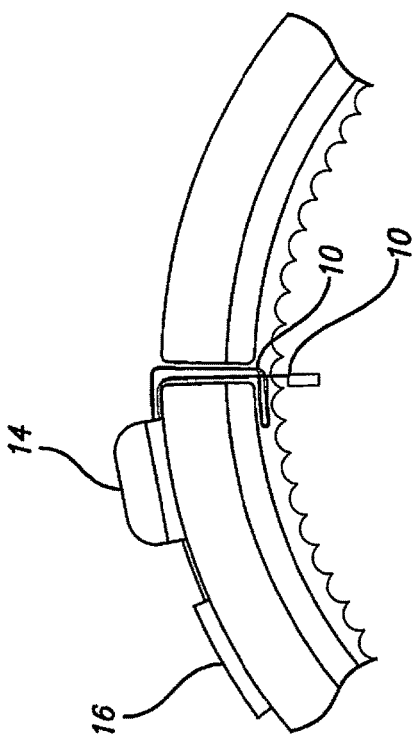

IMPLANTABLE DEVICE FOR THE BRAIN

CROSS REFERENCE TO RELATED APPLICATIONS

This application is a division of U.S. patent application Ser. No. 12/180,436, filed Jul. 25, 2008, for Implantable Device for the Brian, now U.S. Pat. No. 9,592,377 which claims priority to and incorporates by reference the following provisional applications: 60/952,530, filed Jul. 27, 2007, for High Electrode Count Brain Stimulator, 60/954,265, filed Aug. 6, 2007, for High Electrode Count Brain Stimulator, 60/954,798, filed Aug. 8, 2007, for High Electrode Count Brain Stimulator, 60/986,269, filed Nov. 7, 2008, for Package for an Implantable Device, and 61/017,507, filed Dec. 28, 2007, for Method of Providing a Soft Polymer on Top of a Hard Polymer.

GOVERNMENT RIGHTS NOTICE

This invention was made with government support under grant No. R24EY12893-01, awarded by the National Institutes of Health. The government has certain rights in the invention.

FIELD OF THE INVENTION

The present invention is an implantable device for interfacing with neural tissue primarily in order to stimulate the tissue and treat a neural disorder or diseases or conditions which stem from abnormal neural activity.

BACKGROUND OF THE INVENTION

Neural tissue can be artificially stimulated and activated by prosthetic devices that pass pulses of electrical current through electrodes on such a device. The passage of current causes changes in electrical potentials across neuronal membranes, which can initiate neuron action potentials, which are the means of information transfer in the nervous system.

Based on this mechanism, it is possible to input information into the central nervous system by coding the sensory information as a sequence of electrical pulses which are relayed to the central nervous system via the prosthetic device. In this way, it is possible to provide artificial sensations including vision, and interrupt the onset of movement disorders. Additionally, neural stimulation in the brain may be able to modulate obesity, anxiety, depression and other mood disorders.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

US Patent Application 2003/0109903 to Berrang describes a Low profile subcutaneous enclosure in particular, and metal over ceramic hermetic package for implantation under the skin.

SUMMARY OF THE INVENTION

The present invention consists of an implantable device with at least one package that houses electronics that receives input data or signals, and optionally, power, from an external system through at least one coil attached to at least one package, processes the input data and delivers electrical pulses to neural tissue through at least one array of multiple electrodes that is/are attached to the at least one package.

The invention, or components thereof, is/are intended to be installed in the head, or on or in the cranium or on the dura, or on or in the brain. Variations of the embodiments depend on the physical locations of the coil(s), package(s) and array(s) with respect to the head, cranium, dura, and brain. Additional variations include the ability of the implanted device to sense a physiological parameter, and/or record electrical signals from neural tissue, and/or measure electrical properties of the system. Novel features of the present invention include the small size of the implantable package which houses the controller, the high number of electrodes that are provided for stimulation and or sensing, and/or recording, and/or measuring, and the methods for manufacturing such a device. These features have unique applications in neural stimulation to treat or prevent disorders or disease. Other novel features will be made evident in the descriptions below.

The present invention includes an improved hermetic package, connected to a thin film array, for implantation in the human body, and particularly in the human head for the purposes of stimulating the brain on the surface or at some depth. The implantable device of the present invention includes an electrically non-conductive substrate including electrically conductive vias through the substrate. A circuit is flip-chip bonded to a subset of the vias. A second circuit is wire bonded to another subset of the vias. A cover is bonded to the substrate such that the cover, substrate and vias form a hermetic package. Finally, at least one thin film electrode array is attached to this package mechanically and electrically such that stimuli emitted from the electronics within the package may be transmitted to areas of the brain.

BRIEF DESCRIPTION OF THE DRAWINGS

FIG. 1A Shows a top view of the preferred package for the present invention illustrating basic structure and means of attachment.

FIG. 1B Shows a side view of the preferred package for the present invention illustrating the structure and means of attachment.

FIGS. 14A-14M respectively depict the fabrication stages of a feedthrough assembly in accordance with the process flow illustrated in FIG. 13.

FIG. 14A depicts a sectional view of a ceramic sheet.

FIG. 14B depicts a via hole being punched in the sheet of FIG. 14A.

FIG. 14C depicts several via holes punched in the sheet of FIG. 14A.

FIG. 14D depicts exemplary stencil printing with vacuum pull down process.

FIG. 14E depicts the end of the stenciling process of FIG. 14D.

FIG. 14F depicts paste inserted into the via holes.

FIG. 14G depicts exemplary multilayer lamination process.

FIG. 14H depicts the multiple layers laminated together.

FIG. 14I shows an exemplary laminated substrate.

FIG. 14J depicts lapping/grinding process.

FIG. 14K depicts the substrate after lamination.

FIG. 14L depicts dicing of the substrate to form multiple feedthrough assemblies.

FIG. 14M depicts multiple substrates after dicing.

FIG. 16A shows a side view of the substrate with conductive adhesive on the contacts.

FIG. 16B shows a top view of the flexible thin film with conductive adhesive on the bond pads.

FIG. 16C shows a side view of the flexible thin film with conductive adhesive on the bond pads.

FIG. 16D shows the substrate bonded to the flexible thin film with conductive adhesive.

FIG. 16E shows the substrate bonded to the flexible thin film with underfill between the conductive bumps.

FIG. 17A shows a top view of the thin film array of the present invention.

FIG. 17B shows a side view of the thin film array of the present invention.

FIGS. 21A-D show alternate embodiments including multiple implantable packages.

FIG. 21A shows an alternate embodiment with two electronics packages.

FIG. 21B shows the embodiment of FIG. 21A as it would sit on the cranium.

FIG. 21C shows a flexible circuit to connect multiple packages to electrode arrays.

FIG. 21D shows an alternate embodiment with detachable packages.

FIGS. 22A-F show further alternate embodiments and configurations.

FIG. 22A shows an alternate embodiment with a coated chip, such as a demultiplexer, on the thin film lead.

FIG. 22B shows an alternate embodiment where all of the electronics are in a coated chip on the thin film lead.

FIG. 22C shows an alternate embodiment where the coil and electronics are in a coated chip on the thin film lead.

FIG. 22D shows a side view of an alternate embodiment where the coated chip is integrated into the electrode array.

FIG. 22E shows a top view of an alternate embodiment where the coated chip is integrated into the electrode array.

FIG. 22F shows an end view of an alternate embodiment where the coated chip is integrated into the electrode array.

FIG. 23A shows a further alternate embodiment, including a penetrating electrode array in one location, and a surface electrode array on another thin film in a remote location.

FIG. 23B shows a further alternate embodiment, including a penetrating electrode array in one location, and a surface electrode array in a similar location.

FIG. 23C shows a penetrating thin film lead and a surface thin film lead.

FIG. 66A shows a first PDMS layer.

FIG. 66B shows a first polyimide layer on the first PDMS layer.

FIG. 66C shows a metal layer on the first polyimide layer.

FIG. 66D shows a second polyimide layer on the metal layer and first polyimide layer.

FIG. 66E shows holes made in the second polyimide layer for electrodes and bond pads.

FIG. 66F shows a second PDMS layer on the second polyimide layer.

FIG. 66G shows holes made in the second PDMS layer.

FIG. 66H shows electrodes plated in the holes in the second polyimide layer.

FIG. 67A shows a first PDMS layer.

FIG. 67B shows a first polyimide layer on the first PDMS layer.

FIG. 67C shows a metal layer on the first polyimide layer.

FIG. 67D shows a second polyimide layer on the first polyimide layer and the metal layer.

FIG. 67E shows a second PDMS layer on the second polyimide layer.

FIG. 67F shows holes through the second PDMS layer and second polyimide layer for electrodes and bond pads.

FIG. 67G shows electrodes plated in the holes in the second polyimide layer.

FIGS. 68A-D show a thin film array with penetrating electrodes.

Figure 68A:
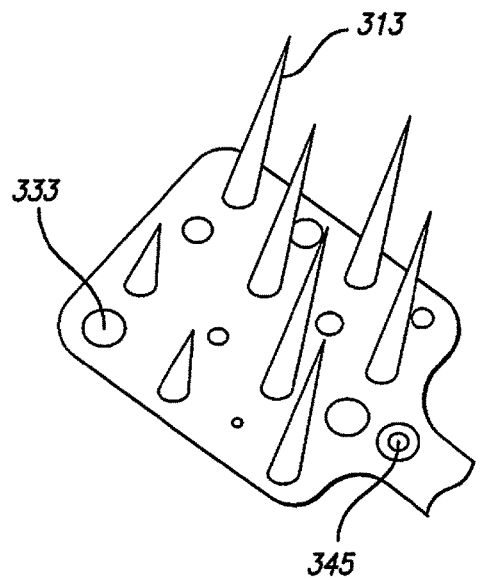

FIG. 68A shows both surface and penetrating electrodes on the same surface of a thin film.

Figure 68B:
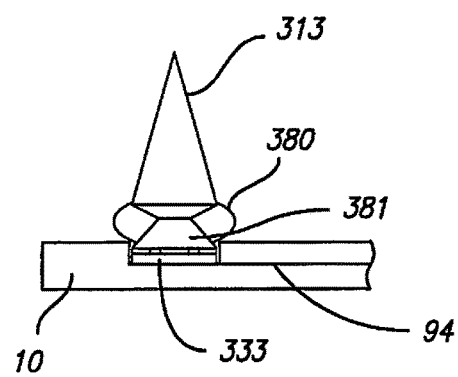

FIG. 68B shows an individual spike electrode attached to a thin film.

Figure 68C:
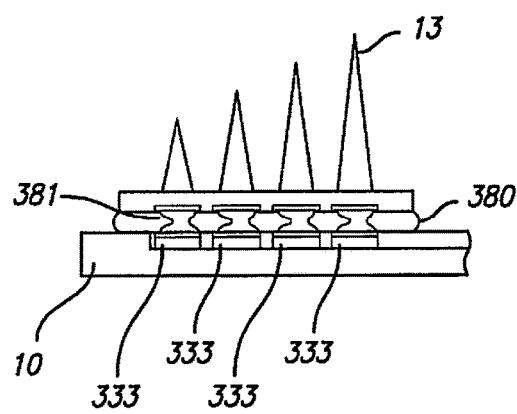

FIG. 68C shows a rigid substrate with spike electrodes attached to a thin film.

Figure 68D:
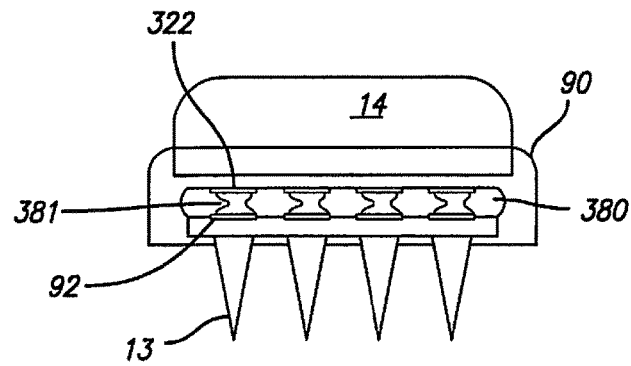

FIG. 68D shows spike electrodes attached directly to an electronics package.

FIGS. 69A-D show a thin film array with electrodes on both sides of the array.

Figure 69A:
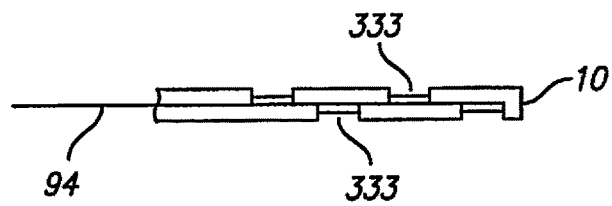

FIG. 69A shows electrodes on either side of a thin film.

Figure 69B:
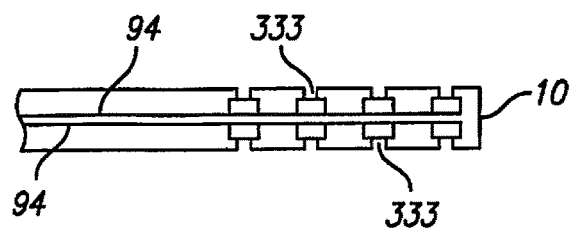

FIG. 69B shows substantially planar electrodes on either side of a thin film.

Figure 69C:
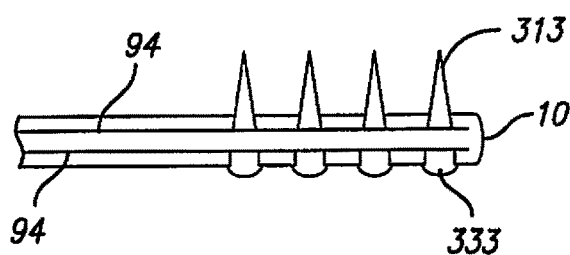

FIG. 69C shows spike electrodes on one side of a thin film and surface electrodes common to the spike electrodes on the other side of the thin film.

Figure 69D:
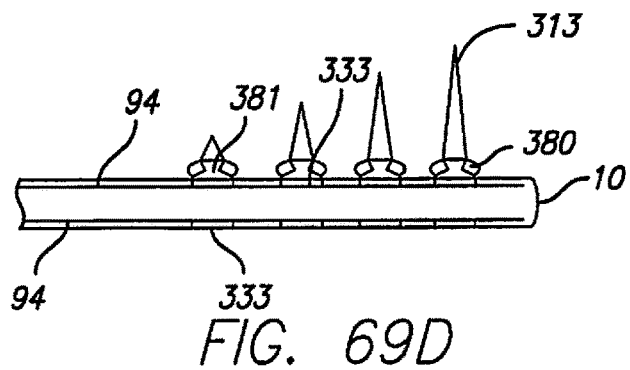

FIG. 69D shows spike electrodes on one side of a thin film and independent surface electrodes on the other side of the thin film.

FIGS. 70A-E show penetrating electrodes individually mounted to a thin film array and insulated penetrating electrodes with openings on their side.

Figure 70A:
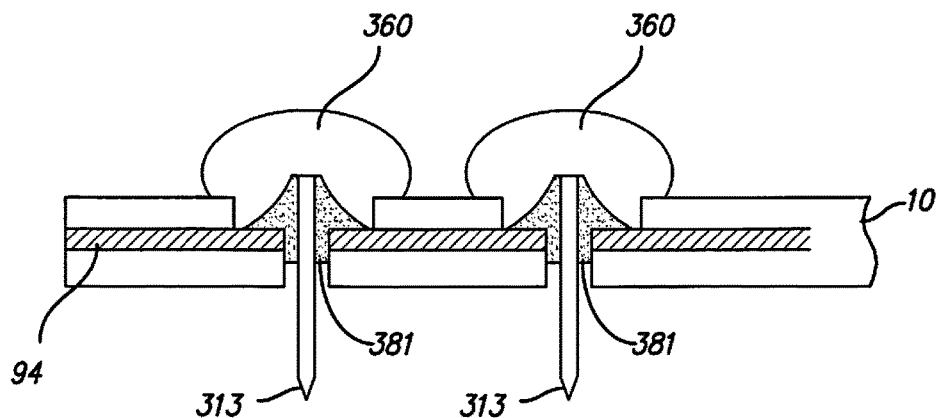

FIG. 70A shows a thin film with spike and nail electrodes.

Figure 70B:
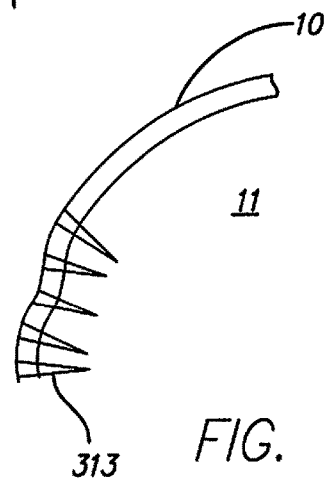

FIG. 70B shows a thin film with penetrating electrodes as curved on the surface of the brain.

Figure 70C:
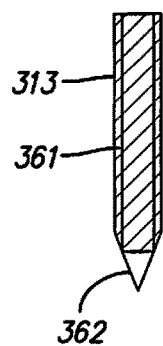

FIG. 70C shows a narrow spike electrode with a passivation layer only open at the tip.

Figure 70D:
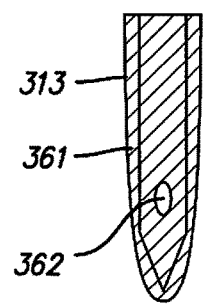

FIG. 70D shows a spike electrode with a passivation layer and a window in the passivation layer for stimulation.

Figure 70E:
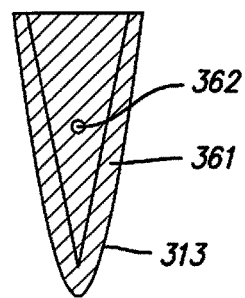

FIG. 70E shows a spike electrode with a passivation layer and a window in the passivation layer for stimulation at the midpoint.

In the following description, like reference numbers are used to identify like elements. Furthermore, the drawings are intended to illustrate major features of exemplary embodiments in a diagrammatic manner. The drawings are not intended to depict every feature of every implementation, nor relative dimensions of the depicted elements, and are not drawn to scale.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

A preferred embodiment of the present invention shown in FIG. 1 consists of an electronics package 14 that is preferably oval or circular in shape (but other shapes are possible), less than 20 mm in diameter (preferably less than 15 mm, and more preferably less than 11 mm in diameter), and that is less than 5 mm in height (preferably less than 4 mm, and more preferably less than 3.5 mm in height), that is mounted on top of the cranium but under the skin. The package may include a feature for mounting to the cranium such as a low profile flange 2 defining holes 3 to accommodate screws (not shown), or tabs 4 that allow screws, sutures, or staples to be taken to fix the package. Attached to and proceeding from the package 14 is a thin film lead 10 to be routed to the tissue to be stimulated or recorded from.

FIG. 2 shows attachment of the package 14 to the cranium 7. Alternatively, the package 14 may be affixed to the cranium through the use of one or more straps, or the package 14 may be glued to the cranium using a reversible or non-reversible adhesive attach. In this embodiment, the package, which protrudes from the cranium, is low profile and shaped in manner that permits the scalp 8 to rest on top of the package with little or no irritation of the scalp. Additionally, edges of the package are preferably rounded, and/or the package 14 may be encased in a soft polymer mold such as silicone to further reduce irritation. In other embodiments, the package 14 may be attached to the scalp 8, brain 11, or dura 12. In embodiments with more than one package, each package may be attached to any of the scalp, cranium, dura, or brain.

The improved package of the present invention allows for miniaturization of the package which is particularly useful in brain stimulators and other prostheses for electrical stimulation of neural tissue.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The electronics package 14 and secondary inductive coil 16 are held together by the molded body 18. The molded body 18 holds the electronics package 14 and secondary inductive coil 16 end to end. This is beneficial as it reduces the height the entire device rises above the sclera. The design of the electronic package (described below) along with a molded body 18 which holds the secondary inductive coil 16 and electronics package 14 in the end to end orientation minimizes the thickness or height above the sclera of the entire device.

The molded body 18 may also include the flange 2 or suture tabs 4. The molded body 18, flange 2, and suture tabs 4 are preferably an integrated unit made of silicone elastomer. Silicone elastomer can be formed in a pre-curved shape to match the curvature of the implantation site. However, silicone remains flexible enough to accommodate implantation and to adapt to variations in the curvature at a particular site. Alternatively, the flange 2 and/or suture tabs 4 may be formed of the same material(s) as the package (that is, integrated with the package), and the molded body 18 can be used to hold the coil 16 and package 18 together.

Figure 3:
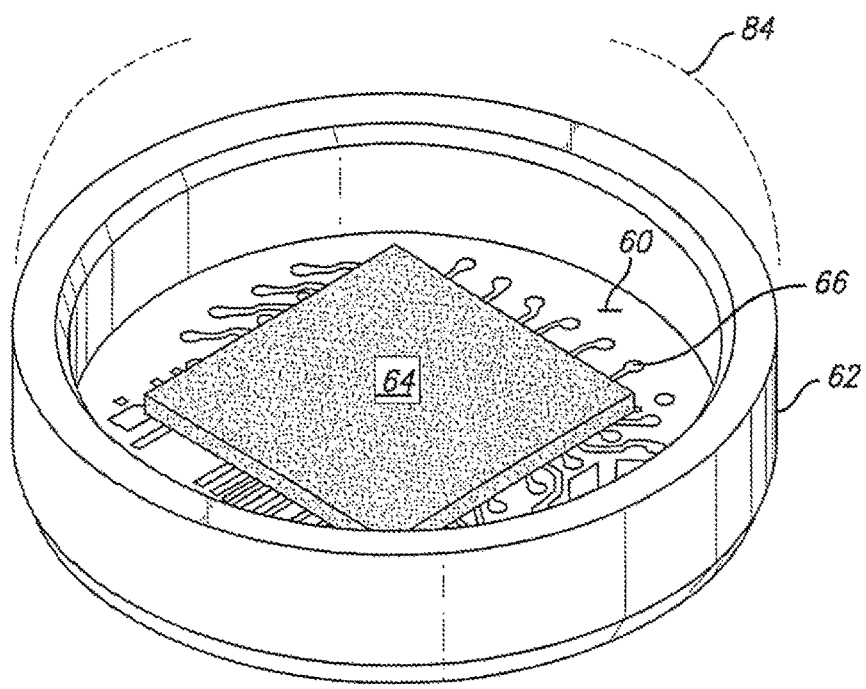
FIG. 3 is a perspective view of a partially built package showing the substrate, chip and the package wall.

Referring to FIG. 3, the hermetic electronics package 14 is composed of a ceramic substrate 60 brazed to a metal case wall 62 which is enclosed by a laser welded metal lid 84. The metal of the wall 62 and metal lid 84 may be any biocompatible metal such as titanium, niobium, platinum, iridium, palladium, or combinations of such metals. The ceramic substrate is preferably alumina but may include other ceramics such as zirconia. The ceramic substrate 60 includes vias (not shown) made from biocompatible metal and a ceramic binder using thick-film techniques. The biocompatible metal and ceramic binder is preferably platinum flakes in a ceramic paste, or frit, which is the ceramic used to make the substrate. After the vias have been filled, the substrate 60 is fired and lapped to thickness. The firing process causes the ceramic to vitrify binding the ceramic of the substrate with the ceramic of the paste forming a hermetic bond.

The package wall 62 is brazed to the ceramic substrate 60 in a vacuum furnace using a biocompatible braze material in the braze joint. Preferably, the braze material is a nickel titanium alloy. The braze temperature is approximately 1000° Celsius. Therefore the vias and thin film metallization 66 must be selected to withstand this temperature. Also, the electronics must be installed after brazing. The chip 64 is installed inside the package using thermo-compression flip-chip technology. The chip is underfilled with epoxy to avoid connection failures due to thermal mismatch or vibration.

Figure 4:
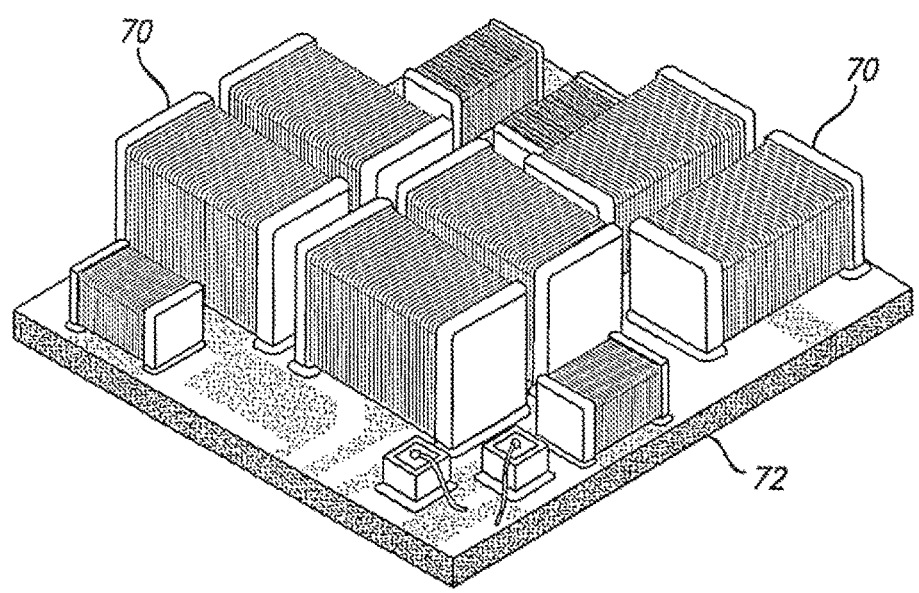
FIG. 4 is a perspective view of the hybrid stack placed on top of the chip.
Figure 5:
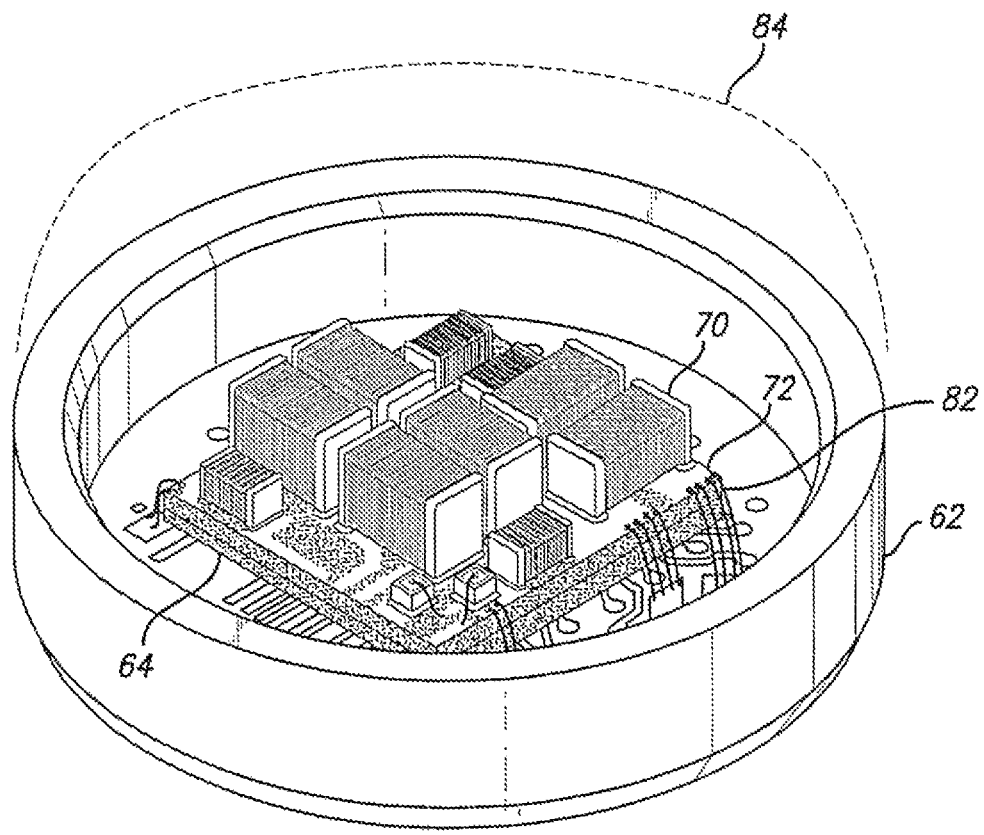
FIG. 5 is a perspective view of the partially built package showing the hybrid stack placed inside.

Referring to FIGS. 4 and 5, off-chip electrical components 70, which may include capacitors, diodes, resistors, or inductors (passives), are installed on a stack substrate 72 attached to the back of the chip 64, and connections between the stack substrate 72 and ceramic substrate 60 are made using gold wire bonds 82. Alternatively, discrete components, or a circuit board, may be attached to the ceramic substrate. A flip-chip integrated circuit and/or hybrid stack is preferred as it minimizes the size of the package 14. The stack substrate 72 is attached to the chip 64 with non-conductive epoxy, and the passives 70 are attached to the stack substrate 72 with conductive epoxy. Thin-film metallization 66 is applied to both the inside and outside surfaces of the ceramic substrate 60 and an ASIC (Application Specific Integrated Circuit) integrated circuit chip 64 is bonded to the thin film metallization on the inside of the ceramic substrate 60.

Figure 6:
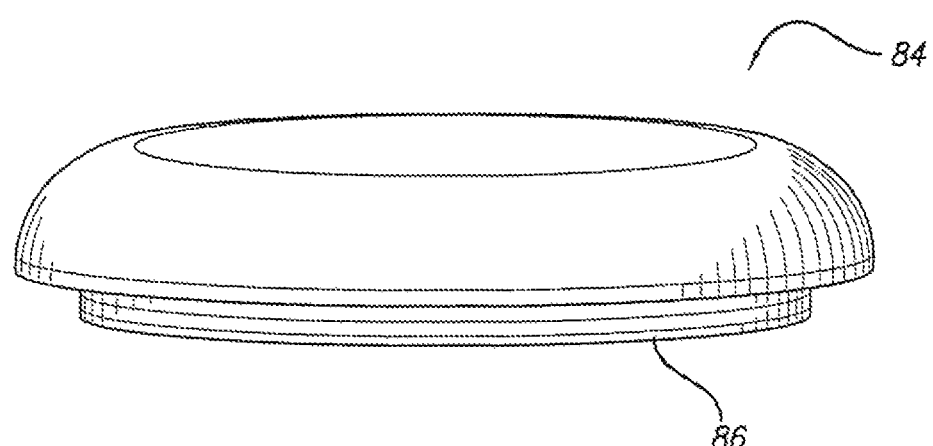
FIG. 6 is a perspective view of the lid to be welded to the top of the package.

Referring to FIG. 6, the electronics package 14 is enclosed by a metal lid 84 that, after a vacuum bake-out to remove volatiles and moisture, is attached using laser welding. A getter (moisture absorbent material) may be added after vacuum bake-out and before laser welding of the metal lid 84. The metal lid 84 further has a metal lip 86 to protect components from the welding process and further insure a good hermetic seal. The entire package is hermetically encased. Hermeticity of the vias, braze, and the entire package is verified throughout the manufacturing process.

The implant secondary inductive coil 16, which provides a means of establishing the inductive link between the external processor (not shown) and the implanted device, preferably consists of gold wire. The wire is insulated with a layer of silicone. The secondary inductive coil 16 may be oval shaped. The conductive wires are wound in defined pitches and curvature shape to satisfy both the electrical functional requirements and the surgical constraints. The secondary inductive coil 16, together with the tuning capacitors in the chip 64, forms a parallel resonant tank that is tuned at the carrier frequency to receive both power and data.

Figure 7:
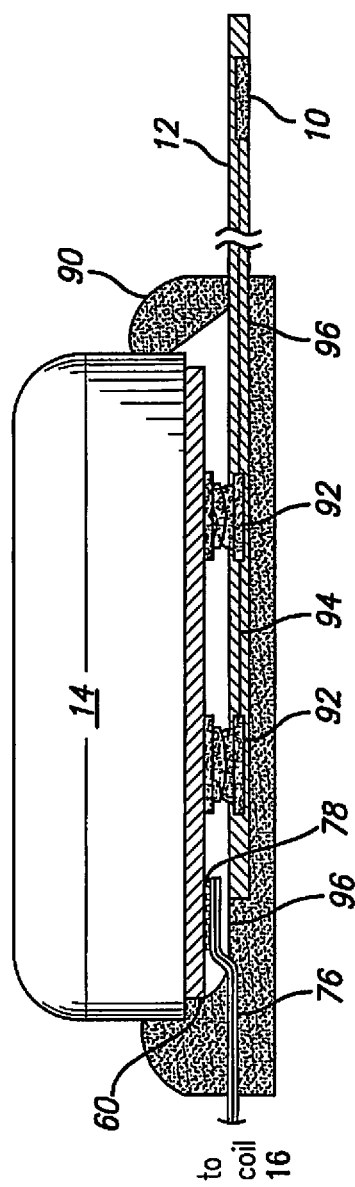
FIG. 7 is a view of the completed package attached to an electrode array.

Referring to FIG. 7, the flexible circuit thin film lead 10, includes platinum conductors 94 insulated from each other and the external environment by a biocompatible dielectric polymer 96, preferably polyimide. One end of the array contains exposed electrode sites that are placed in close proximity to the surface to be stimulated or recorded from 333. The other end contains bond pads 92 that permit electrical connection to the electronics package 14. The electronics package 14 is attached to the flexible circuit 10 using a flip-chip bumping process, and epoxy underfill. In the flip-chip bumping process, bumps containing conductive adhesive placed on bond pads 92 and bumps containing conductive adhesive placed on the electronic package 14 are aligned and cured to build a conductive connection between the bond pads 92 and the electronics package 14. Leads 76 for the secondary inductive coil 16 are attached to gold pads 78 on the ceramic substrate 60 using thermal compression bonding, and are then covered in epoxy. The junction of the secondary inductive coil 16, thin film lead 10, and electronics package 14 are encapsulated with a silicone overmold 90 that connects them together mechanically. When assembled, the hermetic electronics package 14 may sit an arbitrary distance away from the end of the secondary inductive coil.

Since the implant device may be implanted just under the scalp it is possible to irritate or even erode through the scalp. Eroding through the scalp leaves the body open to infection. We can do several things to lessen the likelihood of scalp irritation or erosion. First, it is important to keep the over all thickness of the implant to a minimum. Even though it may be advantageous to mount both the electronics package 14 and the secondary inductive coil 16 on the cranium just under the scalp, the electronics package 14 is mounted higher than, and at a distance laterally displaced from, the secondary inductive coil 16. In other words the thickness of the secondary inductive coil 16 and electronics package should not be cumulative.

It is also advantageous to place protective material between the implant device and the scalp. The protective material can be provided as a flap attached to the implant device or a separate piece placed by the surgeon at the time of implantation. Adding material over the device will promote healing and sealing of the wound. Suitable materials include Dacron, Teflon (polytetraflouroethylene or PTFE), Goretex (ePTFE), Tutoplast (sterilized sclera), other processed tissue, Mersilene (Polyester), or silicone.

Figure 8:
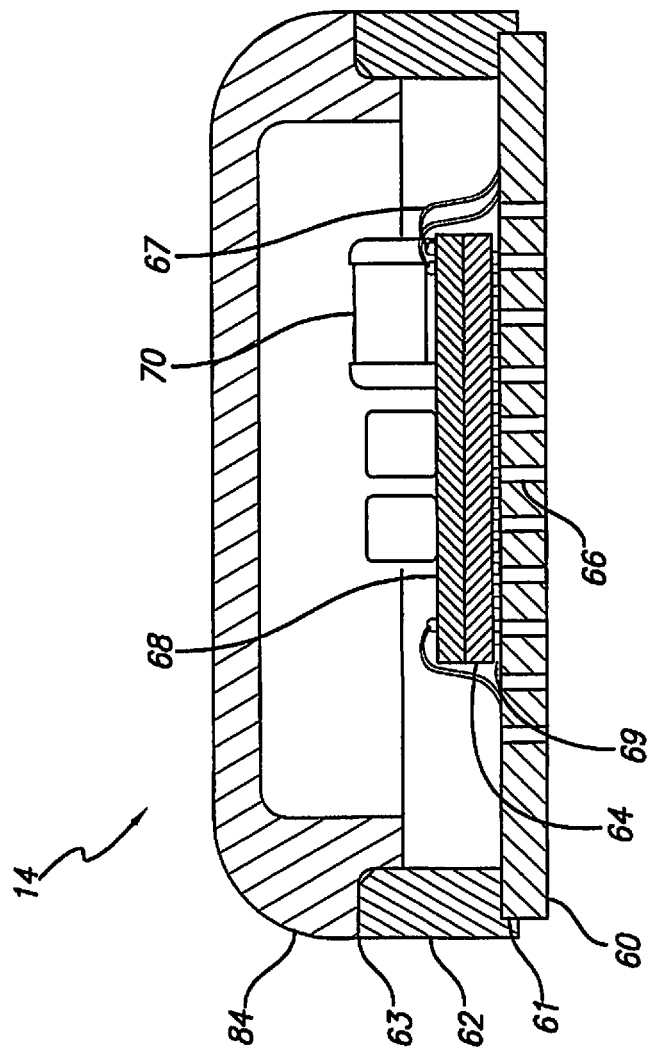
FIG. 8 is a cross-section of the package.

Referring to FIG. 8, the package 14 contains a ceramic substrate 60, with metallized vias 65 and thin-film metallization 66. The package 14 contains a metal case wall 62 which is connected to the ceramic substrate 60 by braze joint 61. On the ceramic substrate 60 an underfill 69 is applied. On the underfill 69 an integrated circuit chip 64 is positioned. On the integrated circuit chip 64 a ceramic hybrid substrate 68 is positioned. On the ceramic hybrid substrate 68 passives 70 are placed. Wirebonds 67 are leading from the ceramic substrate 60 to the ceramic hybrid substrate 68. A metal lid 84 is connected to the metal case wall 62 by laser welded joint 63 whereby the package 14 is sealed.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The electronics package 14 and secondary inductive coil 16 are held together by the molded body 18. The molded body 18 holds the electronics package 14 and secondary inductive coil 16 end to end. The secondary inductive coil 16 is placed around the electronics package 14 in the molded body 18. The molded body 18 holds the secondary inductive coil 16 and electronics package 14 in the end to end orientation and minimizes the thickness or height above the sclera of the entire device.

Figure 9:
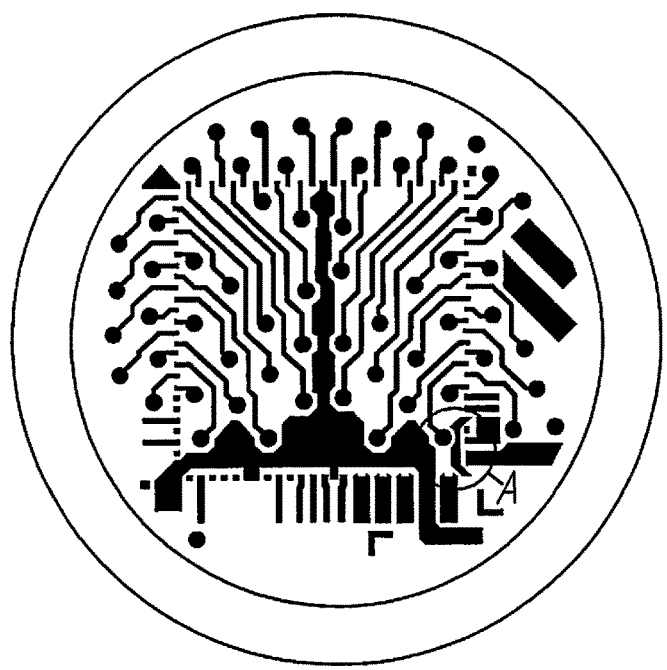
FIG. 9 is a top view of the ceramic substrate showing the metal traces for redirecting electrical connections.
Figure 10A:
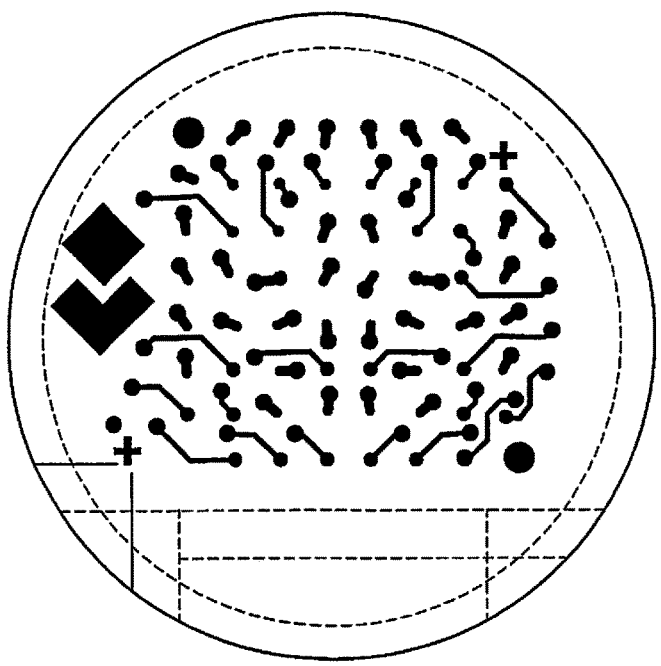
FIG. 10A is a bottom view of the ceramic substrate showing the metal traces for redirecting electrical connections.

Referring to FIGS. 9 and 10, thin-film metallization 66 is applied to both the inside and outside surfaces of the ceramic substrate 60 and an ASIC (Application Specific Integrated Circuit) integrated circuit chip 64 is bonded to the thin film metallization on the inside of the ceramic substrate 60.

The inside thin film metallization 66 includes a gold layer to allow electrical connection using wire bonding. The inside film metallization includes preferably two to three layers with a preferred gold top layer. The next layer to the ceramic is a titanium or tantalum or mixture or alloy thereof. The next layer is preferably a palladium or platinum layer or an alloy thereof. All these metals are biocompatible. The preferred metallization includes a titanium, palladium, and gold layer. Gold is a preferred top layer because it is corrosion resistant and can be cold bonded with gold wire. The outside thin film metallization includes a titanium adhesion layer and a platinum layer for connection to platinum electrode array traces. Platinum can be substituted by palladium or a palladium/platinum alloy. If gold-gold wire bonding is desired a gold top layer is applied.

The three layer stack of metallization consists of an adhesion layer, a barrier layer, and a bonding layer. The adhesion layer is a metal best suited to bond with the ceramic. Titanium is good adhesion layer material. Titanium is active enough to bond with ceramics, but still noble enough to be bio-compatible. Alternative adhesion layers are chromium or tungsten. Both bond better, but are less biocompatible. A non-biocompatible adhesion layer may be used if it is adequately isolated from the body.

The center layer is a barrier layer. The preferred barrier layer for external traces is platinum, while palladium is the preferred barrier layer for internal traces. The barrier layer prevents, or reduces migration of the adhesion layer and bonding layer due to heat from the brazing process. Migration of the layers reduces the effectiveness of each layer. Other possible barrier layers are ruthenium, rhodium, molybdenum, or iridium. All of these materials are rare and expensive. Iridium is the only one that is reasonably biocompatible.

The top layer is the bonding layer for bonding electrical connections. Gold is the preferred bonding layer. On the inside metallization, electrical circuits are flip-chip bonded, or wire-bonded to the gold bonding layer. On the outside, the coil 16 is compression bonded to the gold bonding layer. Alternatively, a thermo-compression process may be used. The electrode array cable is attached through a platinum epoxy paste. In this case, a gold bonding layer is counterproductive. Since the barrier layer is platinum, the gold bonding layer is etched from the array bond pads, allowing for a platinum to platinum bond.

Preferably, the layers are sputtered on the ceramic with the adhesion layer 500 to 1000 angstrom, the barrier layer 5000 angstrom, and the bonding layer 2000 angstrom. The traces are patterned with photo-resist and wet etched with potassium iodide. Additionally, the bonding layer may be electroplated to ten microns for a better bonding surface. Alternatively, a lift off process may be used. If a lift off process is used, care must be taken to completely clean the photoresist from trace areas to provide for good adhesion. The metallization includes capture pads to improve alignment with the vias.

It should also be noted that the thin film metalization 66 includes a single ring 67 completely around the interior or top surface of the substrate 60. When brazing, it is common for braze material to flow further than desired, which is called braze run out. A single ring around the circumference of the substrate 60, sputtered and patterned as part of the thin film metallization, provides a dam to prevent braze run out from contacting and shorting the traces used for electrical redirection.

Figure 10B:
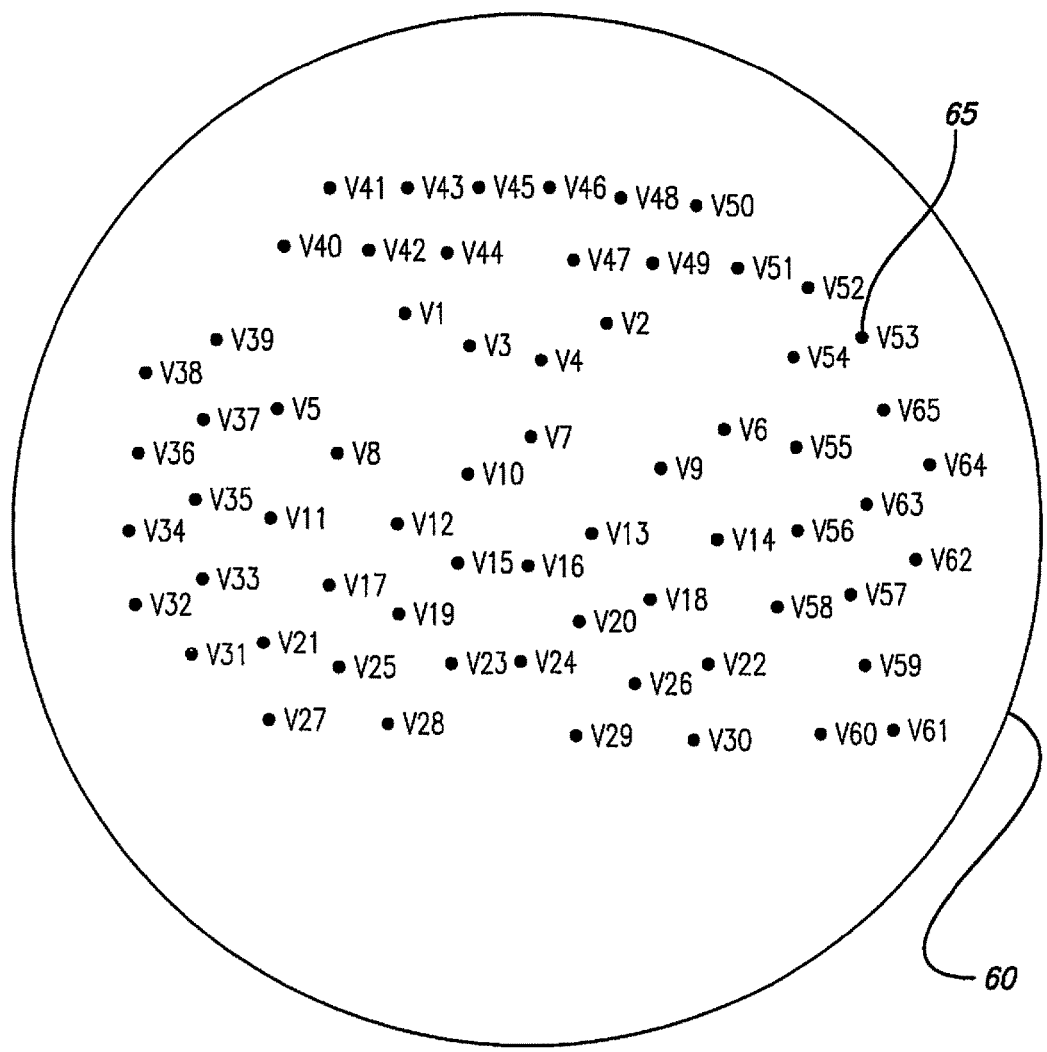
FIG. 10B is a bottom view of the ceramic substrate prior to metallization showing the vias through the substrate.

FIG. 10B shows the locations of the vias or feedthroughs 65 on the substrate 60 prior to sputtering the thin film metallization 66. The following discussion is directed to a method and apparatus suitable for forming hermetic electrical vias or feedthroughs in a ceramic sheet (or substrate) having a possible thickness of ≤40 mils, for the construction of the substrate 60, with metallized vias (feedthroughs) 65. The metallization includes capture pad to improve alignment with the vias.

Electrical feedthroughs in accordance with the present writing are intended to function in corrosive environments, e.g., in medical devices intended for implantation in a patient's body. In such applications, it is generally critical that the device housing be hermetically sealed which, of course, requires that all feedthroughs in the housing wall also be hermetic. In such applications, it is also generally desirable that the weight and size of the housing be minimized and that all exposed areas of the housing be biocompatible and electrochemically stable. Biocompatibility assures that the implanted device has no deleterious effect on body tissue. Electrochemical stability assures that the corrosive environment of the body has no deleterious effect on the device. Ceramic and platinum materials are often used in implantable medical devices because they typically exhibit both biocompatibility and electrochemical stability.

Embodiments constructed in accordance with the present disclosure are able to achieve very high feedthrough density. For example, in applications where miniaturization is important, the feedthrough pitch, i.e., center-to-center distance between adjacent feedthroughs, may be from 10 mils to 40 mils.

Figure 11:
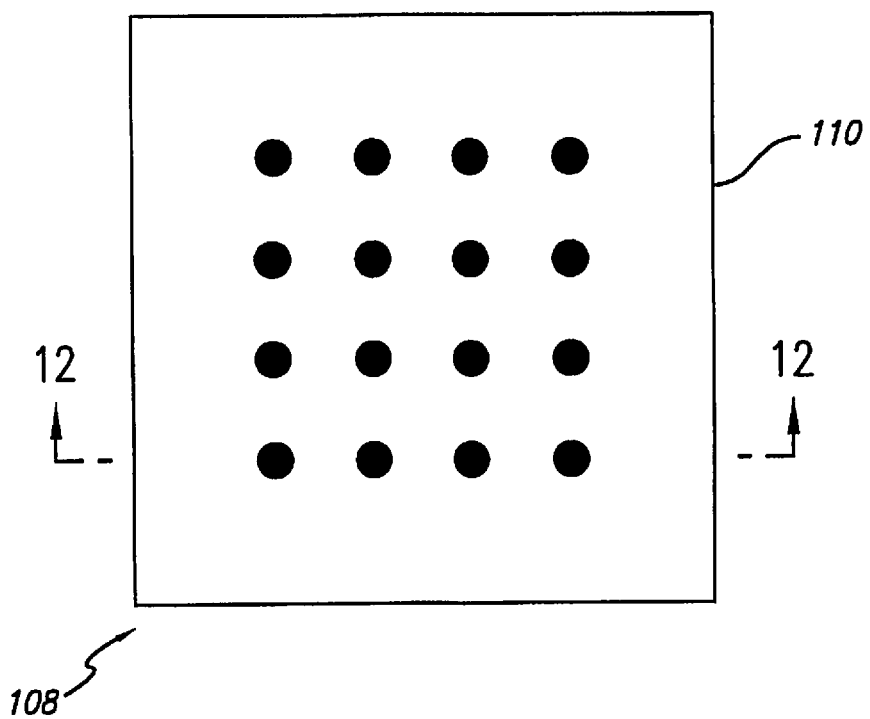
FIG. 11 depicts a top view of a finished feedthrough assembly in accordance with the present disclosure comprised of a ceramic sheet having electrically conductive vias extending therethrough.
Figure 12:
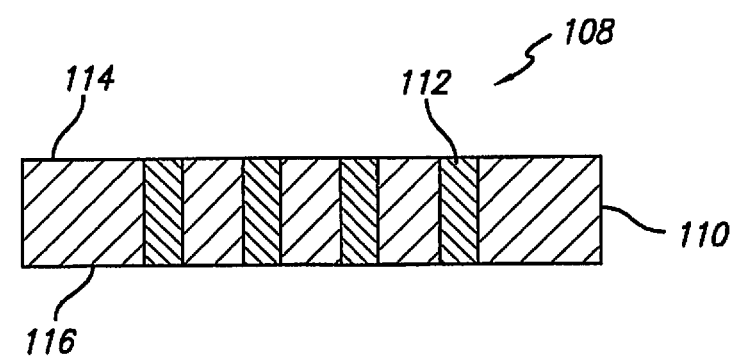
FIG. 12 depicts a sectional view taken substantially along the plane 2-2 of FIG. 11 showing the electrically conductive vias ends flush with the surfaces of the ceramic sheet.

Attention is initially directed to FIGS. 11 and 12 which depict a preferred feedthrough assembly 108 in accordance with the present disclosure comprising a thin ceramic sheet 110 of ceramic material having multiple electrical feedthroughs 112 extending therethrough, terminating flush with the upper and lower surfaces 114, and 116 of sheet 100. The sheet 100 typically comprises a wall (floor?) portion of a housing (not shown) for accommodating electronic circuitry. The feedthroughs 112 function to electrically connect devices external to the housing, e.g., adjacent to surface 114, to electronic circuitry contained within the housing, e.g., adjacent to surface 116. "Thin ceramic sheet" as used herein refers to a sheet having a finished thickness dimension of ≤40 mils, i.e., 1 mm. The apparatus in accordance with the disclosure is particularly suited for use in corrosive environments such as in medical devices implanted in a patient's body.

The present disclosure is directed to providing electrical feedthroughs that are compatible with thin ceramic sheets (or substrates) having a finished thickness of ≤40 mils, and with feedthroughs that are hermetic, biocompatible, and electrochemically stable. In one exemplary embodiment, the ceramic sheet 110 may be formed of 90% aluminum oxide ($AlO_2$) and the feedthroughs 112 may have a diameter of ≤20 mils and may be composed of paste containing, for example, platinum.

Attention is now directed to FIGS. 13 and 14A-14M which depict the possible process steps for fabricating the finished feedthrough assembly 108 illustrated in FIGS. 11 and 12.

Figure 13:
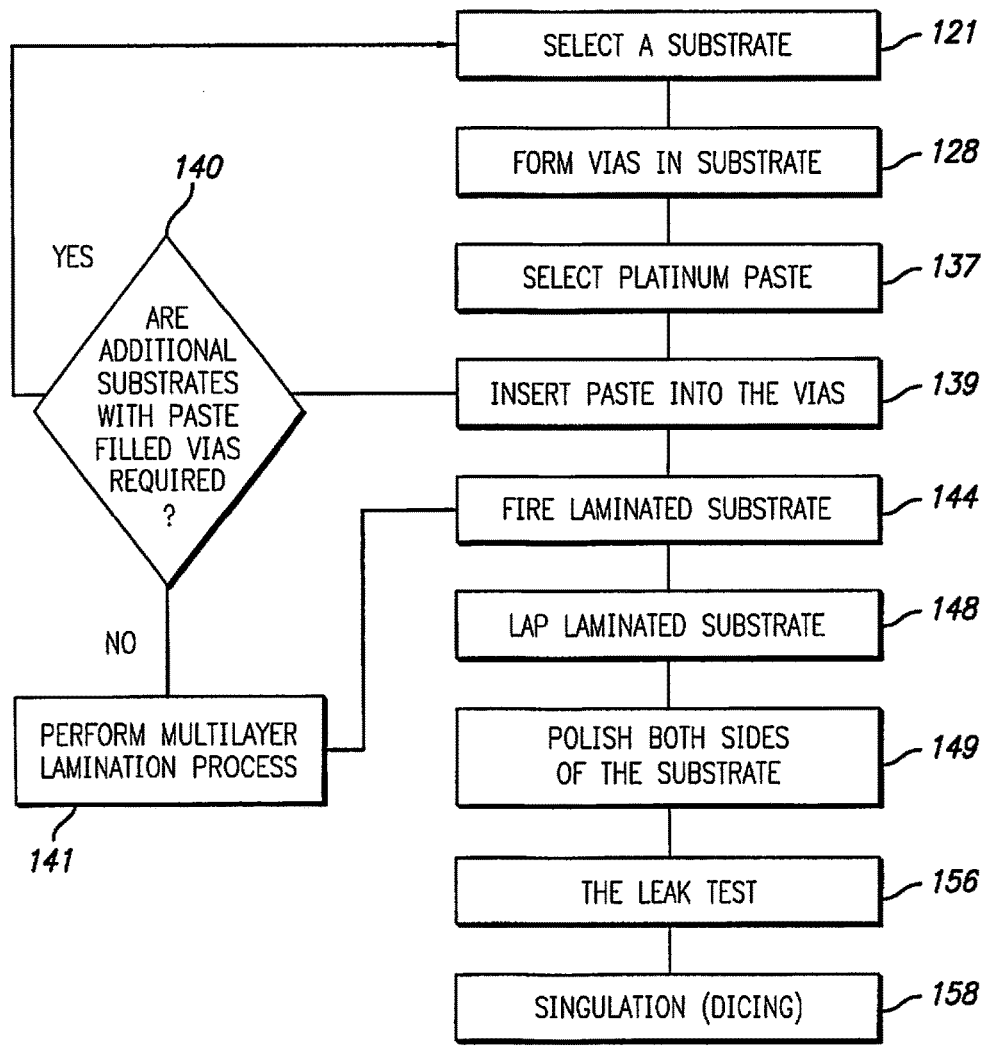
FIG. 13 depicts a flow diagram illustrating a possible series of process steps for fabricating a feedthrough assembly in accordance with the present disclosure.

Initially, a green ceramic sheet/tape/substrate 120 (FIG. 14A), formed, for example, of >90% aluminum oxide ($AlO_2$), is selected as represented by step 121 in FIG. 13. In an exemplary embodiment, the sheet 120 may have a thickness of 40 mils or less. "Green ceramic sheet/tape/substrate" as used herein refers to an unfired ceramic sheet, tape or substrate.

Via holes 126 are formed into the sheet 120 as represented by FIGS. 14B-14C and step 128 in FIG. 13. In an exemplary embodiment, each via hole 126 may be punched in to the sheet 120 using, for example, a programmable punch tool 127. In one exemplary embodiment, a plurality of via holes 126 may be punched at the same time. It is to be understood that other methods may be used to form via holes 126. For Example, via holes 126 may be formed using solvent etching, laser ablation, and/or via holes 126 may be drilled.

Step 137 of FIG. 13 calls for selecting a conductive thick-film paste 117 to fill in via holes 126 depicted in FIG. 14C. "Thick-film paste" as used herein refers to a material containing inorganic particles dispersed in a vehicle comprising an organic resin and a solvent. Types of different pastes are disclosed in U.S. Pat. No. 5,601,638, the disclosure of which is incorporated herein by reference.

In one exemplary embodiment, a stencil printing with vacuum pull down process may be used to fill via holes 126 with the conductive paste 117 as represented by FIGS. 14D-14E and step 139 in FIG. 13. During the stencil printing with vacuum pull down process, the sheet 120 may be sandwiched between a stencil layer 119 and a vacuum base 180. As a squeegee 118 rolls the conductive paste 117 across the stencil layer 119, a vacuum chuck 181 of the vacuum base 180 pulls the conductive paste 117 through holes 182 of the stencil layer 119 and into the via holes 126 as shown in FIGS. 14D-14E.

Step 140 of FIG. 13 calls for determining if additional green ceramic sheet/tape/substrates with paste filled via holes are required. If additional green ceramic sheet/tape/ substrates with paste filled via holes are required ("Yes" in step 40), steps 121, 128, 137 and 139 are repeated. If additional green ceramic sheet/tape/substrates with paste filled via holes are not required ("No" in step 140), step 141 of FIG. 13 is performed.

Figure 14F:
Figure 14H:
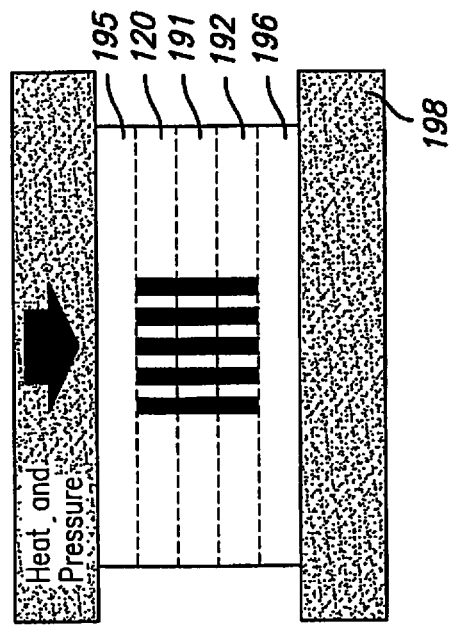
Figure 14G:
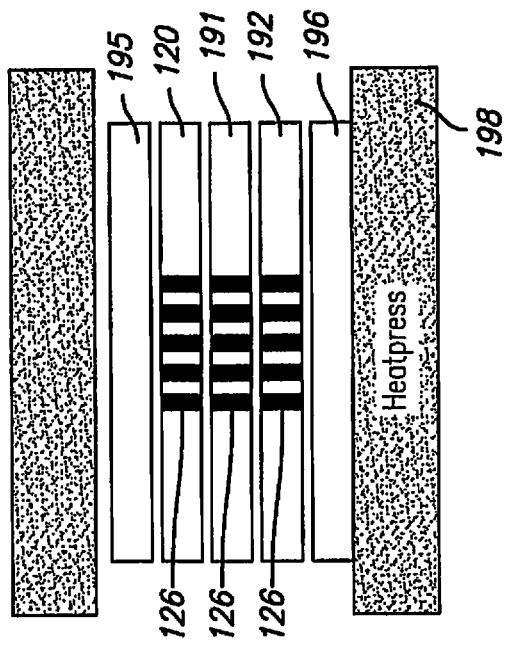

Upon completion of the stencil printing with vacuum pull down process and step 140, the sheet 120 with via holes 126 filled with conductive paste 17 shown in FIG. 14F may go through a multilayer lamination process as represented by FIGS. 14G-14H and step 141 in FIG. 13.

In the multilayer lamination process, the sheet 120 of FIG. 14F may be laminated with, for example, sheets 191 and 192 as shown in FIG. 14G. The sheets 191 and 192 may contain conductive paste filled vias 126 that are similar to the conductive paste filled vias 26 of the sheet 120 and the sheets 191 and 192 may be formed using steps 121, 128, 137 and 139 of FIG. 13 as described above.

Figure 14I:
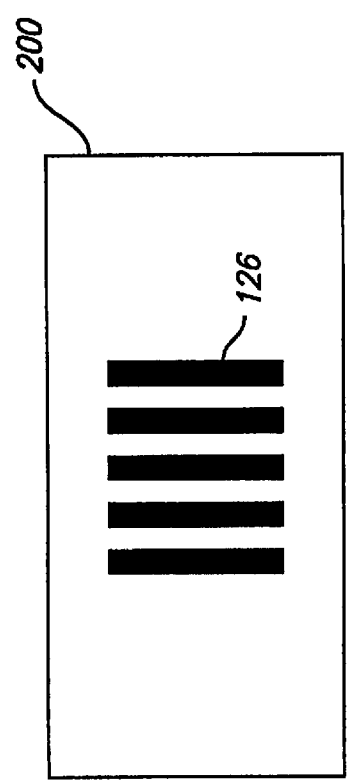

During the multilayer lamination process, a) the sheets 120, 191 and 192 are stacked on top of each other with conductive paste filled vias 126 of each sheet being aligned on top of each other; b) stacked sheets 120, 191 and 192 are sandwiched between two unpunched green ceramic sheets/ tapes/substrates 195 and 196; and c) the sheets 120, 191 and 192 and the sheets 195 and 196 are laminated together using a heat press 198 to create the laminated substrate 200 shown in FIG. 14I.

Although FIGS. 14G and 14H laminate three sheets 120, 191 and 192 with conductive paste filled vias 126, one skilled in the art can appreciate that this disclosure is not limited to three sheets and that a single sheet 120 with conductive paste filled vias may be laminated together with the sheets 195 and 196 without the additional sheets 191 and 192. Although FIGS. 14G and 14H laminate three sheets 120, 191 and 192 with conductive paste filled vias 126, one skilled in the art can appreciate that this disclosure is not limited to three sheets and that additional sheets with conductive paste filled vias may also be laminated together with sheets 120, 191 and 192.

Step 144 of FIG. 13 calls for the laminated substrate 200 to be fired. Firing of the laminated substrate 200 encompasses different aspects of forming bonds in ceramic (evaporation, binder burnout, sintering, etc.). The unpunched ceramic layers 195 and 196 of the laminated substrate 200 help to constrain the conductive paste within via holes 126 and allow for compression during the firing step 144. The unpunched ceramic layers 195 and 196 of the laminated substrate 200 also help to isolate the conductive paste filled vias 126 from the firing atmosphere during the step 144 which may be the key to hermetic and low resistance paste filled vias 126. An exemplary firing schedule includes ramping the laminated substrate 200 of FIG. 14I up to 600° C. at a rate of 1° C./minute, then ramping up to 1600° C. at a rate at 5° C./minute, followed by a one hour dwell and then a cool-to-room-temperature interval.

During the firing and subsequent cooling during the step 144, the ceramic material of the laminated substrate 200 shrinks thereby shrinking via holes 126 around the paste 117 to form a seal. The fine aluminum oxide suspension permits uniform and continuous sealing around the surface of the paste 117. Additionally, at the maximum firing temperature, e.g., 1600° C., the paste 117 being squeezed by the ceramic exhibits sufficient flow to enable the paste 117 to flow and fill any crevices in the ceramic. This action produces a hermetic paste/ceramic interface. Furthermore, the firing step 144 may also cause hermeticity through bonding mechanisms like, for example, sintering, glass melt/wetting, alloying, compounding, and/or diffusion solution formation. "Sintering" as used herein is a term used to describe the consolidation of the ceramic material during firing. Consolidation implies that within the ceramic material, particles have joined together into an aggregate that has strength. The term sintering may be used to imply that shrinkage and densification have occurred; although this commonly happens, densification may not always occur. "Sintering" is also a method for making objects from powder, by heating the material (below its melting point) until its particles adhere to each other. "Sintering" is traditionally used for manufacturing ceramic objects, and has also found uses in such fields as powder metallurgy. "Alloying" as used herein refers to an alloy that is a homogeneous hybrid of two or more elements, at least one of which is a metal, and where the resulting material has metallic properties. "Compounding" as used herein refers to a chemical compound that is a substance consisting of two or more elements chemically-bonded together in a fixed proportion by mass. "Diffusion solution formation" as used herein refers is the net movement of particles from an area of high concentration to an area of low concentration. A solid solution is a solid-state solution of one or more solutes in a solvent. Such a mixture is considered a solution rather than a compound when the crystal structure of the solvent remains unchanged by addition of the solutes, and when the mixture remains in a single homogeneous phase. Also, the firing step 144 may also cause solidification of the metalized vias 126 and the ceramic material of the laminated substrate 200 to prevent leaks.

Figure 14J:
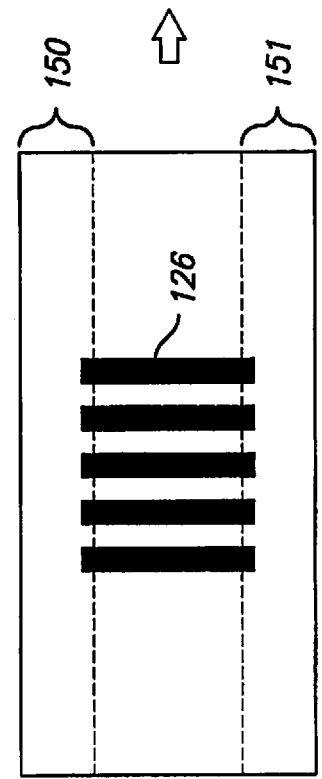
Figure 14K:
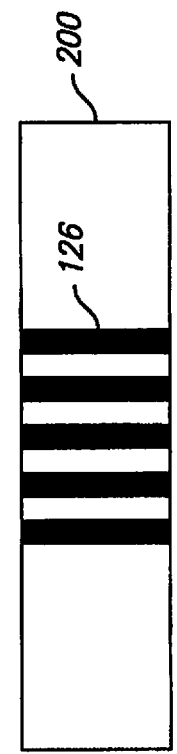

Step 148 of FIG. 13 calls for lapping or grinding the upper and lower surfaces of the fired laminated substrate 200 to remove materials 150 and 151, depicted in FIG. 14J, in order to expose the upper and lower faces of the metalized vias 126. The upper and lower surfaces of the fired laminated substrate 200 may also go through the polishing step 149 so that the metalized vias 126 are flush with the surrounding ceramic material.

After lapping and/or grinding, the fired laminated substrate 200 may be subjected to a hermeticity test, e.g., frequently a helium (He) leak test as represented by step 156 in FIG. 13.

Figure 14L:
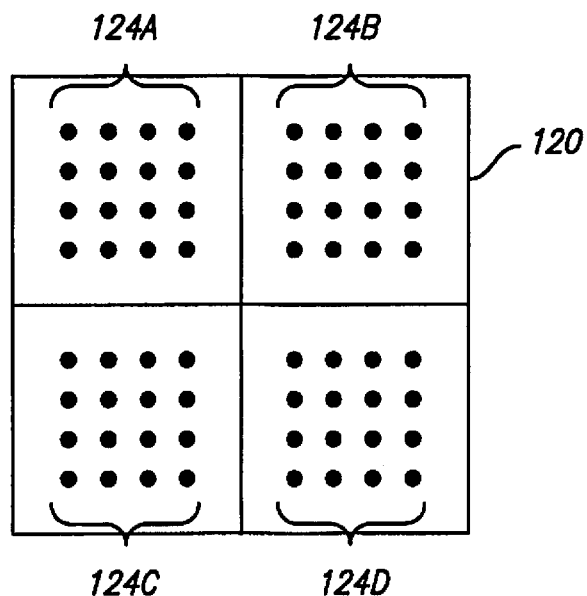
Figure 14M:
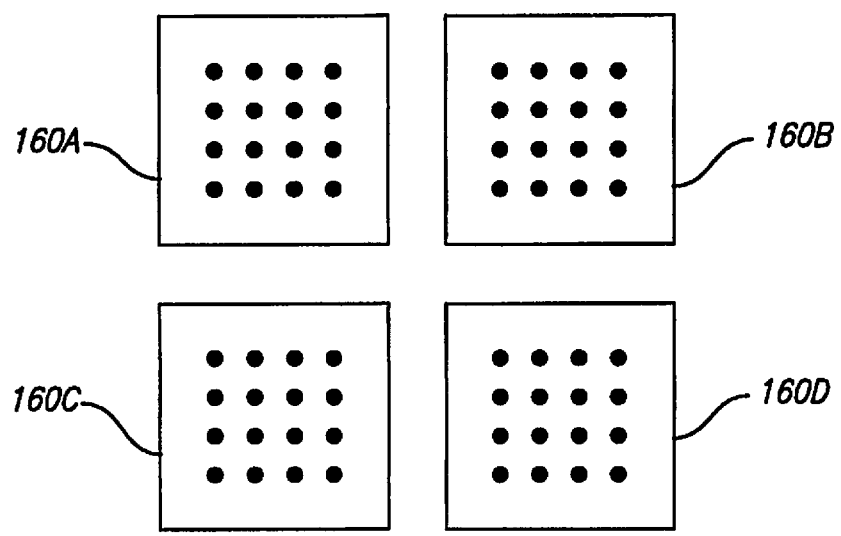

In one exemplary embodiment, sheet/substrate 120 may contain several patterns 124A-D of the via holes 126 as shown in FIG. 14L. In this exemplary embodiment, the fired laminated substrate 200 would contain several patterns 124A-D of the metal filled via holes 126 and the fired laminated substrate 200 would be subjected to a singulation or dicing step 158 to provide multiple feedthrough assemblies 160A, 160B, 160C, 160D shown in FIG. 14M.

Although some embodiments described above employ a ceramic sheet of >90% aluminum oxide ($AlO_2$), alternative embodiments may use other ceramic materials, e.g., zirconium. Because the firing temperature of the ceramic can be tailored within certain limits, the conductive paste 17 may comprise any of the noble metals and/or any of the refractory metals, for example, platinum, titanium, gold, palladium, tantalum, niobium.

The package of the present invention can applied to many uses in the medical device industry. In addition to a visual prosthesis, applications for the package of the present invention include cochlear stimulation, spinal cord stimulation, glucose sensing, and brain surface and deep brain stimulation.

Figure 2A:
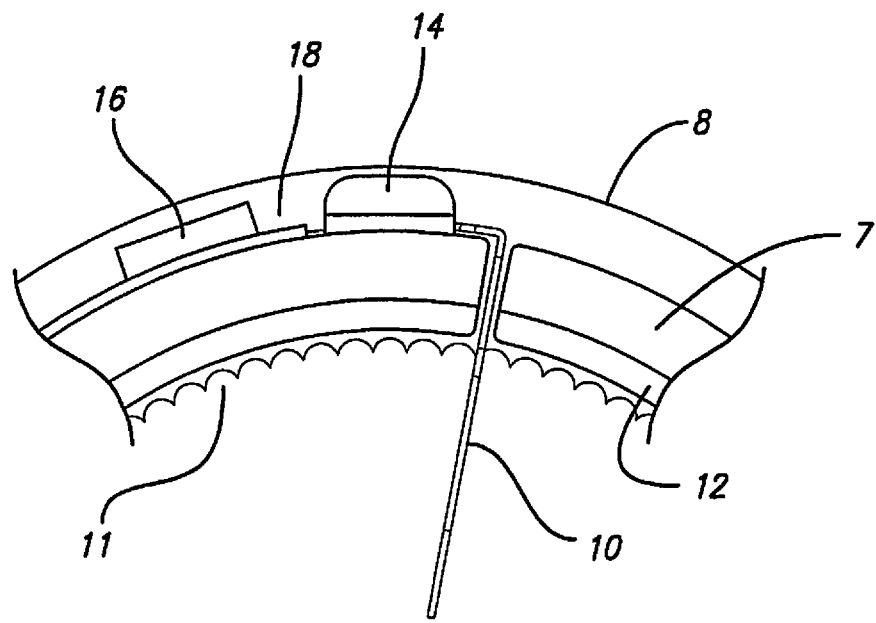
FIG. 2A Shows the preferred invention as implanted for deep brain stimulation.
Figure 2B:
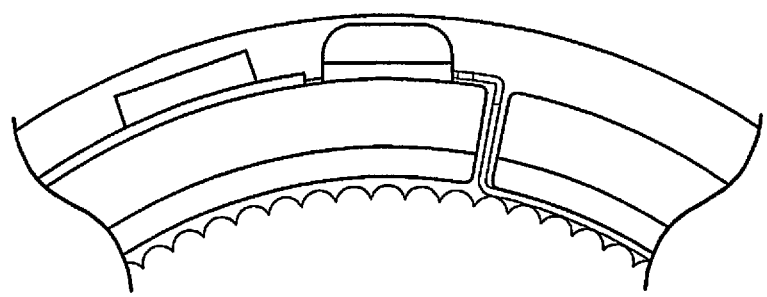
FIG. 2B Shows an alternate implantation location for brain surface stimulation.
Figure 15:
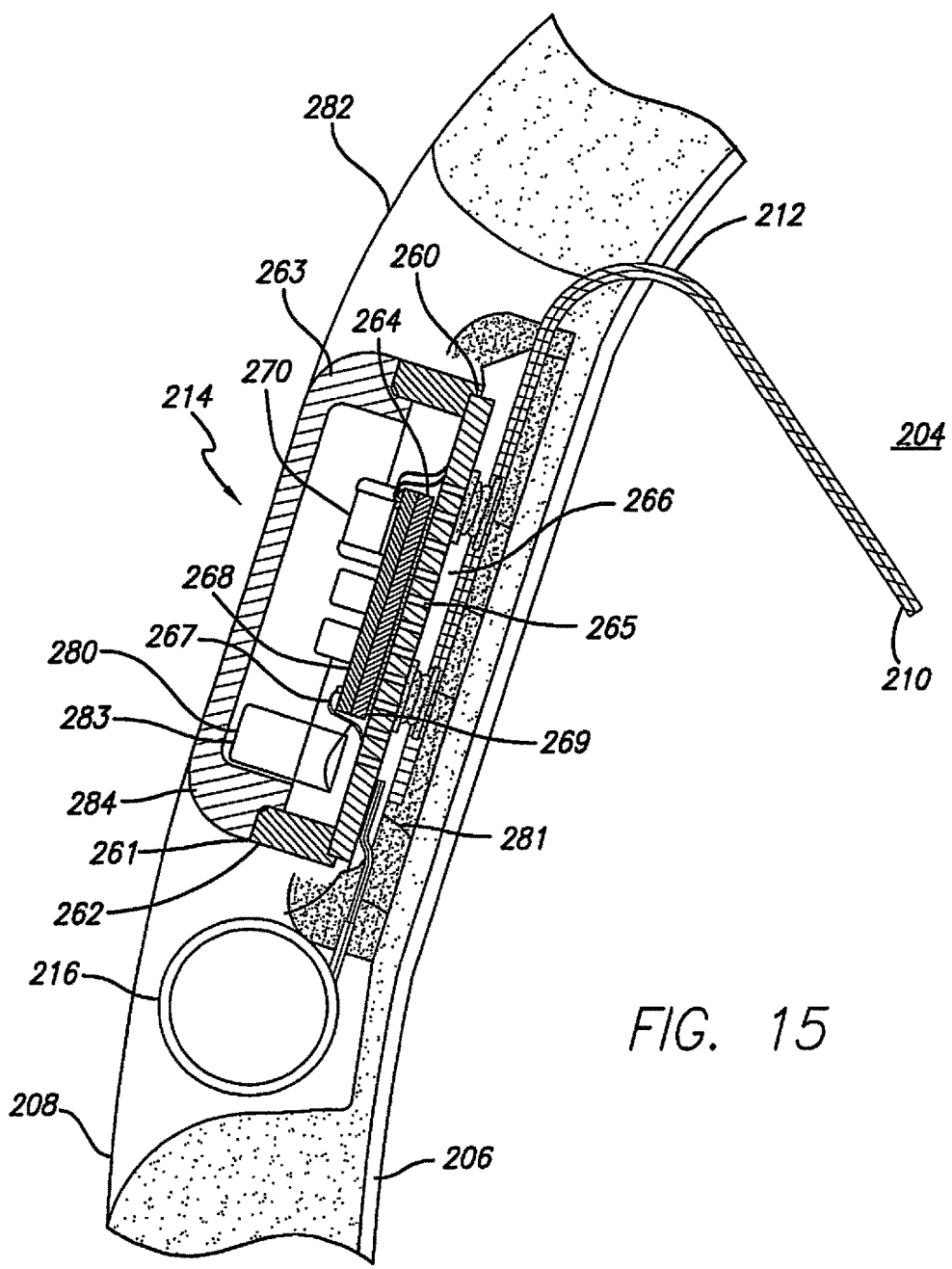
FIG. 15 shows the preferred implantation of the preferred invention in the brain.
Figure 16A:
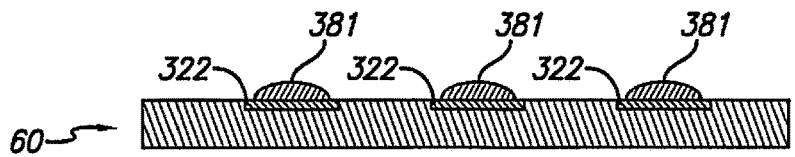
FIGS. 16A-E show the method of attaching a thin film array to the electronics package.
Figure 16B:
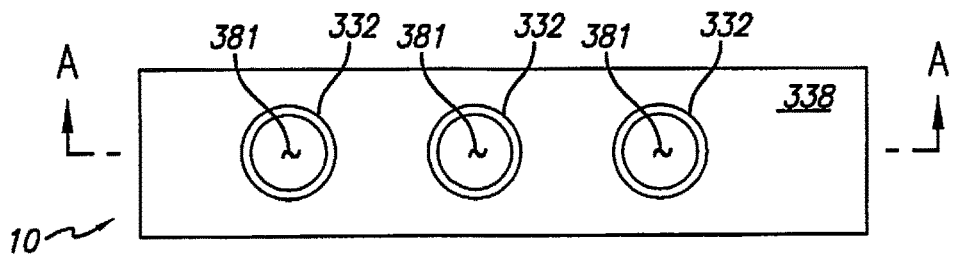
Figure 16C:
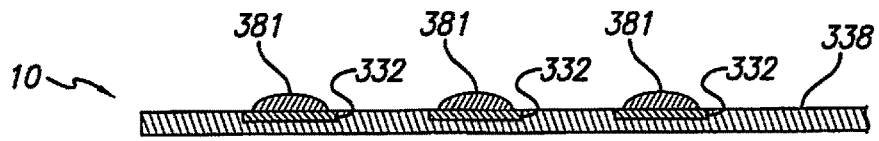
Figure 16D:
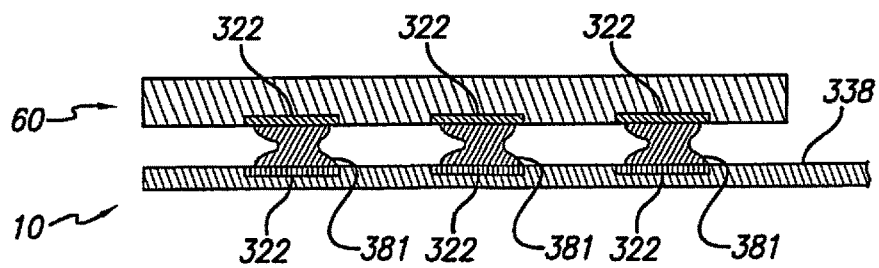
Figure 16E:
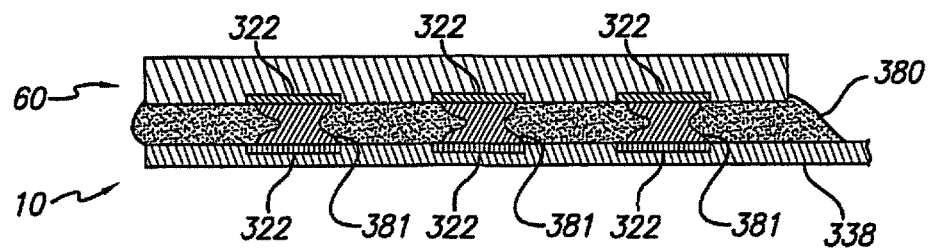

FIG. 15, shows application of the package of the present invention to deep brain stimulation, as shown in FIG. 2A, but in further detail. Due to the low profile of the package, the package 214 can be implanted in a hollowed out portion of the cranium 208. The hollowed out portion may go part way through the cranium 208, leaving part of the bone under the package 214. Alternatively, the hollowed out portion may extend through the cranium and the package 214 rests on the dura 206. This protects the package 214, allows the package 214 to be placed close to the stimulation site, and avoids visible protrusions on the head. The package 214 contains a ceramic substrate 260, with metallized vias 265 and thin-film metallization 266. The package 214 contains a metal case wall 262 which is connected to the ceramic substrate 260 by a braze joint 261. On the ceramic substrate 260 an underfill 269 is applied. On the underfill 269 an integrated circuit chip 264 is positioned. On the integrated circuit chip 264 a ceramic hybrid substrate 268 is positioned. On the ceramic hybrid substrate 268 passives 270 are placed. Wire bonds 267 are leading from the ceramic substrate 260 to the ceramic hybrid substrate 268. A metal lid 284 is connected to the metal case wall 262 by laser welded joint 263 whereby the package 214 is sealed. In addition, a rechargeable battery 280 is placed within the package 214 to allow the deep brain stimulator to operate without external power. A thin film array cable 212 leads to an electrode array 210 for stimulation of brain tissue 204. A coil 216 is placed close to the scalp to receive inductive power and data from an external coil (not shown) to program the electronics and recharge the battery 280.

Also, a cover 282 such as Dacron mesh may be used to hold the package 216 in place. The cover 282 may be glued or screwed to the cranium. It should be noted that the package 214 is placed with the delicate ceramic substrate 260 protected with the more durable metal-lid 284 just beneath the scalp.

FIG. 16 shows the preferred method of bonding the substrate 60 to the flexible thin film lead 10 using electrically conductive adhesive 381, such as a polymer, which may include polystyrene, epoxy, or polyimide, which contains electrically conductive particulate of select biocompatible metal, such as platinum, iridium, titanium, platinum alloys, iridium alloys, or titanium alloys in dust, flake, or powder form.

In FIG. 16, step a, the substrate 60, and the input/output contacts 322 are prepared for bonding by placing conductive adhesive 381 on the input/output contacts 322, at the ends of the thin film metallization trace 66. In step b, the flexible thin film lead 10 is preferably prepared for bonding to the substrate 60 by placing conductive adhesive 381 on bond pads 332. Alternatively, the adhesive 381 may be coated with an electrically conductive biocompatible metal. The flexible thin film lead 10 contains the flexible electrically insulating substrate 338, which is preferably comprised of polyimide. The bond pads 332 are preferably comprised of an electrically conductive material that is biocompatible when implanted in living tissue, and are preferably platinum or a platinum alloy, such as platinum-iridium.

FIG. 16, step c illustrates the cross-sectional view A-A of step b. The conductive adhesive 381 is shown in contact with and resting on the bond pads 332. Step d shows the hybrid substrate 60 in position to be bonded to the flexible thin film lead 10. The conductive adhesive 381 provides an electrical path between the input/output contacts 322 and the bond pads 332. Step c illustrates the completed bonded assembly wherein the flexible thin film lead 10 is bonded to the substrate 60, thereby providing a path for electrical signals to pass to the living tissue from the package 14. The assembly has been electrically isolated and hermetically sealed with adhesive underfill 380, which is preferably epoxy.

Alternatively, the package may be constructed from a single or multiple layers of a single or multiple polymers, including but not limited to biocompatible epoxies, Parylene, polyimide, silicone, PDMS, PGA, Teflon, PEG, and PMMA.

To this package a polymer-based electrode cable 330, array 331, and a bond pad region 332 are attached. The cable, bond pad region, and array is a single integrated unit that forms the flexible thin film lead 10 shown in FIG. 17 with bond pads 335 at the proximal end and electrodes 333 at the distal end. The cable and array unit is composed of a base polymer 336 layer, one interlayer of patterned metal 337 (or a stack up of metals) comprising traces 33, and electrodes 333, and a top polymer layer 338 that is patterned to expose the pads and electrodes, but insulate the traces. Such a cable and array may be referred to collectively as a thin film lead 10 and may be manufactured in a manner disclosed in patent application Ser. Nos. 11/207,644, and 11/702,735, incorporated herein by reference. Alternatively, the lead may consist of more than one metal interlayer and corresponding additional polymer interlayers so that the thin film lead may be considered a multilayer structure. In a more preferable embodiment, the polymer employed for the base layer, inter layer(s), and top layer is polyimide. Other possible polymers include Parylene, silicone, Teflon, PDMS, PMMA, PEG, and others.

The thin film lead consists of at least 30 independent pads, traces, and electrodes, or preferably at least 50, 60, 100, or 200 pads, traces, and electrodes. The advantages of having so many independent channels is that stimulation may be performed at several sites at once resulting in better therapy, or if combined with a sensing/recording/feedback mechanism either at the time of surgical implantation or throughout the life of the implant, optimal electrodes may be selected for stimulation, reducing the total power output required which reduces power consumption and may also minimize the occurrence of side effects.

The electrodes of the thin film lead are preferably biocompatible and capable of delivering stimulation charge densities of at least 0.1 mC/cm$^2$. One metal often employed to deliver such charge densities is platinum but other noble metals and some metal oxides and nitrides may be used. Since it is an advantage of the current invention to have numerous electrodes it may be necessary in some applications, where the array is to be small, to have the stimulating electrodes be small, preferably less than about 500 um, or less than 250 um, or less than 200, 200, 50, 25 and 10 um. For such small electrodes, therapeutic doses of electrical current are likely to exceed 0.1 mC/cm$^2$, and in such cases it may be desirable to employ electrode materials that permit the safe use of higher charge densities. Two such electrode materials are platinum gray and super iridium oxide, disclosed in U.S. Pat. No. 6,974,533 and U.S. patent application Ser. No. 10/655,772, incorporated herein by reference.

The thin film lead 10 is intended to penetrate the cranium 7 through a surgical opening in the cranium and dura 12 and sit on the surface of the brain (FIG. 2B) such that the array 331 of electrodes 333 is at or near the intended target for stimulation, or the thin film lead may penetrate into the brain (FIG. 2A) so that the array of electrodes reaches the intended target for stimulation deep within the brain. Alternatively, the thin film lead may be placed on an inner surface of the brain between two or more lobes.

Figure 18A:
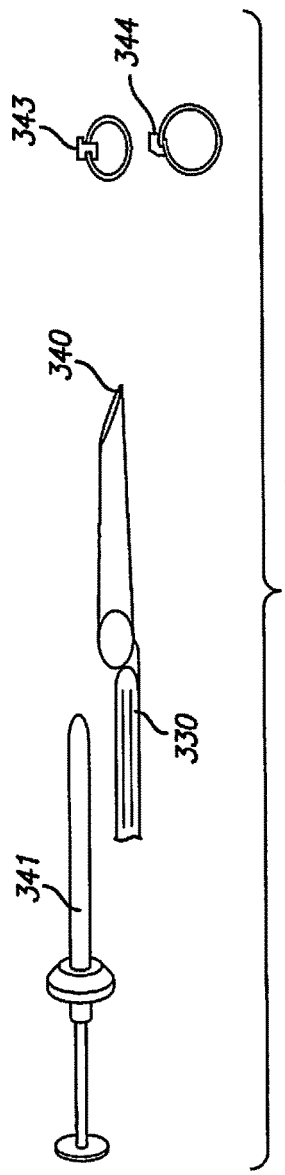
FIG. 18A shows the thin film array of the present invention formed in a columnar structure and its implantation tool.
Figure 18B:
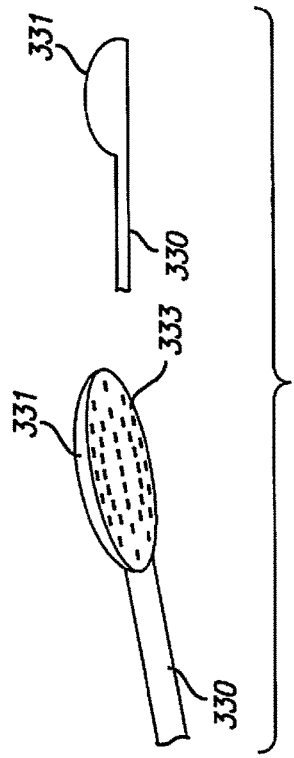
FIG. 18B shows the thin film array formed to match the shape of target tissue.
Figure 18C:
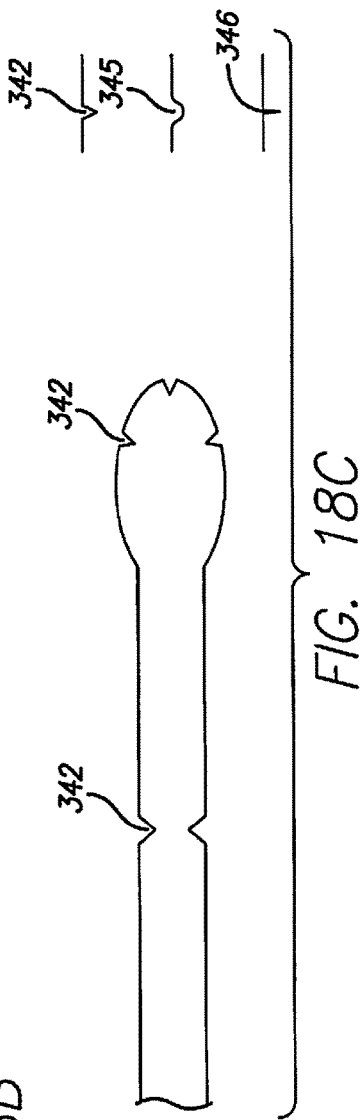
FIG. 18C shows the thin film array of FIG. 18B before forming.

The thin film lead in one embodiment may be substantially flat and planar for its entire length. In other embodiments it may be desirable to shape all, much, or some of the lead. For example it may be desirable to curve a region of the lead along its longitudinal axis into a columnar structure that is more rigid than the planar array (FIG. 18A). In such a scenario the edges of the folded structure may or may not overlap and could be held in place with a binding material such as silicone 343 and 344. This binding material could be beaded along the edge or applied to the entire edge or in distinct locations. It may also be desirable to have a sharpened tip 340 for this structure such that it may be used to penetrate the brain, and/or an introducer 341 that may be inserted into the columnar structure and used to guide the lead into place. In another embodiment (FIG. 18B), where the array is intended to be placed on the surface of the brain, either for recording or stimulation, it may be desirable to shape the array region of the lead to conform to the intended target. Such shaping may be accomplished using molding or thermo-forming of the thermoset or thermoplastic polymers used in the lead. In any case where 3D shaping of the lead or components of the lead are desired, it may be desirable to include physical features in the planar thin film lead (such as cut outs 342) that facilitate this shaping step. These cutouts could have a variety of shapes such as a rounded feature 345 or a slit 346.

In an alternative embodiment (shown in FIG. 23), it may be desirable to attach an array of penetrating electrodes 13 to the package(s), either in place of the thin film lead, or in addition to the thin film array. Such a penetrating array is composed of electrodes of an aspect ratio and sharpness suitable for allowing the array to penetrate the dura and/or brain in order to contact neurons that are not at the brain's surface. Such a penetrating array may be more suitable for recording neuronal activity, or sensing a physiological parameter than a surface thin film lead or a penetrating thin film lead. Additionally, such an array may be able to stimulate cells within the brain more efficiently than the thin film leads. It may also be desirable to use a penetrating array for sensing/recording and a surface thin film lead for stimulation. It may be also be desirable to use a penetrating array for sensing and/or recording and/or stimulation and a surface thin film lead for sensing and/or recording and/or stimulation. FIG. 23A shows an array of penetrating electrodes penetrating the brain in one location with a surface thin film lead in another location, while FIG. 23B shows both types of arrays in a similar location. FIG. 23C shows an embodiment that uses a penetrating thin film lead in conjunction with a surface thin film lead.

The array and/or portions of the cable which comprise the thin film lead may be fixated to tissue (scalp, cranium, brain matter or dura) using several possible techniques. One fixation method would employ a tack similar to that disclosed in U.S. patent application Ser. No. 09/975,427, incorporated herein by reference. In one embodiment the tack would penetrate through a hole in the array 345 or cable into neighboring tissue. In another embodiment at least two tacks would penetrate at least two holes in the cable and/or array. A biocompatible glue or adhesive may be used to fix the array and/or cable in place. This glue or adhesive may be preferentially reversible through the administration of light, heat, energy, or a chemical agent in order to allow rapid removal of the thin film lead. Electro-tacking, whereby one or more electrodes are sacrificed to fix the array to tissue by discharging a significant electrical current through the electrode, may also be employed. This process may also be reversible. Alternatively, physical features may be constructed in the polymer thin film lead that permit anchoring of the lead to adjacent tissue. Such features may be one or more protuberances that anchor into tissue when pressure is applied or holes that permit tissue growth through and around the lead. In another embodiment, regardless of the method of array attachment used, it may be desirable to attach the array to the inside (brain side) surface of the dura with the electrodes facing the brain. In this embodiment it may be necessary to put a spacer between the array and the dura in order to force the electrodes to be proximal to the brain tissue target for stimulation. One such spacer is made from a biocompatible sponge-like material. Additionally, one or more handle type structures 339 may be added to the thin film lead to permit holding of the lead or a region of the lead using surgical tools such as forceps, or end gripping forceps.

Attachment of the bond pad region 332 of the thin film lead 10 to the package 14 is carried out using a method or methods similar to those disclosed in U.S. Pat. Nos. 7,142,909 and 7,211,103, incorporated herein by reference.

One or more reference or return electrodes must be provided in order to provide a return for the stimulation current. A feature of the present invention is that the return electrode(s) be provided in or on the brain. The return electrodes may be contained on the thin film lead(s) containing the stimulation electrodes or they may be on their own independent leads that may or may not be thin film leads. Alternatively, the lid and/or other metal components of the package(s) may be used to provide an electrical return.

A coil 16 is also attached to the package 14. This coil permits radio-frequency communication between the implant and an external apparatus. This coil may receive power and data signals from the external apparatus and may send information about the implant or a sensed physiological condition out to the external apparatus. The coil may be attached to the package via wire leads 5 or alternatively may be attached to the polymer thin film lead 10 via bonding of the coil wires to additional bond pads in the polymer. Or in another embodiment the coil may be integrated into polymer thin film lead as a patterned metal coil made from the same or a different metal stack up as that employed in the rest of the lead. The coil profile and shape is such that the scalp may rest of top of the coil without being irritated. Thus the coil is low profile with rounded edges and is preferably encased in a biocompatible soft polymer mold such as a silicone or other elastic polymers. The coil(s) facilitates transmission of data between the implant and the external system and possibly between implanted coils. In the case of a device without a rechargeable battery the coil is also used to receive power from an external source. It is a feature of the present invention that where the implanted coil(s) is to receive both power and data, at least two different carrier frequencies are used; one for power transmission and one or more for data transmission.

In another embodiment of the present invention a sensor is employed in the device where the sensor is contained within the package, and/or on the thin film lead. As well, the electrodes (either on a penetrating array/lead or on a thin film surface lead) may be used to record electrical activity in the brain, or measure electrical properties of the entire system (i.e. impedance, or voltage waveforms). The output from such a sensor/recorder/measurement system may be used by the implanted electronics to determine a course of action or the information may be telemetered out to the external system to be processed in order to determine a parameter of interest. The external system determines a course of action if necessary and telemeters that data back to the implant. Optionally, the external system may telemeter the calculated parameter value(s) back to the implant for subsequent decision making.

Figure 19A:
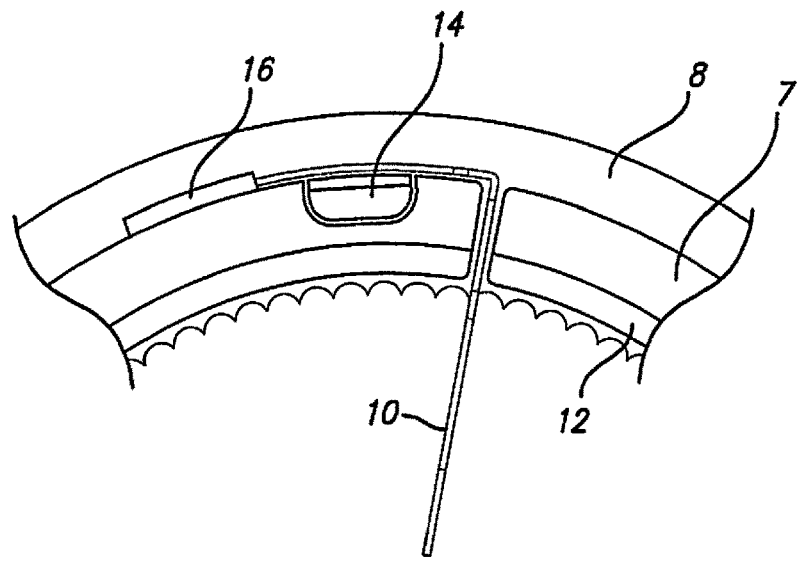
FIG. 19A shows the implantation location of the present invention with the coil on the surface of the cranium.

In another embodiment of the present invention (FIG. 19), it may be desirable to countersink the package 14 into the cranium 7 in order to protect the device from damage due to an external blow to the head or to prevent irritation of the scalp (shown in FIG. 19A). It may be desirable to turn the package upside down in such a configuration so that the thin film lead comes out on the surface of the cranium (as shown). Also, it may be desirable to countersink the coil 16 in the cranium 7 for the same reasons. Although a thin film multi-electrode lead is shown penetrating the brain in this figure, it is possible that the lead may rest on the surface of the brain or between lobes of the brain. Although no flange or tabs are shown on the package or coil in this figure it is implied that such fixation features may be present.

Figure 20A:
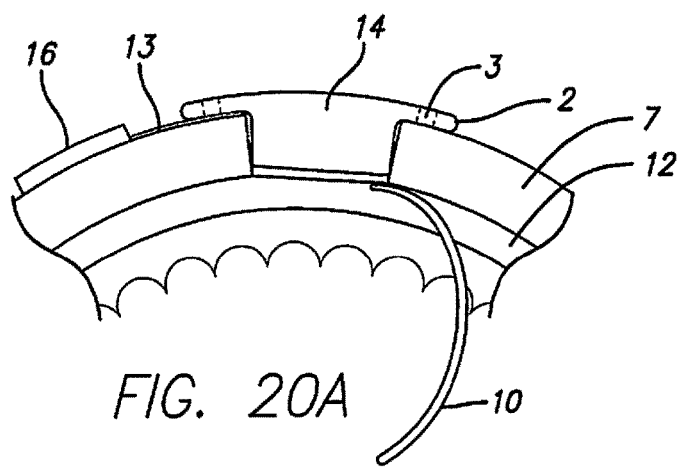
FIG. 20A shows an alternate implantation location for the present invention with a lip over the cranium and the coil on an outside surface of the cranium.

In another embodiment of the present invention (FIG. 20), it may be desirable to have the package 14 be of such a height that it just protrudes through a hole made in the cranium 7, but not through the dura 8. Again, this may protect the device from harm and reduce irritation of the scalp. Additionally, such an architecture reduces the number of incisions in the cranium as a separate orifice for the lead 10 is not required. The coil may still rest on the outside of the cranium (FIG. 20A) or under the cranium (FIG. 20B) as required.

Figure 19B:
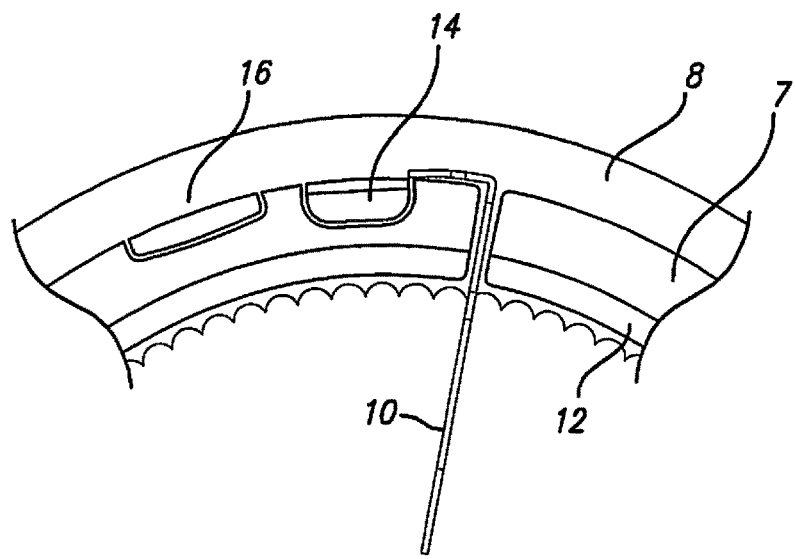
FIG. 19B shows the implantation location of the present invention with the coil counter sunk in the cranium.

Although specific combinations of package, coil and thin film lead and/or penetrating array location are shown in FIGS. 2, 19 and 20, it is understood that these architectures are not limiting in any sense and that any permutation or combination of these architectures is also disclosed in this invention. Similarly, it is understood that there is no reason to limit the implant architecture to containing only one of a coil, package, and thin film lead. The present invention may consist of any number of those components disposed at different positions in the head as previously described. An example is provided in FIG. 21. In this embodiment there are 2 packages 14 and 15, a primary controller, which houses electronics for the implant, and another secondary package which primarily contains a battery but may alternatively contain some additional electronics or may only contain additional electronics. Two thin film leads 10 are attached to the primary controller. One of these leads may penetrate the brain while the other sits on a surface, or both may penetrate or both may sit on the surface. Two coils 16 and 17 are attached to the primary controller perhaps for redundancy or perhaps to permit easier collocation of the external communication unit.

It is a feature of this embodiment that the secondary package is connected to the primary controller using the same polymer based cable structure as that employed for the two thin film leads 350. This is shown more clearly in FIG. 21C which indicates that the entire polymer based thin film structure including both leads all interconnections required for multiple packages and coils may be provided in one piece. Alternatively, it may be desirable to have the secondary package attach to the primary controller using a connector that can be connected or unconnected in situ. An example of such a connector 351 is shown in FIG. 21C. Here wire leads from the secondary package plug into a connector on the primary controller facilitating, potentially, easy replacement of the secondary feature (say a battery). Other connector embodiments will be readily apparent to one with normal skill in the art. The primary feature of such a connector is that it provides for minimal electrical current leakage (at least less than 1 uA/s, more preferably less than 0.1 uA/s or even 0.01 uA/s).

Although FIG. 21 shows one device architecture it should not be limiting as it may be appreciated that any number of coils, packages, and leads may be used in any combination, and that any polymer based structure(s) used to connect the components do not necessarily need to be manufactured in one integrated unit. As well, the physical locations of the components in, on, or under the cranium may also vary.

Figure 20C:
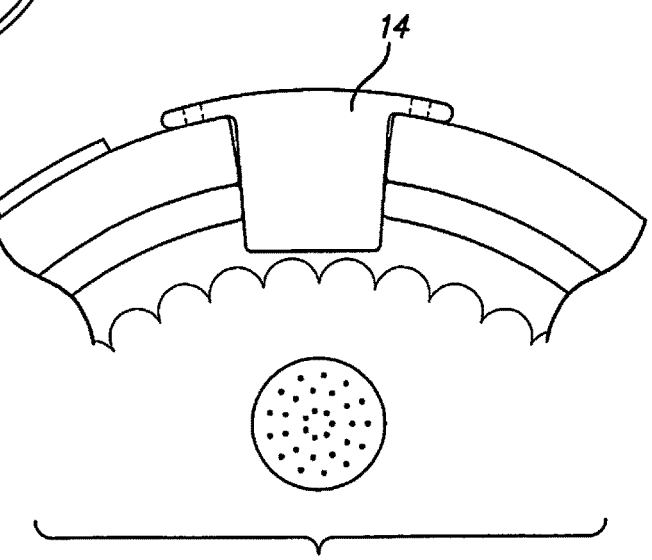
FIG. 20C shows an alternate embodiment with the electrodes directly on the package.
Figure 20B:
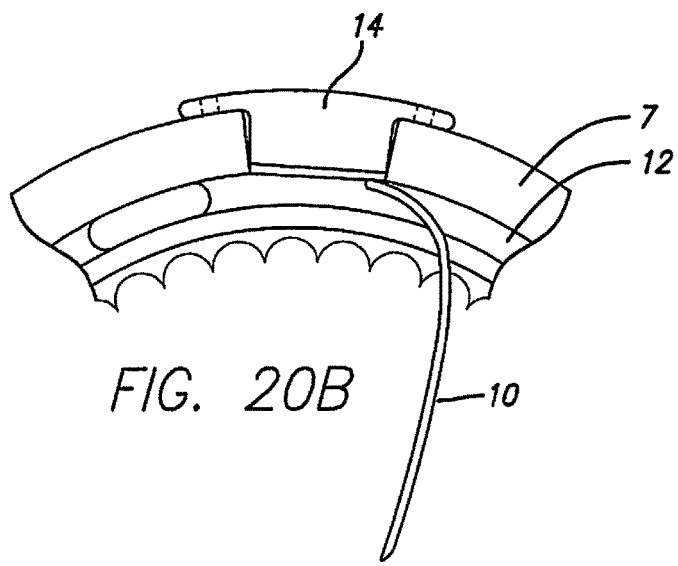
FIG. 20B shows an alternate implantation location for the present invention with a lip over the cranium and the coil within the cranium.

Similarly, it is an aspect of the present invention that a thin film lead may not be required. Instead multiple electrodes may be formed in the package itself. One such embodiment is shown in FIG. 20C where the package extends through the cranium and dura and makes contact with the surface of the brain with multiple electrodes.

It is also an aspect of the present invention that the coil need not be remote from a package but may alternatively be contained in a package. Another aspect of the present invention includes coating the package(s), and/or coil(s), and/or thin film lead(s) with materials that enhance biocompatibility, resistance to corrosion, tissue growth, neural tissue growth, and/or coatings that deliver pharmaceutical agents that enhance device function or disease treatment.

Another embodiment of the present invention includes the addition of one or more integrated circuits or chips that are coated in a biocompatible and hermetic thin film package of the type disclosed in U.S. Pat. Nos. 7,127,286 and 7,190,051, and patent application Ser. Nos. 11/406,743 and 11/343,170, incorporated herein by reference. A chip or chips coated in such a way enables new device architectures that benefit from a reduction in the size of the device and/or a further increase in the number of electrodes.

Examples of these new architectures are shown in FIG. 22. In FIG. 22A, a coated chip 49 (a demultiplexer for example) is added to the thin film lead near the array. In this way, the traces in the lead can be used to address more than a single electrode. For example, if the ceramic feedthrough permits at most 68 vias 16 but perhaps 480 electrodes are desired for the device, then 60 traces (along with some power and control lines) may be routed to the chip 49 which can perform 8:1 demultiplexing of the input signals to high density electrode outputs also located on the chip. An example is shown in FIGS. 22D and 22E (although 8:1 demultiplexing is not necessarily maintained in the drawing). It should be obvious to one of reasonable skill in the art that more than one coated chip may be used in such an architecture, and that coated discrete electronic components may also be employed. In another embodiment, the demultiplexing function may be moved to inside one or more of the packages. In this scenario, the ceramic may contain enough feedthroughs to address each electrode individually, but the electronics may not have enough drivers to drive current through each electrode independently. In this case the demultiplexing may occur within in the package.

Alternatively, it may be possible to place all of the required electrical circuitry on a single coated chip or multiple coated chips with or without demultiplexing such that the chip(s) can be placed under the cranium and or dura as shown in FIG. 22B. In this case the chip is shown deep within the brain but it may be appreciated by anyone skilled in the art that the chip may also be on a surface of the brain or dura. In this case only data and/or power from an implanted coil and/or battery located on the cranium (as shown), in the cranium, or under the cranium need be routed to the chip along a thin film lead. Alternatively, even the coil may be integrated into the coated chip such that no additional component is required as shown in FIG. 22C. In such a scenario it may or may not be desirable to have the chip interconnected to a polymer lead of similar size as the chip, such lead containing the electrodes that interface with the tissue. This step may be required to tailor the physical properties of the tissue interface or to permit manufacturing processes for the electrodes (for example electro-plating of platinum gray) that might not otherwise be possible if the electrodes were placed directly on the chip.

Although specific examples of numbers and locations of coils, packages, leads, and chips are shown in the drawings it is implied that any combination of numbers of components and their locations that are reasonable extensions from this invention are also included.

In one other embodiment, a package of the type already disclosed in FIG. 3 but of very low profile, preferably less than 2 mm, or 1.5 mm, or even 1 mm in height, may be used to encase and protect the chip(s) (and possibly other components) rather than a thin film package. Again, several such packages implanted beneath the dura on the surface of or deep within the brain may also be desirable.

Figure 24:
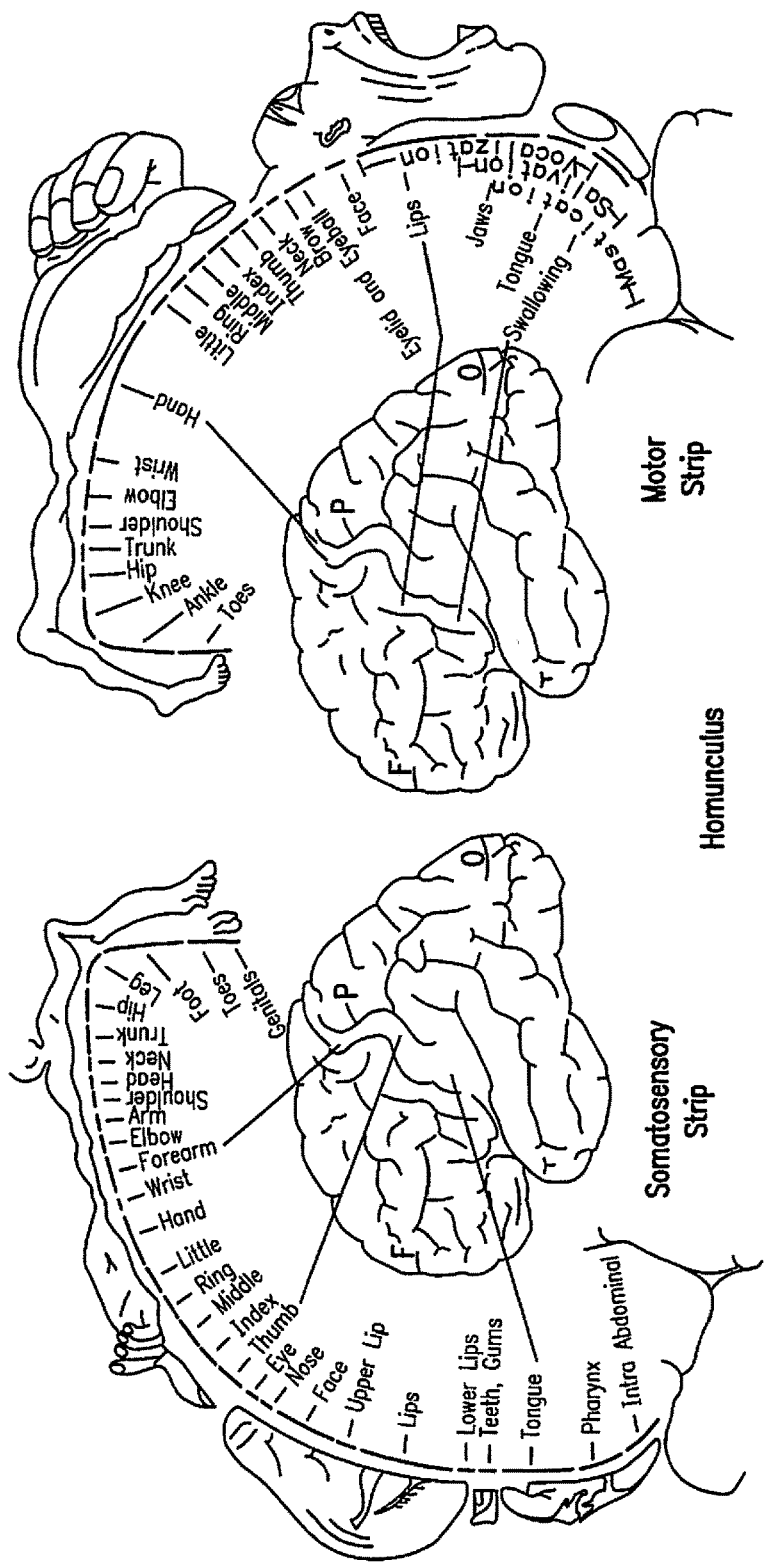
FIG. 24 is a schematic diagram of the brain to further illustrate areas which could be stimulated by the present invention.
Figure 25A:
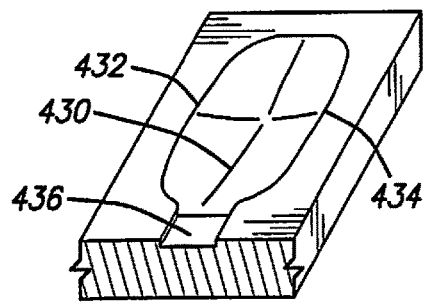
FIG. 25A depicts a mold for forming the flexible circuit array in a curve.
Figure 25B:
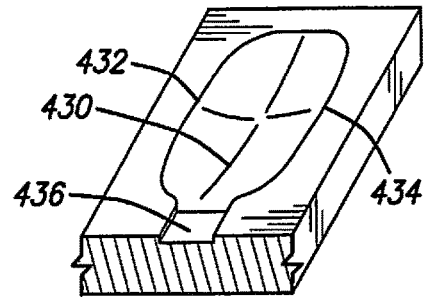
FIG. 25B depicts a mold slightly smaller than the mold of FIG. 25A.
Figure 25C:
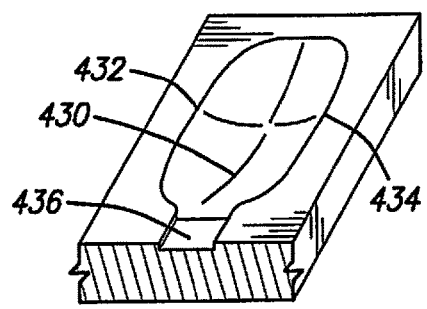
FIG. 25C depicts a mold slightly smaller than the mold of FIG. 25B.
Figure 25D:
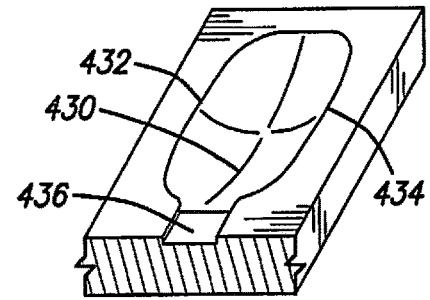
FIG. 25D depicts a mold slightly smaller than the mold of FIG. 25C.
Figure 25E:
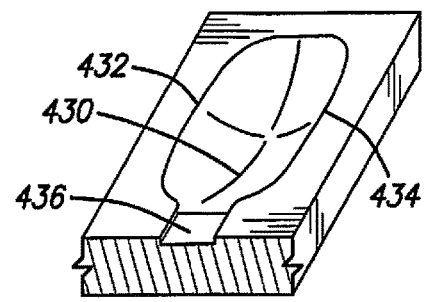
FIG. 25E depicts a mold slightly smaller than the mold of FIG. 25D.

Referring to FIG. 24, specific target stimulation areas of the brain for the system described include the sensory and motor areas.

Example Applications

1. Visual prosthesis: external or implantable video camera (CCD or CMOS) that sends data to an image processor, which sends information to the implanted stimulator, which stimulates the LGN or V1 visual cortex in the occipital lobe.
2. Auditory prosthesis: external or implantable microphone that sends data to an audio processor, which sends information to the implanted stimulator, which stimulates the auditory cortex or cochlear nucleus.
3. Somatosensory prosthesis: external or implantable sensors that respond to—
   a. Pressure
   b. Temperature (heat or cold)
   c. Harmful stimuli such as sharp objects
which send data to a processor that then sends the information to an implanted prosthesis with stimulating electrodes on or in the somatosensory strip.
4. Anti-depression prosthesis: device which stimulates areas of the somatosensory strip intended to produce endorphin release or other positive feelings (ex. corresponding to genital area).
5. Cortically driven motor prosthesis: electrodes implanted on or in the motor strip, which when activated cause involuntary movements in the subject.
6. Control for external robotic prosthesis-implant with recording electrodes on or in pre-motor (forward of motor strip) or motor strip, which sends data wirelessly to an external processor, which drives a robotic limb (arm, hand, leg, foot) or stimulates muscles in a denervated arm, hand, leg, foot, face, tongue, etc.)
7. Epilepsy monitor/stimulator: device with two arrays— one array (either penetrating or surface array) records signals—single neuron units or local field potentials. This array sends data to an implanted or external processor with a predictive algorithm to predict the onset of a seizure. The processor then sends current pulses or waveforms to a second implanted electrode array (either penetrating or surface array) which arrests and prevents the seizure from occurring or spreading.

The flexible circuit 1 is made by the following process. First, a layer of polymer (such as polyimide, fluoro-polymers, silicone or other polymers) is applied to a support substrate (not part of the array) such as glass. Layers may be applied by spinning, meniscus coating, casting, sputtering or other physical or chemical vapor deposition, or similar process. Subsequently, a metal layer is applied to the polymer. The metal is patterned by photolithographic process. Preferably, a photo-resist is applied and patterned by photolithography followed by a wet etch of the unprotected metal. Alternatively, the metal can be patterned by lift-off technique, laser ablation or direct write techniques.

It is advantageous to make this metal thicker at the electrode and bond pad to improve electrical continuity. This can be accomplished through any of the above methods or electroplating. Then, the top layer of polymer is applied over the metal. Openings in the top layer for electrical contact to the electronics package 14 and the electrodes may be accomplished by laser ablation, or reactive ion etching (RIE) or photolithography and wet etch. Making the electrode openings in the top layer smaller than the electrodes promotes adhesion by avoiding delamination around the electrode edges.

The pressure applied against the neural tissue by the flexible circuit electrode array is critical. Too little pressure causes increased electrical resistance between the array and the tissue. It should be noted that where the present invention is described in terms of application to the brain, the techniques described are equally applicable to many forms of neural stimulation. Application to the brain requires a convex spherical curve. Application to the cochlea requires a constant curve in one dimension and a spiral curve in the other. Application to the cerebral cortex requires a concave spherical curve. Cortical stimulation is useful for artificial vision or hearing, touch and motor control for limb prostheses, deep brain stimulation for Parkinson's disease and multiple sclerosis, and many other applications.

Common flexible circuit fabrication techniques such as photolithography generally require that a flexible circuit electrode array be made flat. Since the brain is spherical, a flat array will necessarily apply more pressure near its edges, than at its center. With most polymers, it is possible to curve them when heated in a mold. By applying the right amount of heat to a completed array, a curve can be induced that matches the curve of the brain. To minimize warping, it is often advantageous to repeatedly heat the flexible circuit in multiple molds, each with a decreasing radius. FIG. 25 illustrates a series of molds according to the preferred embodiment. Since the flexible circuit will maintain a constant length, the curvature must be slowly increased along that length. As the curvature 430 decreases in successive molds (FIGS. 25A-25E) the straight line length between ends 432 and 434 must decrease to keep the length along the curvature 430 constant, where mold 25E approximates the curvature of the brain or other desired neural tissue. The molds provide a further opening 436 for the flexible circuit cable 10 of the array to exit the mold without excessive curvature.

It should be noted that suitable polymers include thermoplastic materials and thermoset materials. While a thermoplastic material will provide some stretch when heated, a thermoset material will not. The successive molds are, therefore, advantageous only with a thermoplastic material. A thermoset material works as well in a single mold as it will with successive smaller molds. It should be noted that, particularly with a thermoset material, excessive curvature in three dimensions will cause the polymer material to wrinkle at the edges. This can cause damage to both the array and the brain. Hence, the amount of curvature is a compromise between the desired curvature, array surface area, and the properties of the material.

Figure 26:
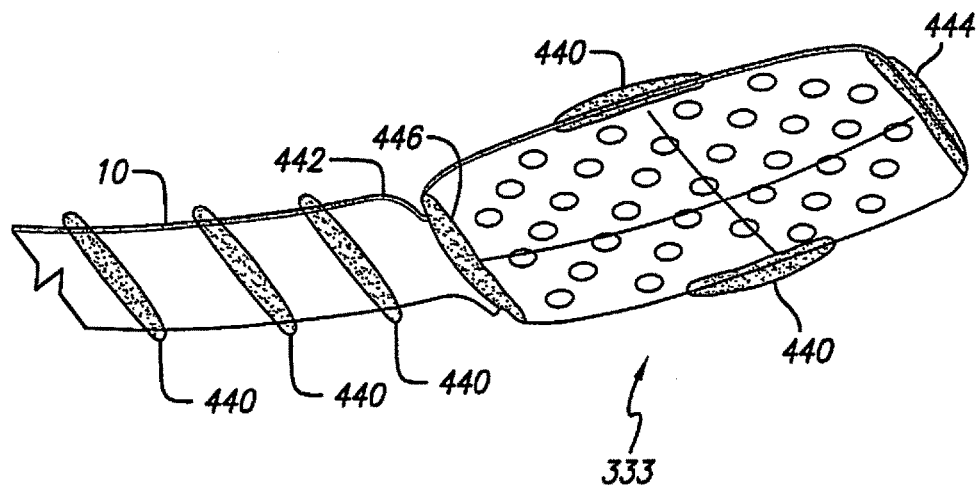
FIG. 26 depicts an alternate view of the invention with ribs to help maintain curvature and prevent tissue damage.

Referring to FIG. 26, the edges of the polymer layers are often sharp. There is a risk that the sharp edges of a flexible circuit will cut into delicate tissue. It is advantageous to add a soft material, such as silicone, to the edges of a flexible circuit electrode array to round the edges and protect the brain. Silicone around the entire edge is preferable, but may make the flexible circuit less flexible. So, another embodiment as depicted in FIG. 26 has discrete silicone bumpers or ribs to hold the edge of the flexible circuit electrode array away from the brain tissue. Curvature 440 fits against the neural tissue to be stimulated, in this case the brain. The leading edge 444 is most likely to cause damage and is therefore fit with a molded silicone bumper. Also, the edge 446 where the array lifts off the brain can cause damage and should be fit with a bumper. Any space along the side edges of curvature 440 may cause damage and may be fit with bumpers as well. It is also possible for the flexible circuit cable 10 of the electrode array to contact the brain. It is, therefore, advantageous to add periodic bumpers along the flexible circuit cable 10.

Figure 27:
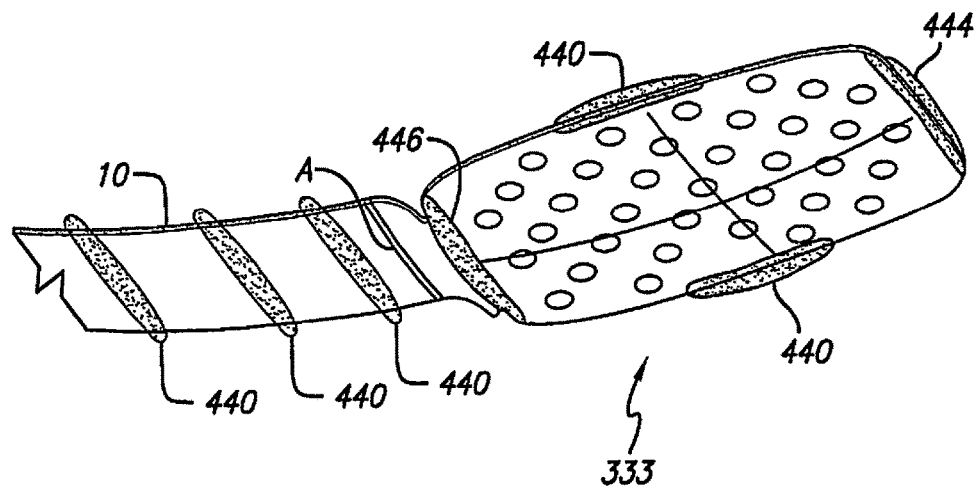
FIG. 27 depicts an alternate view of the invention with ribs to help maintain curvature and prevent tissue damage, fold of the flexible circuit cable, and a fold A between the circuit electrode array and the flexible circuit cable.

FIG. 27 depicts a further embodiment of the part of the prosthesis shown in FIG. 26 with a fold A between the flexible circuit electrode array 333 and the flexible circuit cable 10. The angle in the fold A also called the ankle has an angle of 1°-180°, preferably 80°-120°. The fold A may be advantageous in reducing tension and enabling a more effective attachment of the flexible circuit electrode array.

Figure 28:
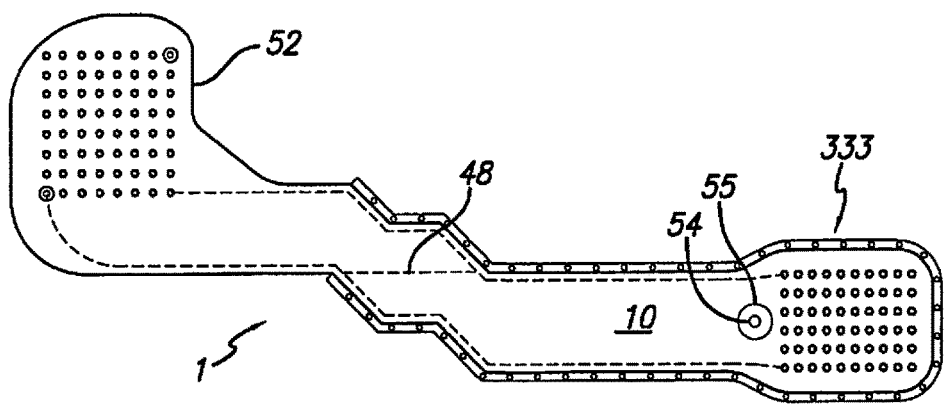
FIG. 28 depicts the flexible circuit array before it is folded and attached to the implanted portion.

FIG. 28 shows the flexible circuit electrode array prior to folding and attaching the array to the electronics package. At one end of the flexible circuit cable 10 is an interconnection pad 52 for connection to the electronics package. At the other end of the flexible circuit cable 10 is the flexible circuit electrode array 333. Further, an attachment point 54 is provided near the flexible circuit electrode array 333. A tack (not shown) may be placed through the attachment point 54 to hold the flexible circuit electrode array 333 to tissue. A stress relief 55 is provided surrounding the attachment point 54. The stress relief 55 may be made of a softer polymer than the flexible circuit, or it may include cutouts or thinning of the polymer to reduce the stress transmitted from the tack to the flexible circuit electrode array 333. The flexible circuit cable 10 is formed in a dog leg pattern so than when it is folded at fold 48 it effectively forms a straight flexible circuit cable 10 with a narrower portion at fold 48.

Figure 29:
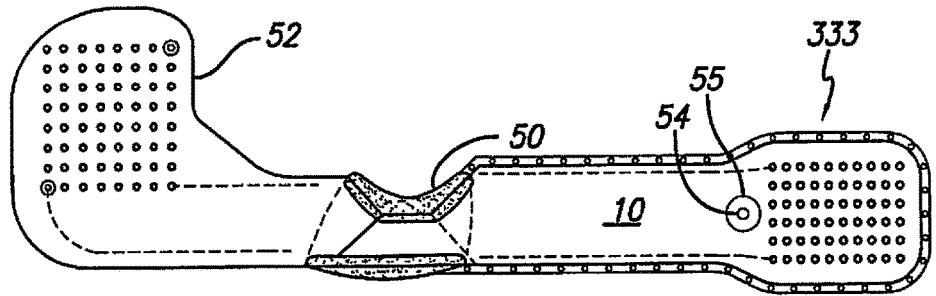
FIG. 29 depicts the flexible circuit array, folded.

FIG. 29 shows the flexible circuit electrode array after the flexible circuit cable 10 is folded at the fold 48 to form a narrowed section. The flexible circuit cable 10 may include a twist or tube shape as well. With a brain prosthesis as shown in FIG. 1, the bond pad 52 for connection to the electronics package 14 and the flexible circuit electrode array 333 are on opposite sides of the flexible circuit. This requires patterning in some manner, of both the base polymer layer and the top polymer layer. By folding the flexible circuit cable 10 of the flexible circuit electrode array 333, the openings for the bond pad 52 and the electrodes are on the top polymer layer, and only the top polymer layer needs to be patterned.

Further, it is advantageous to provide a suture tab 56 in the flexible circuit body near the electronics package to prevent any movement in the electronics package from being transmitted to the flexible circuit electrode array 333. Alternatively, a segment of the flexible circuit cable 10 can be reinforced to permit it to be secured directly with a suture.

An alternative to the bumpers described in FIG. 26 is a skirt of silicone or other pliable material as shown in FIGS. 31, 32, 33 and 34. A skirt 460 covers the flexible circuit electrode array 333, and extends beyond its edges. It is further advantageous to include wings 462 adjacent to the attachment point 54 to spread any stress of attachment over a larger area of the brain. There are several ways of forming and bonding the skirt 460. The skirt 460 may be directly bonded through surface activation or indirectly bonded using an adhesive.

Alternatively, a flexible circuit electrode array 333 may be layered using different polymers for each layer. Using too soft of a polymer may allow too much stretch and break the metal traces. Too hard of a polymer may cause damage to delicate neural tissue. Hence a relatively hard polymer, such as a polyimide, may be used for the bottom layer, and a relatively softer polymer, such as silicone, may be used for the top layer including an integral skirt to protect delicate neural tissue. The top layer is the layer closest to the neural tissue.

Figure 31:
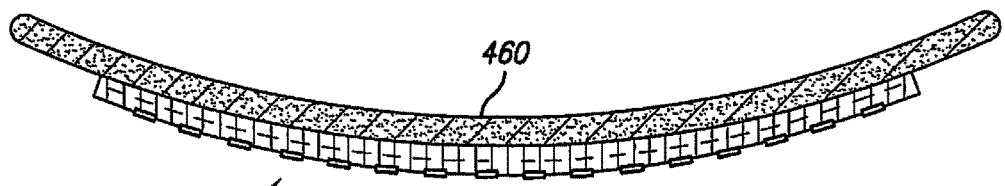
FIG. 31 depicts a flexible circuit array with a protective skirt bonded to the back side of the flexible circuit array.
Figure 32:
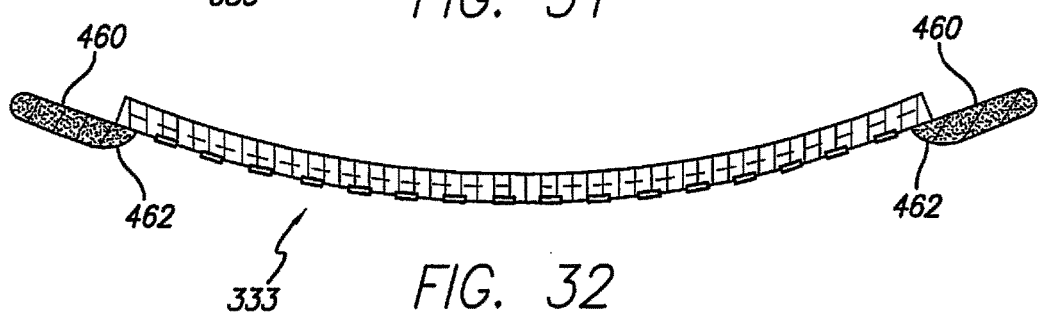
FIG. 32 depicts a flexible circuit array with a protective skirt bonded to the front side of the flexible circuit array.

The simplest solution is to bond the skirt 460 to the back side (away from the tissue) of the flexible circuit electrode array 333 as shown in FIG. 31. While this is the simplest mechanical solution, the sharp edges of the flexible circuit electrode array 333 may contact the delicate tissue. Bonding the skirt to the front side (toward the brain) of the flexible circuit electrode array 333, as shown in FIG. 32, will protect the neural tissue from the sharp edges of the flexible circuit electrode array 333. However, a window 462 must be cut in the skirt 460 around the electrodes. Further, it is more difficult to reliably bond the skirt 460 to the flexible circuit electrode array 333 with such a small contact area. This method also creates a space between the electrodes and the brain which will reduce efficiency and broaden the electrical field distribution of each electrode. Broadening the electric field distribution will limit the possible resolution of the flexible circuit electrode array 333.

Figure 33:
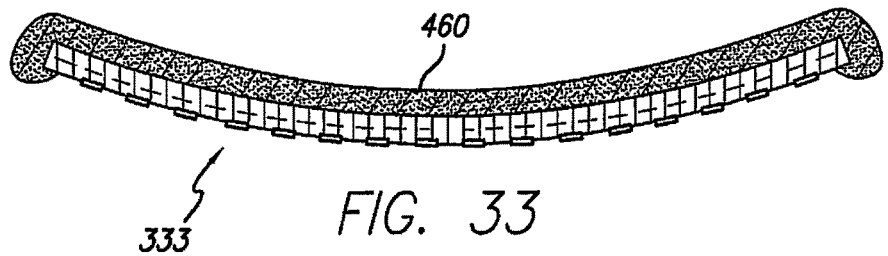
FIG. 33 depicts a flexible circuit array with a protective skirt bonded to the back side of the flexible circuit array and molded around the edges of the flexible circuit array.

FIG. 33 shows another structure where the skirt 460 is bonded to the back side of the flexible circuit electrode array 333, but curves around any sharp edges of the flexible circuit electrode array 333 to protect the brain. This gives a strong bond and protects the flexible circuit electrode array 333 edges. Because it is bonded to the back side and molded around the edges, rather than bonded to the front side of the flexible circuit electrode array 333, the portion extending beyond the front side of the flexible circuit electrode array 333 can be much smaller. This limits any additional spacing between the electrodes and the tissue.

Figure 34:
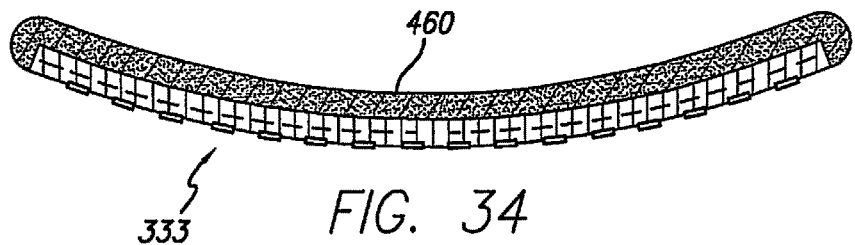
FIG. 34 depicts a flexible circuit array with a protective skirt bonded to the back side of the flexible circuit array, molded around the edges of the flexible circuit array, and flush with the front side of the array.

FIG. 34 shows a flexible circuit electrode array 333 similar to FIG. 33, with the skirt 460, flush with the front side of the flexible circuit electrode array 333 rather than extending beyond the front side. While this is more difficult to manufacture, it does not lift the electrodes off the brain surface as with the array in FIG. 32. It should be noted that FIGS. 31, 33, and 34 show skirt 460 material along the back of the flexible circuit electrode array 333 that is not necessary other than for bonding purposes. If there is sufficient bond with the flexible circuit electrode array 333, it may advantageous to thin or remove portions of the skirt 460 material for weight reduction.

Figure 30:
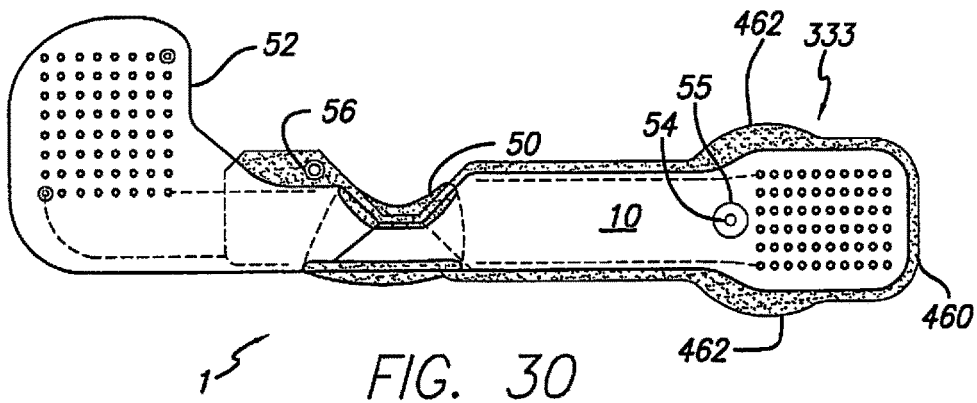
FIG. 30 depicts a flexible circuit array with a protective skirt.
Figure 35:
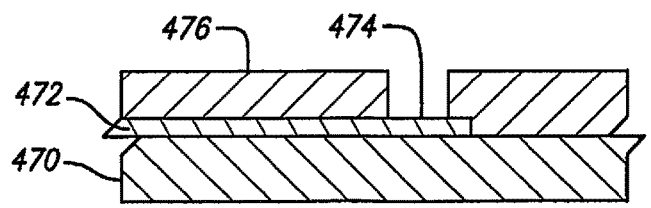
FIG. 35 is an enlarged view of a single electrode within the flexible circuit electrode array.

Referring to FIG. 35, the flexible circuit electrode array 333 is manufactured in layers. A base layer of polymer 70 is laid down, commonly by some form of chemical vapor deposition, spinning, meniscus coating, or casting. A layer of metal 72 (preferably platinum) is applied to the polymer base layer 70 and patterned to create electrodes 74 and traces for those electrodes. Patterning is commonly done by photolithographic methods. The electrodes 74 may be built up by electroplating or similar method to increase the surface area of the electrode 74 and to allow for some reduction in the electrodes 74 over time. Similar plating may also be applied to the bond pads 52 (FIGS. 28-30). A top polymer layer 76 is applied over the metal layer 72 and patterned to leave openings for the electrodes 74, or openings are created later by means such as laser ablation. It is advantageous to allow an overlap of the top polymer layer 76 over the electrodes 74 to promote better adhesion between the layers, and to avoid increased electrode reduction along their edges. The overlapping top layer promotes adhesion by forming a clamp to hold the metal electrode between the two polymer layers. Alternatively, multiple alternating layers of metal and polymer may be applied to obtain more metal traces within a given width.

Figure 36:
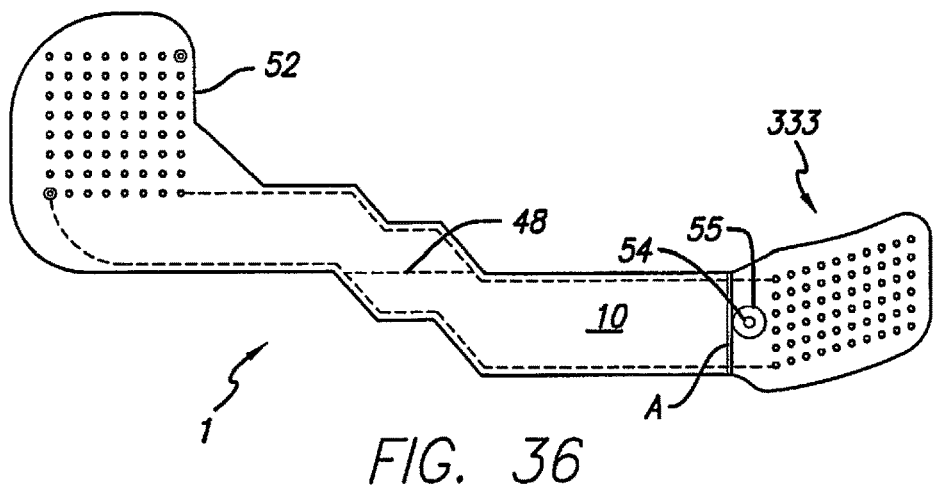
FIG. 36 depicts the flexible circuit array before it is folded and attached to the implanted portion, containing an additional fold between the flexible electrode array and the flexible cable.

FIG. 36 depicts the flexible circuit array 10 before it is folded and attached to the implanted portion containing an additional fold A between the flexible electrode array 10 and the flexible cable 10. The angle in the fold A also called the ankle has an angle of 1°-180°, preferably 80°-120°.

Figure 37:
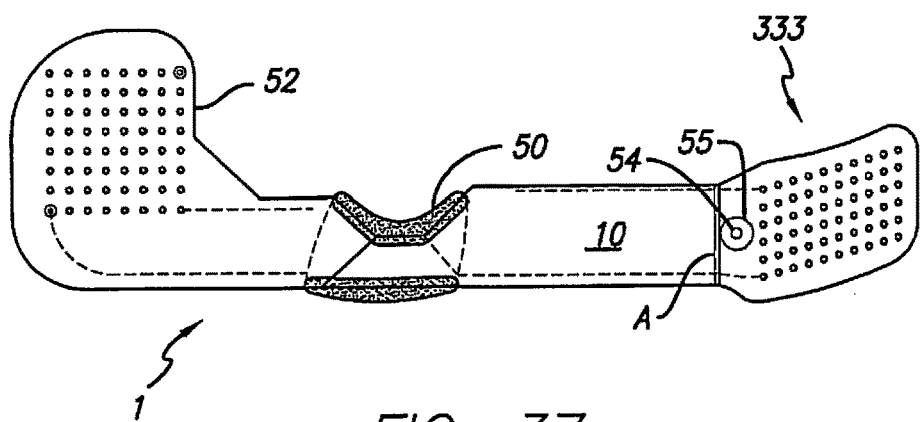
FIG. 37 depicts the flexible circuit array of FIG. 16, folded, containing an additional fold between the flexible electrode array and the flexible cable.

FIG. 37 depicts the flexible circuit array 10 containing an additional fold A between the flexible electrode array 10 and the flexible cable 10. The flexible circuit array as shown in FIGS. 28 and 36 differ by the fold A from each other.

Figure 38:
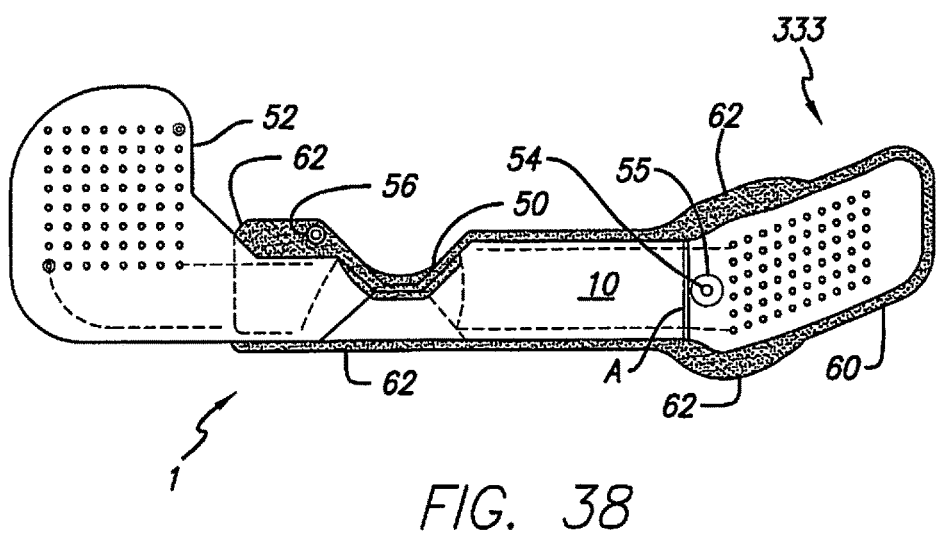
FIG. 38 depicts a flexible circuit array of FIG. 17 with a protective skirt, and containing an additional fold between the flexible electrode array and the flexible cable.
Figure 39:
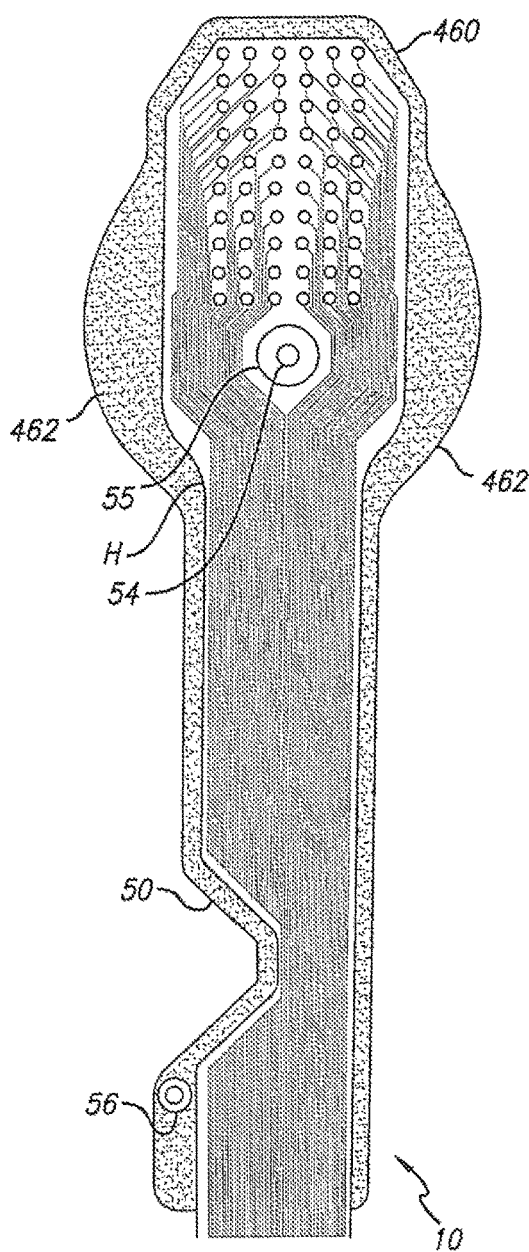
FIG. 39 depicts a top view of a flexible circuit array and flexible circuit cable showing an additional horizontal angle between the flexible electrode array and the flexible cable.
Figure 40:
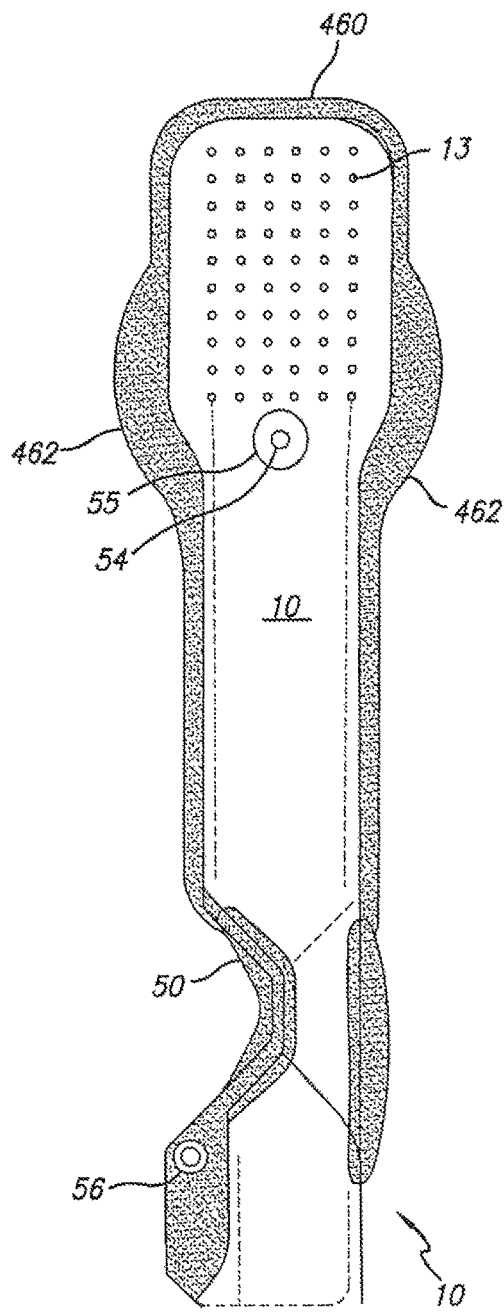
FIG. 40 depicts another variation without the horizontal angle between the flexible electrode array and the flexible cable, but with an orientation of the electrodes in the flexible electrode array, as shown for the variation in FIG. 19.

FIG. 38 depicts a flexible circuit array of FIG. 37 with a protective skirt 460 and containing an additional fold A between the flexible electrode array and the flexible cable. The flexible circuit array as shown in FIGS. 30 and 38 differ by the fold A from each other.

Figure 41:
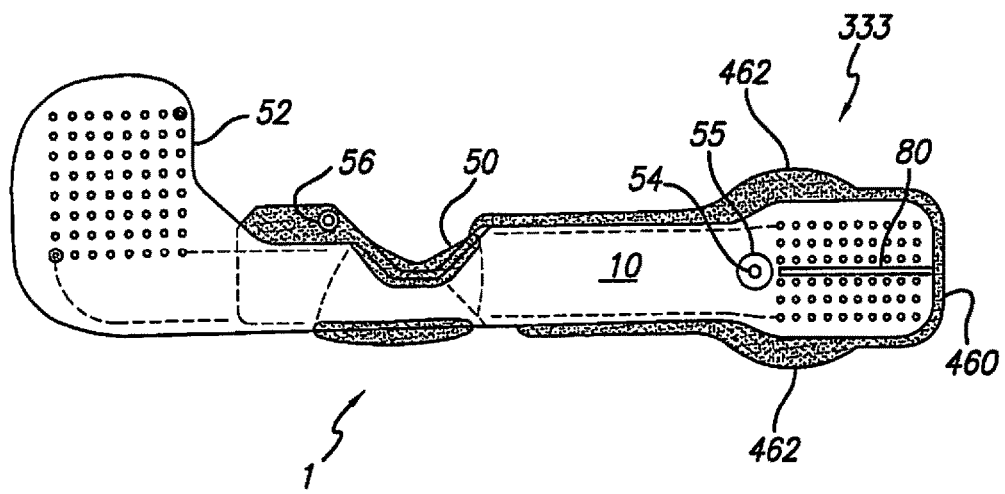
FIG. 41 depicts a top view of a flexible circuit array and flexible circuit cable wherein the array contains a slit along the length axis.

FIG. 41 depicts a top view of a flexible circuit array and flexible circuit cable as shown in FIGS. 30, 38, 39, and 40 wherein the array in FIG. 41 contains a slit 80 along the length axis.

Figure 42:
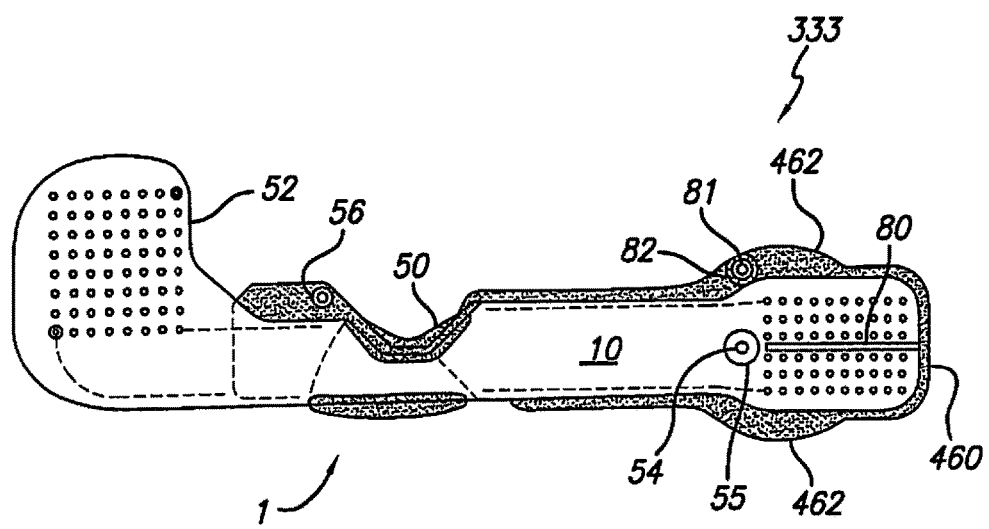
FIG. 42 depicts a top view of a flexible circuit array and flexible circuit cable wherein the array contains a slit along the length axis with two attachment points.

FIG. 42 depicts a skirt of silicone or other pliable material as shown in FIGS. 30 to 34. A skirt 460 covers the flexible circuit electrode array 333, and extends beyond its edges. In this embodiment of the present invention the flexible circuit electrode array contains a slit 80 along the lengths axis. Further, according to this embodiment the skirt of silicone or other pliable material contains preferably at least two attachment points 81 and stress relieves 82 are provided surrounding the attachment points 81. The attachment points 81 are located preferably on the skirt 460 outside the flexible circuit electrode 333 and are positioned apart as far as possible from each other. The secondary tack 81 is far enough away from the first tack location 54 not to cause tenting. Furthermore, the polyimide is completely between the two tacks, which also reduces the possibility of tenting. The wings act like external tabs or stress reliefs. The multiple tacks prevent rotation of the array. Alternatively, the secondary tack could be placed at an attachment point at 83.

The stress relief 82 may be made of a softer polymer than the flexible circuit, or it may include cutouts or thinning of the polymer to reduce the stress transmitted from the tack to the flexible circuit electrode array 333.

Figure 43:
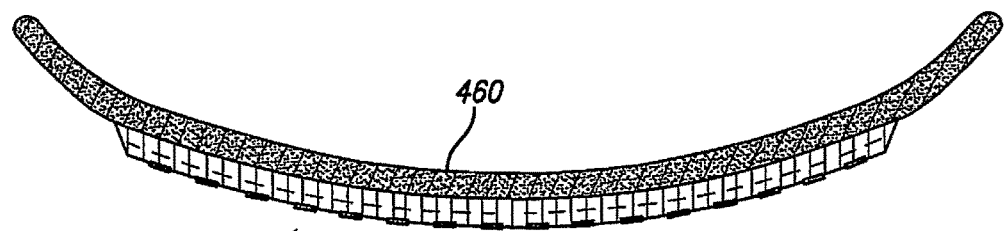
FIG. 43 depicts a flexible circuit array with a protective skirt bonded to the back side of the flexible circuit array with a progressively decreasing radius.

FIG. 43 depicts a flexible circuit array 333 with a protective skirt 460 bonded to the back side of the flexible circuit array 333 with a progressively decreasing radius and/or decreasing thickness toward the edges.

Figure 44:
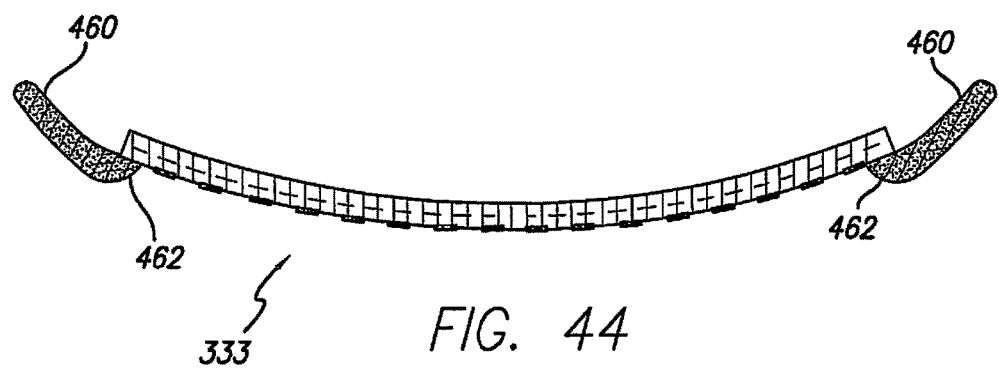
FIG. 44 depicts a flexible circuit array with a protective skirt bonded to the front side of the flexible circuit array with a progressively decreasing radius.

FIG. 44 depicts a flexible circuit array 333 with a protective skirt 460 bonded to the front side of the flexible circuit array 333 with a progressively decreasing radius and/or decreasing thickness toward the edges.

Figure 45:
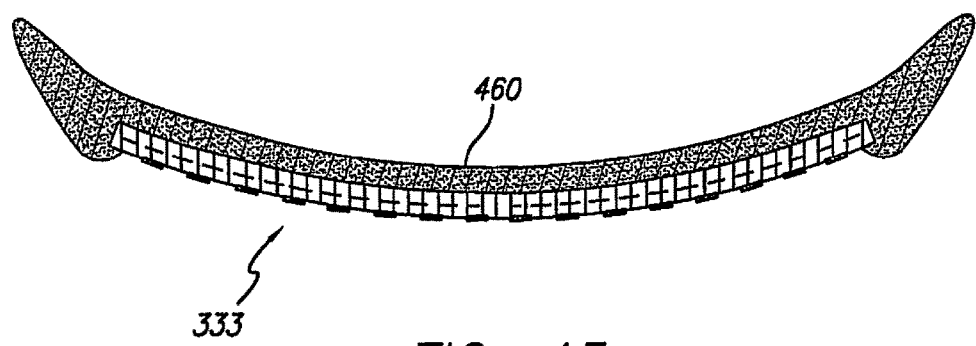
FIG. 45 depicts a flexible circuit array with a protective skirt bonded to the back side of the flexible circuit array, and molded around the edges of the flexible circuit array with a progressively decreasing radius.

FIG. 45 depicts a flexible circuit array 333 with a protective skirt 460 bonded to the back side of the flexible circuit array 333 and molded around the edges of the flexible circuit array with a progressively decreasing radius and/or decreasing thickness toward the edges.

Figure 46:
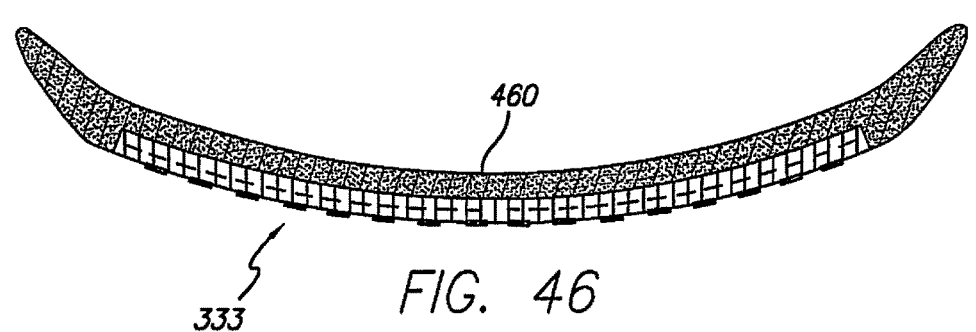
FIG. 46 depicts a flexible circuit array with a protective skirt bonded to the back side of the flexible circuit array, molded around the edges of the flexible circuit array, and flush with the front side of the array with a progressively decreasing radius.

FIG. 46 depicts a flexible circuit array 333 with a protective skirt 460 bonded to the back side of the flexible circuit array 333, molded around the edges of the flexible circuit array, and flush with the front side of the array with a progressively decreasing radius and/or decreasing thickness toward the edges.

Figure 47:
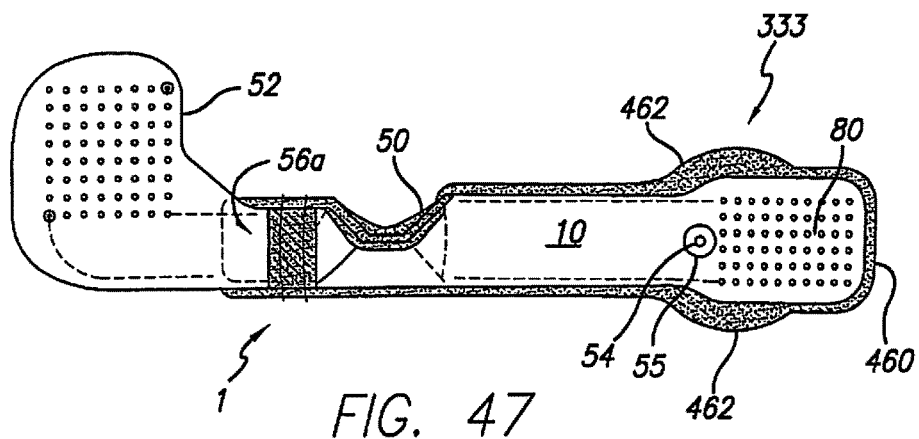
FIG. 47 depicts a side view of the flexible circuit array with a skirt containing a grooved and rippled pad instead of a suture tab.
Figure 48:
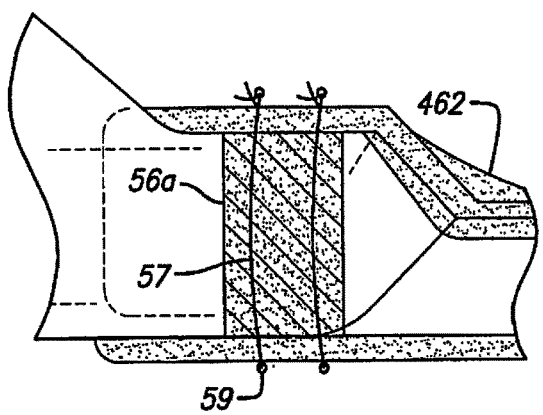
FIG. 48 depicts a side view of the enlarged portion of the skirt shown in FIG. 47 containing a grooved and rippled pad and a mattress suture.

FIG. 47 depicts a side view of the array with a skirt 460 containing a grooved and rippled pad 56A instead of a suture tab 56. This pad 56A has the advantage of capturing a mattress suture 57. A mattress suture 57 has the advantage of holding the groove or rippled pad 56A in two places as shown in FIG. 48. Each suture 57 is fixed on the tissue on two places 59. A mattress suture 57 on a grooved or rippled mattress 56A therefore provides a better stability.

Figure 49:
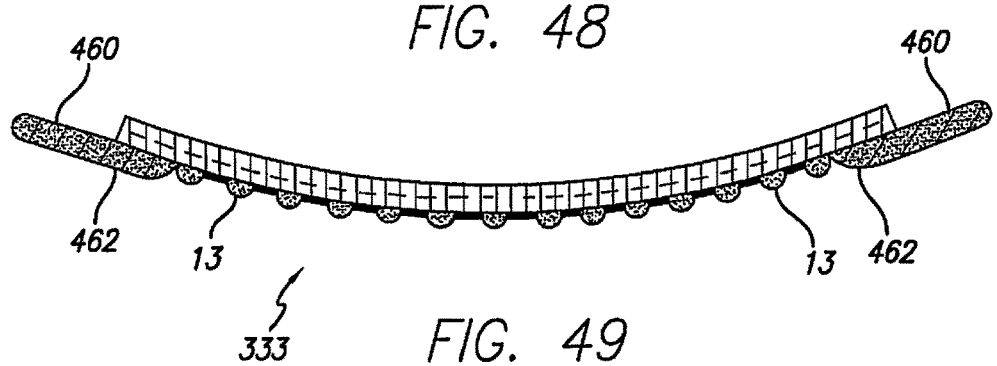
FIG. 49 depicts a flexible circuit array with a protective skirt bonded to the front side of the flexible circuit array with individual electrode windows.

FIG. 49 depicts a flexible circuit array 333 with a protective skirt 460 bonded to the front side of the flexible circuit array 333 with individual electrode 13 windows and with material, preferably silicone between the electrodes 13.

Figure 50:
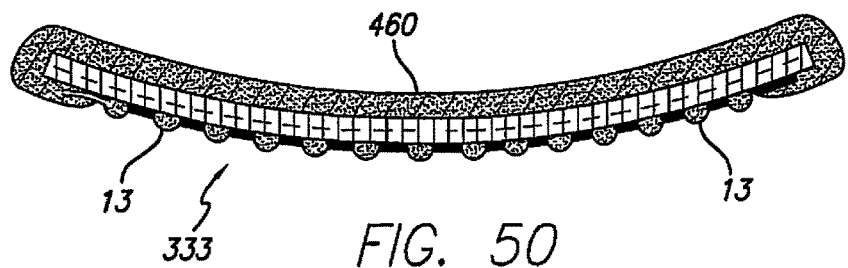
FIG. 50 depicts a flexible circuit array with a protective skirt bonded to the back side of the flexible circuit array and molded around the edges of the flexible circuit array with individual electrode windows.

FIG. 50 depicts a flexible circuit array with a protective skirt bonded to the back side of the flexible circuit array and molded around the edges of the flexible circuit array, with individual electrode windows and with material, preferably silicone, between the electrodes 13.

Figure 51:
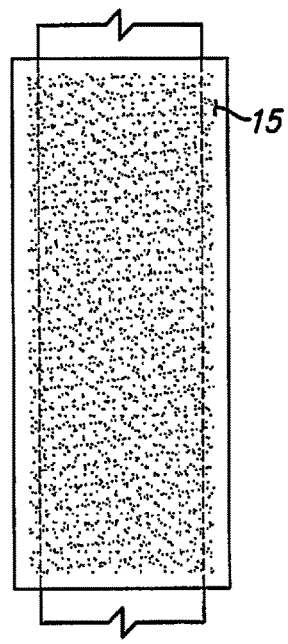
FIG. 51 shows a flange of soft polymer to be applied on top of the cable.
Figure 52:
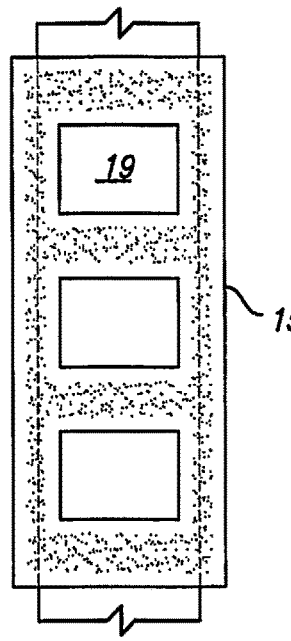
FIG. 52 shows a ladder-shaped soft polymer with square cutouts.
Figure 53:
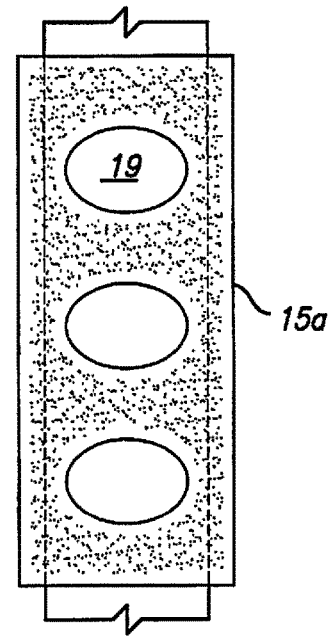
FIG. 53 shows a ladder-shaped soft polymer with perpendicular oval cutouts.
Figure 54:
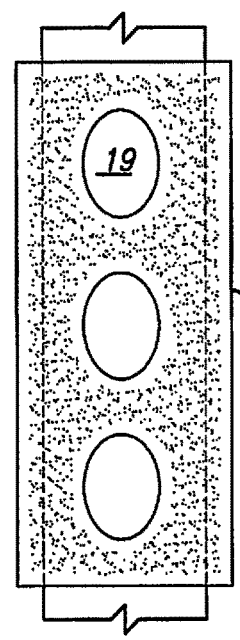
FIG. 54 shows a ladder-shaped soft polymer with parallel oval cutouts.
Figure 55:
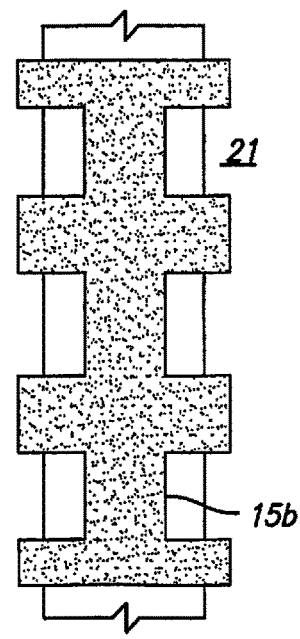
FIG. 55 shows a skeleton-shaped soft polymer.
Figure 56:
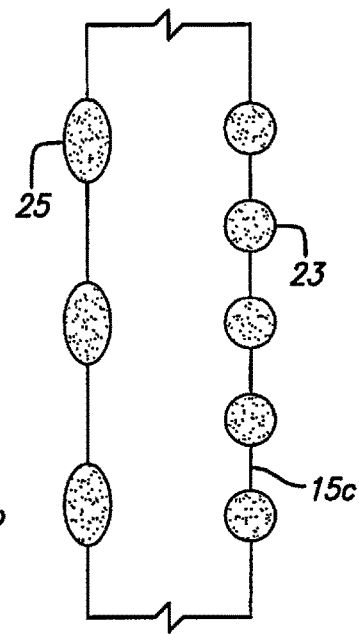
FIG. 56 shows soft polymer beads along the edge of the flexible cable.

FIGS. 51-56 show several surfaces to be applied to one or both sides of the flexible circuit array cable. The surfaces are thin films containing a soft polymer, preferably silicone. FIG. 51 shows a flange 15: A flange 15 can be a solid film of material containing silicone added to the surface of the polymer containing polyimide. FIGS. 52-54 show a ladder 15A: A ladder 15A is a flange with material removed from central portions in some shape 19. FIG. 55 shows a skeleton structure 15B. A skeleton 15B is a flange with material removed from perimeter portions in some shape 21. FIG. 56 shows a structure 15C with beads 23 and bumpers 25. A bead 23 is material added to perimeter portions of the polymer cable in some shape without material being added on the central area. A bumper 25 can be an extended or continuous version of the beaded approach. Both approaches are helpful in preventing any possible injury of the tissue by the polymer.

Figure 57:
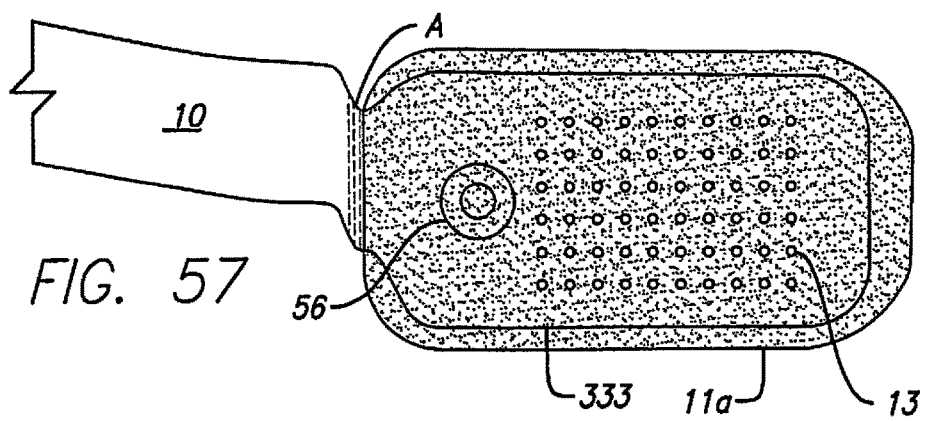
FIG. 57 depicts the top view of the flexible circuit array being enveloped within an insulating material.

FIG. 57 depicts the top view of the flexible circuit array 333 being enveloped within an insulating material 11a. The electrode array 333 comprises an oval-shaped electrode array body 333 and a plurality of electrodes 13 made of a conductive material, such as platinum or one of its alloys, but that can be made of any conductive biocompatible material such as iridium, iridium oxide or titanium nitride. The electrode array 333 is enveloped within an insulating material 11a that is preferably silicone. "Oval-shaped" electrode array body means that the body may approximate either a square or a rectangle shape, but where the corners are rounded. The material body 11a is made of a soft material that is compatible with the electrode array body 333. In a preferred embodiment the body 11a is made of silicone having hardness of about 50 or less on the Shore A scale as measured with a durometer. In an alternate embodiment the hardness is about 25 or less on the Shore A scale as measured with a durometer.

Figure 58:
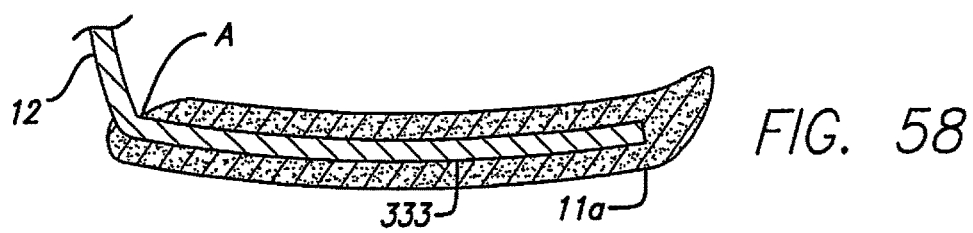
FIG. 58 depicts a cross-sectional view of the flexible circuit array being enveloped within an insulating material.

FIG. 58 depicts a cross-sectional view of the flexible circuit array 333 being enveloped within an insulating material 11a. It shows how the edges of the material body 11a are lifted off due to the contracted radius at the edges. The electrode array 333 preferably also contains a fold A between the cable 10 and the electrode array 333. The angle of the fold A secures a relief of the implanted material.

Figure 59:
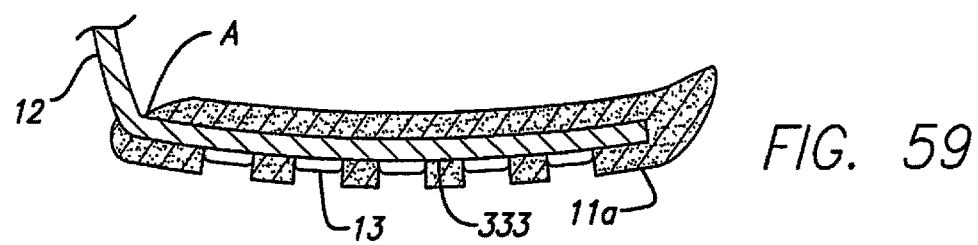
FIG. 59 depicts a cross-sectional view of the flexible circuit array being enveloped within an insulating material with open electrodes and the material between the electrodes.

FIG. 59 depicts a cross-sectional view of the flexible circuit array 333 being enveloped within an insulating material 11a with open electrodes 13 and the material 11a between the electrodes 13.

Figure 60:
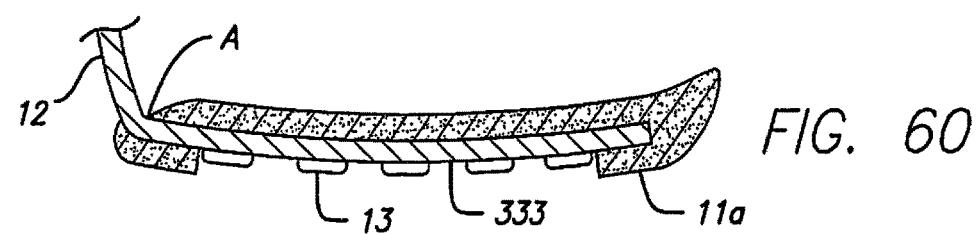
FIG. 60 depicts a cross-sectional view of the flexible circuit array being enveloped within an insulating material with open electrodes.

FIG. 60 depicts a cross-sectional view of the flexible circuit array 333 being enveloped within an insulating material 11a with open electrodes 13. This is another embodiment wherein the electrodes 13 are not separated by the material 11a but the material 11a is extended.

Figure 61:
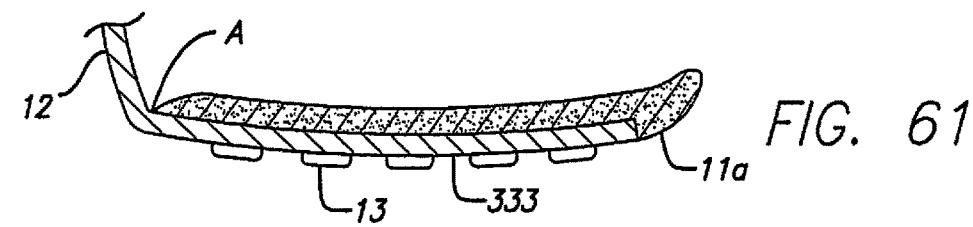
FIG. 61 depicts a cross-sectional view of the flexible circuit array being enveloped within an insulating material with electrodes on the surface of the material.

FIG. 61 depicts a cross-sectional view of the flexible circuit array 333 being enveloped within an insulating material 11a with electrodes 13 on the surface of the material 11. This is a further embodiment with the electrode 13 on the surface of the material 11a, preferably silicone. The embodiments shown in FIGS. 59, 60, and 61 show a preferred body 11a containing silicone with the edges being lifted off from the tissue due to contracted radius of the silicone body 11a at the edges.

Figures 62, 63:
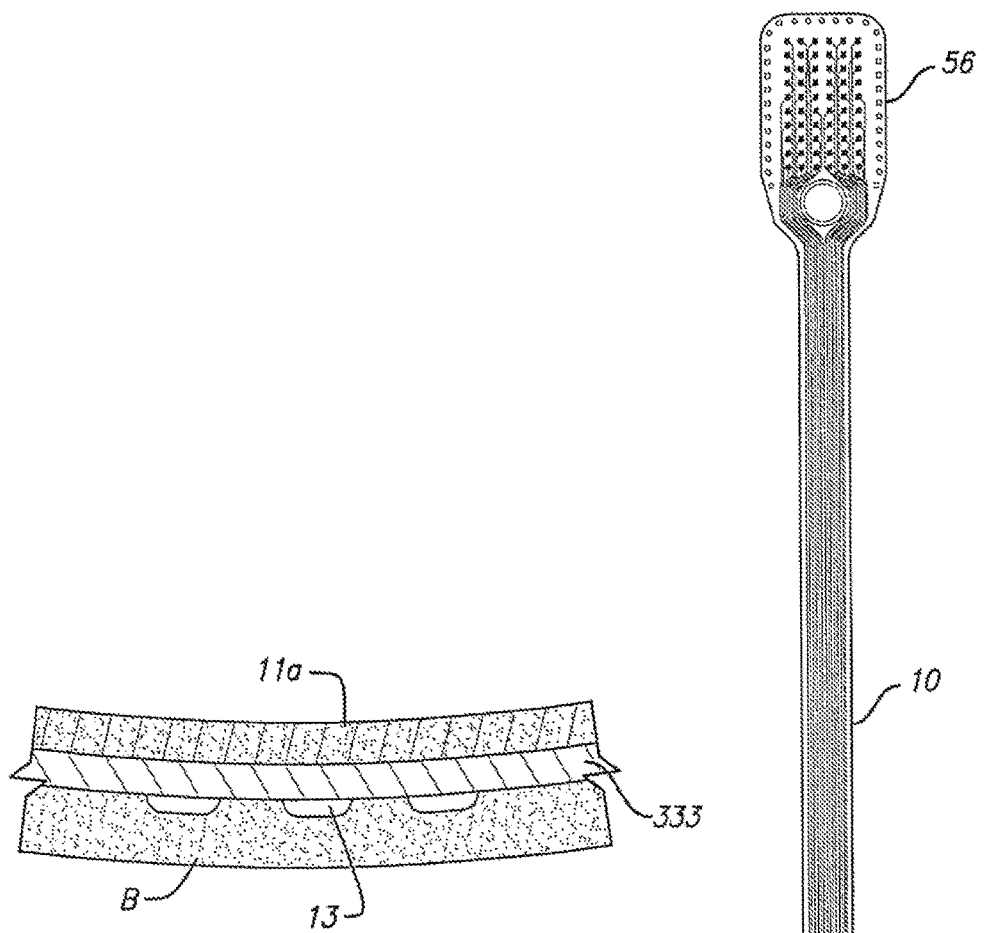
FIG. 62 depicts a side view of the enlarged portion of the flexible circuit array being enveloped within an insulating material with electrodes on the surface of the material inside the eye.
FIG. 63 shows the whole flexible polymer array with the bond pad and the traces with holes at the edge of the electrode array.

FIG. 62 shows the electrode array 333 and the electrodes 13 enveloped by the polymer material, preferably silicone 11a in intimate contact with the tissue B.

The electrode array 333 embedded in or enveloped by the polymer material, preferably silicone 11a can be preferably produced through the following steps. The soft polymer material which contains silicone is molded into the designed shape and partially hardened. The electrode array 333 which preferably contains polyimide is introduced and positioned in the partially hardened soft polymer containing silicone. Finally, the soft polymer 11a containing silicone is fully hardened in the designed shape enveloping the electrode array 333. The polymer body 11a has a shape with a decreasing radius at the edges so that the edges of the body 11a lift off from the brain B.

Figure 64:
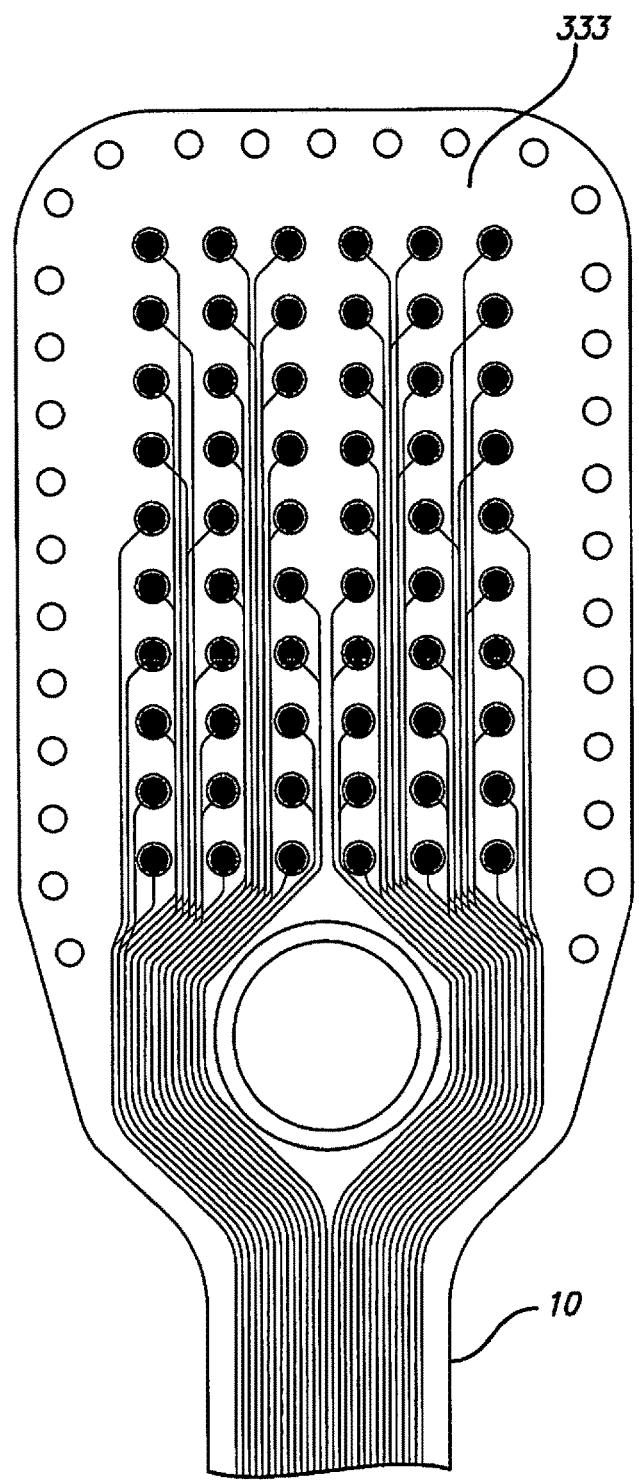
FIG. 64 shows an enlarged view of the electrode array with holes at the edge for providing a protective skirt.
Figure 65:
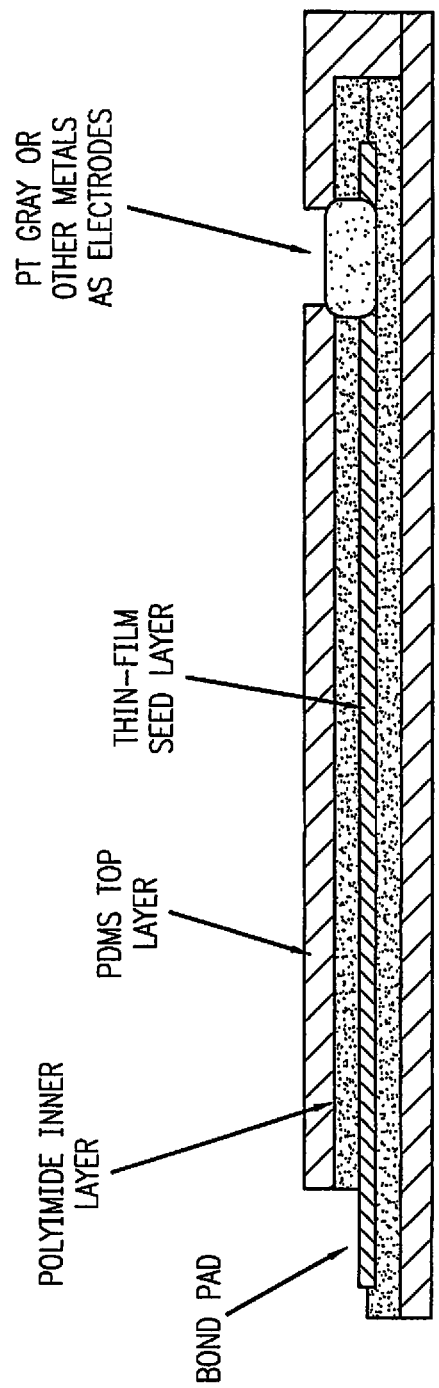
FIG. 65 shows a cross-sectional view of a polyimide array coated with PDMS.
Figure 66A:
FIGS. 66A-H show a sequence of steps 1 to 8 for coating a polyimide electrode with PDMS.
Figure 66B:
Figure 66C:
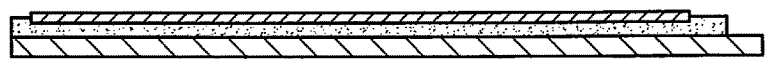
Figure 66D:
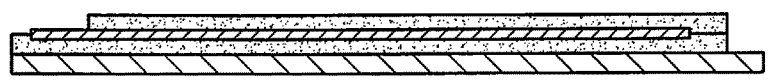
Figure 66E:
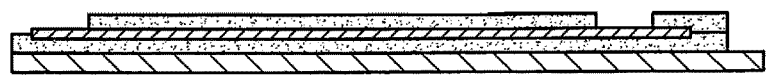
Figure 66F:
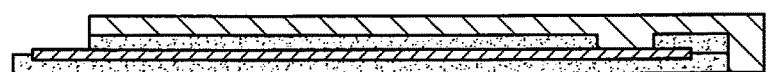
Figure 66G:
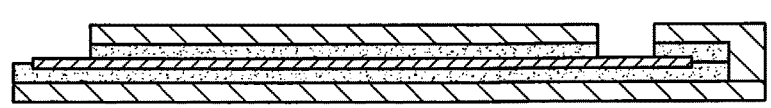
Figure 66H:
Figure 67A:
FIGS. 67A-G show a sequence of steps 1 to 7 for coating a polyimide electrode with PDMS.
Figure 67B:
Figure 67C:
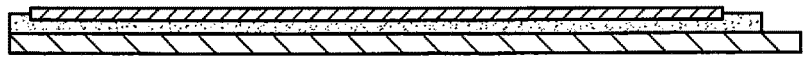
Figure 67D:
Figure 67E:
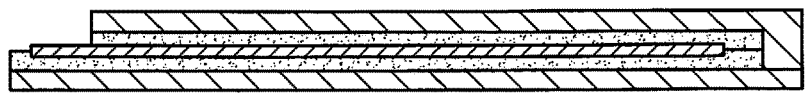
Figure 67F:
Figure 67G:
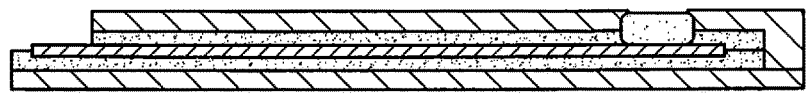

Referring to FIGS. 63 and 64, small holes are provided on the hard polymer and subsequently soft polymer containing PDMS is provided on the hard polymer. This way a partial or entire coating or a soft skirt at the edge is provided by a soft polymer on a hard polymer. The holes provide a stronger mechanical bond between the hard and soft polymer as the soft polymer bonds to itself through the holes.

The hard polymer contains polyimide, polyamide, LCP, PEEK, polypropylene, polyethylene, Parylene, or mixtures or copolymers or block copolymer thereof. The soft polymer contains at least one PDMS or silicone.

FIG. 66 shows a cross-sectional view of a polyimide array coated with PDMS. The cross-section shows two polyimide layers embedding a Pt thin film seed layer, with openings for Pt electrodes and bond pads. The electrodes can be Pt gray or other metals, such as Pt, Ir, IrOx, Pd, Au, Ni, Ru, Ti, alloys, conducting polymers, or layers thereof. The structure can be obtained in known procedures as described in US Patent Applications Nos. 2006/0247,754, 2006/0259,112, and 2007/0265,665, the entire content of which is incorporated herein as reference. The polyimide array is coated with a soft polymer, which contains PDMS.

The inventors have found that arrays containing only PDMS show metal trace breakage and/or metal trace/PDMS delaminating. Arrays containing only polyimide have edges which are too sharp and may not be biocompatible. Some pinholes or defects on the polyimide layer may cause leakage and corroding of traces.

One way to minimize such problems is to add a PDMS flange (skirt) to cover the edge of the array. During PDMS skirt attachment, some Pt gray electrodes may be covered which is not desired. Within the skirt windows, polyimide surface still may be exposed to the brain. A useful approach is to make a thinner polyimide array as the center piece, or core layer, and to coat the entire array with a thin layer of PDMS; and then open up only the electrode sites for Pt gray plating. This way the electrodes are not partially or entirely covered by PDMS. Pt gray plating is described in U.S. Pat. No. 6,974,533, the content of which is incorporated herein as reference.

The new flexible array is partially covered by PDMS or has no exposure of polyimide and is a virtual PDMS array with a polyimide center core layer.

The PDMS coated array eliminates the problem of undesired PDMS coverage on Pt gray electrodes because the Pt gray plating process takes place after the PDMS coating is accomplished.

The polyimide layer can be reduced from 6 μm to 3 μm due to the protection of the PDMS layers. The PDMS top coating can be 5 μm to 20 μm thick. The plated Pt gray electrode is slightly recessed. This helps to improve current distribution and provides benefits for clinical stimulation.

To increase the adhesion of PDMS to polyimide, some small holes on the polyimide layer (not only on the edges, but also in the centers and around electrodes) can be provided to achieve anchors for the PDMS as shown in FIGS. 63 and 64.

The center piece material can contain other polymers than polyimide such as polyamide, LCP, PEEK, polypropylene, polyethylene, Parylene or mixtures or copolymers or block copolymer thereof. Parylene, LCP or other materials can also be used for the outer protection layers.

FIG. 66 shows a sequence of steps 1 to 8 for coating a polyimide electrode with PDMS. The sequence of steps is as follows:

1. A first PDMS layer having a thickness of 5 μm to 20 μm is provided;
2. A first polyimide layer having a thickness of 2 μm to 4 μm is provided on the PDMS layer;
3. A Pt thin film having a thickness of 0.5 μm to 1.5 μm is provided on the first polyimide layer (A very thin layer of Ti or Cr of 500-5000 Armstrong can be deposited before and after this Pt thin-film deposition as an adhesion layer to promote good adhesion of Pt to polyimide);
4. A second polyimide layer having a thickness of 2 μm to 4 μm is provided on the Pt thin film;
5. Holes are provided in the second polyimide layer for bond pads and electrodes by photoresist patterning or dry or wet etch off technology;
6. A second PDMS layer having a thickness of 5 μm to 20 μm is provided on the second polyimide layer;
7. Holes are provided in the second PDMS layer for bond pads and electrodes by photoresist patterning or dry or wet etch off technology;
8. Electrodes are prepared in the provided holes by Pt gray or other metals.

FIG. 67 shows a sequence of steps 1 to 7 for coating a polyimide electrode with PDMS. The sequence of steps is as follows:

1. A first PDMS layer having a thickness of 5 μm to 20 μm is provided;
2. A first polyimide layer having a thickness of 2 μm to 4 μm is provided on the PDMS layer;
3. A Pt thin film having a thickness of 0.5 μm to 1.5 μm is provided on the first polyimide layer (A very thin layer of Ti or Cr of 500-5000 Armstrong can be deposited before and after this Pt thin-film deposition as an adhesion layer to promote good adhesion of Pt to polyimide);

4. A second polyimide layer having a thickness of 2 μm to 4 μm is provided on the Pt thin film;
5. A second PDMS layer having a thickness of 5 μm to 20 μm is provided on the second polyimide layer;
6. Holes are provided in the second PDMS layer and second polyimide layer for bond pads and electrodes by photoresist pattering or dry or wet etch off technology;
7. Electrodes are prepared in the provided holes by Pt gray or other metals.

In yet another embodiment (FIG. 68) it may be desirable to have both surface electrodes 333 and penetrating electrodes 313 on the same surface of the thin film lead 10 as shown in FIG. 68A. Although an alternating pattern of surface and penetrating electrodes is shown, it is understood that the invention is not restricted to this pattern and that any pattern is available. Also, there is no requirement that equal numbers of surface and penetrating spike electrodes be employed. FIG. 68B-68D, show methods of attachment of individual spike electrodes 313 to the thin film lead 10 (68B) or arrays of spike electrodes 13 to either the package 14 or the thin film lead 10 (68C and 68D). The individual spike electrodes or the spike electrode array is attached to the flexible circuit 10 or the package 14 using a flip-chip bumping process, and epoxy underfilled. In the flip-chip bumping process, bumps containing conductive adhesive placed on the base of individual spike electrodes 313 or the bond pads 92 of the spike electrode arrays 13 and bumps containing conductive adhesive placed on the electronic package 14 or the electrodes 333 of the thin film lead 10 are aligned and cured to build a conductive connection between the components.

In another embodiment (FIG. 69) it may be desirable to have electrodes on either side of the array. FIG. 69 a shows substantially planar surface electrodes 333 on either side of a thin film lead 10 that contains a single metal routing layer 94, although this single layer may be composed of more than one kind of metal. In this diagram, the electrodes are the same size and routed to either surface in an alternating fashion, but it should be understood that different electrode size and routing schemes could be employed. Similarly, although the electrodes are shown as slightly recessed, it should be understood that they may also be flush with the thin film lead surface or protruding slightly. FIG. 69B shows substantially planar surface electrodes 333 on either side of a thin film lead 10 that contains two metal routing layers 94, although each metal layer may be composed of more than one kind of metal. This arrangement has the advantage of creating higher density arrays on either side of the lead. It should be noted that even more metal layers may be used to increase the routing density and decrease size of the thin film lead and/or array. FIG. 69C shows substantially planar surface electrodes 333 on one side of a thin film lead 10 and penetrating electrodes 313 on the other side of a thin film lead that contains two metal routing layers 94, although each metal layer may be composed of more than one kind of metal. Note that the substantially planar electrodes 333 are actually protruding slightly, which is not a requirement. They could also be flush or slightly recessed compared to the thin film lead surface. Also, an array of penetrating electrodes could be attached rather than individual electrodes. FIG. 69D shows substantially planar surface electrodes 333 on one side of a thin film lead 10 and penetrating electrodes 313 on the other side of a thin film lead that contains two metal routing layers 94, although each metal layer may be composed of more than one kind of metal. Note that the substantially planar electrodes 333 differ in size and are actually flush. Additionally, the spike electrodes are of varying length.

FIG. 70 illustrates how a flexible array of penetrating electrodes could be formed, in this case, a penetrating spike electrode 313. FIG. 70 illustrates how a flexible array of penetrating electrodes could be formed. The advantage of a flexible penetrating electrode array is that the exposed electrodes at the end of or on the penetrating electrodes should end up at similar depths. This overcomes a disadvantage of stiff penetrating electrode arrays, which when implanted on a highly curved surface, such as those encountered in the brain, the active electrodes often end up in different functional layers of the brain. Thus, not all of the penetrating electrodes will be located in the target region of treatment. In this case (FIG. 68A), a single or multiple penetrating spike electrode(s) 313 is inserted through vias in the thin film lead 10. Preferred embodiments employ penetrating electrodes made from platinum, iridium, an alloy of platinum and iridium, activated iridium, tungsten, and titanium nitride. A conductive medium such as conductive epoxy 381 is used to electrically connect the spike electrodes 313 to the conductive metal traces 94. The penetrating electrodes could be made of any conductive and biocompatible medium. When forming such penetrating electrode arrays, the epoxy would be cured and then the portion of the electrodes protruding from the backside of the thin film lead would be covered in a non-conductive medium or layers of non-conductive media 360 chosen from biocompatible polymers including epoxy, silicone, Parylene, and others. Several different penetrating electrode structures may be employed as required.

FIG. 70 (A) shows two possibilities, a spike electrode and a nail electrode. The latter has advantages in manufacturing (the electrode will not accidentally slip through the via) and in maintaining electrical contact. By covering each electrode individually, the flexibility of the array is maintained as shown in FIG. 70 (B), where the thin film lead 10 generally conforms to a surface of the brain 11 and so the tips of the penetrating electrodes 313, which protrude normally to the local surface of the thin film lead, are not equidistant once implanted in the brain.

FIG. 70 (C) illustrates that the active electrode area on a penetrating electrode could have different sizes, shapes, and locations along the penetrating shaft. That is, the penetrating conductive electrodes 313 are electrically passivated over some or most of their area 361, and a window is opened in this passivation at the desired stimulation or recording site 362. The passivation of the conductive penetrating electrode may be accomplished through anodization, chemical modification of the surface, or by applying a coating of non-conductive biocompatible materials such as silicone, epoxy, Parylene, and others. The exposed region or active electrode site may be located at the tip of the penetrating electrode or somewhere along the shaft and may be made by standard patterning techniques. The size and shaped of the active electrode are also easily varied.

Accordingly, what has been shown is an improved method making a hermetic package for implantation in a body. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What we claim is:

1. A neural stimulator comprising:
a hermetic package enclosing electronics suitable to be implanted within a head;
a flange defining a plurality of voids around the hermetic package suitable to accept screws adapted for mounting the hermetic package to the cranium;
a return electrode formed as part of said hermetic package and electrically coupled to said electronics and
a flexible thin film electrode array electrically coupled to said electronics suitable for direct contact with and direct stimulation of the brain including a flexible polymer base layer;
patterned metal traces deposited on said flexible polymer base layer, the metal traces forming a bond pad portion connected to the hermetic electronics package, an electrode portion adapted for contact with the brain and a cable portion connecting the bond pad portion to the electrode portion; and
a flexible polymer top layer deposited on said flexible polymer base layer and said metal traces and defining voids exposing said electrodes.

2. The neural stimulator according to claim 1, further comprising a plurality of thin film electrode arrays electrically coupled to said electronics suitable for direct contact with and direct stimulation of the brain.

3. The neural stimulator according to claim 1, wherein said electrode array includes greater than 30 electrodes.

4. The neural stimulator according to claim 1, wherein said electrode array includes more than 50 electrodes.

5. The neural stimulator according to claim 1, wherein said electrode array includes more than 75 electrodes.

6. The neural stimulator according to claim 1, wherein said electrode array includes more than 100 electrodes.

7. The neural stimulator according to claim 1, wherein said electrode array includes more than 200 electrodes.

8. The neural stimulator according to claim 1, further comprising: a plurality of electrically coupled hermetic packages enclosing electronics.

9. The neural stimulator according to claim 8, wherein a first hermetic package encloses electronics, and a second hermetic package encloses a demultiplexer electrically coupled to said electronics.

10. The neural stimulator according to claim 1, further comprising a plurality of coils electrically coupled to said electronics.

11. The neural stimulator according to claim 10, wherein said plurality of coils, include a power coil and a data coil.

12. The neural stimulator according to claim 1, further comprising a coil electrically connected to the electronics.

13. The neural stimulator according to claim 12, wherein the coil provides power to the electronics.

14. The neural stimulator according to claim 12, wherein the coil provides data to the electronics.

* * * * *